US008404823B2

(12) United States Patent
Sako et al.

(10) Patent No.: US 8,404,823 B2
(45) Date of Patent: Mar. 26, 2013

(54) CYTOKINE PRODUCTION REGULATOR GENE AND USE THEREOF

(75) Inventors: Tomoyuki Sako, Minato-ku (JP); Emi Yasuda, Minato-ku (JP); Masaki Serata, Minato-ku (JP); Satoshi Matsumoto, Minato-ku (JP); Kan Shida, Minato-ku (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 651 days.

(21) Appl. No.: 12/447,370

(22) PCT Filed: Oct. 26, 2007

(86) PCT No.: PCT/JP2007/001176
§ 371 (c)(1),
(2), (4) Date: Dec. 7, 2009

(87) PCT Pub. No.: WO2008/053588
PCT Pub. Date: May 8, 2008

(65) Prior Publication Data
US 2010/0144551 A1 Jun. 10, 2010

(30) Foreign Application Priority Data

Oct. 27, 2006 (JP) ................. 2006-292934

(51) Int. Cl.
*C07H 21/02* (2006.01)
*C12P 1/00* (2006.01)
*C12Q 1/68* (2006.01)
*C12N 1/20* (2006.01)
*C12N 15/00* (2006.01)
*C12N 15/74* (2006.01)
*C40B 40/00* (2006.01)

(52) U.S. Cl. ....... 536/23.1; 435/6.1; 435/41; 435/252.3; 435/320.1; 435/471; 506/13

(58) Field of Classification Search ................. 536/23.1; 435/6.1, 41, 253.3, 320.1, 471; 506/13
See application file for complete search history.

(56) References Cited

U.S. PATENT DOCUMENTS 4,347,240 A * 8/1982 Mutai et al. ............... 424/282.1
5,733,765 A 3/1998 Mollet et al.
6,319,692 B1 * 11/2001 Kadota et al. ................ 435/91.1

FOREIGN PATENT DOCUMENTS

| JP | 63-126827 | 5/1988 |
|---|---|---|
| JP | 63-196521 | 8/1988 |
| JP | 8-92112 | 4/1996 |
| JP | 9-269 | 1/1997 |
| JP | 10-139674 | 5/1998 |
| JP | 2002-241292 | 8/2002 |
| JP | 2003-63991 | 3/2003 |
| JP | 2003-73286 | 3/2003 |
| JP | 2003 73286 | 3/2003 |
| WO | 99 54475 | 10/1999 |
| WO | WO 03/064607 A2 | 8/2003 |
| WO | WO 03/064607 A3 | 8/2003 |

OTHER PUBLICATIONS

Peant, B. et al., "Comparative analysis of the xopolysacharide biosynthesis gene clusters from four strains of *Lactobacilus rhamnosus*", Microbiology, vol. 151, pp. 1839-1851, (2005).
Chabot, S. et al., "Exopolysaccharides from *Lactobacilus rhamnosus* RW-9595M stimulate TNF, IL-6 and IL-12 in human and mouse cultured immunocompetent cells, and IFN-γ in mouse splenocytes", LAIT, vol. 81, No. 6, pp. 683-697, (2001).
Provencher, C. et al., "Consensus-Degenerate Hybrid Oligonucleotide Primers for Amplication of Priming Glycosyltransferase Genes of the Exopolysaccharide Locus in Strains of the *Lactobacillus casei* Group", Applied and Environmental Microbiology, vol. 69, No. 6, pp. 3299-3307, (2003).
Peant, B. et al., "*Lactobacilus rhamnosus* strain RW-9595M Wzd, (wzd), Wze (wze), Wzx (wzx), Welf (welf), WeIG (weIG), WeIH (weIH), Well (well), Wzy (wzy), WeIJ (welJ), Wzm (wzm), RmIA (rmIA), RmIC (rmIC), RmIB (rmIB), RmID (rmID), WeIE (weIE), Wzr (wzr), Wzb (wzb), CIpL (cIpL), Tnp (TNP), Nrp (nrp), and unknown protein genes, complete cds", Genbank, (Jun. 9m 2005), Accession No. AY659979, [retrieved on Jan. 21, 2008], Retrieved from the Internet:<URL:http://www.ncbi.nlm.nih.gov/entrez/viewer.fcgi?db=nuccore&id=56684523>.
Van Calsteren, M-R. et al., "Structure determination of the exopolysaccharide produced by *Lactobacillus rhamnosus* strains RW-9595M and R", Biochem. J., vol. 363, pp. 7-17, (2002).
Lamothe, G.T. et al., "Genetic and biochemical characterization of exopolysaccharide biosynthesis by *Lactobacillus delbrueckii* subsp. Bulgaricus", Arch. Micriobiol., vol. 178, pp. 218-228, (2002).
Makino, S. et al., "Immunomodulatory effects of polysaccharide from *Lactobacillus delbrueckii* subsp. Bulgaricus", Milk Science, vol. 53, No. 3, pp. 161-164, (2004), (with partial English translation).
Van Kranenburg, R. et al., "Molecular characterization of the plasmid-encoded eps gene cluster essential for exopolysaccharide biosynthesis in *Lactococcus lactis*", Mol. Microbiol., vol. 24, No. 2, pp. 387-397, (1997).
Notice of Reasons for Rejection issued Mar. 21, 2012 in Japanese Patent Application No. 2008-541990 (with English translation).

(Continued)

*Primary Examiner* — Amber D. Steele
(74) *Attorney, Agent, or Firm* — Oblon, Spivak, McClelland, Maier & Neustadt, L.L.P.

(57) ABSTRACT

The invention provides a gene encoding a protein selected from among the following proteins (a) to (c): (a) a protein having any of the amino acid sequences of SEQ ID NOs: 2, 4, 6, 8, 10, 12, 14, 16, 82, 84, 86, 88, 90, 92, 94, 96, 98, 100, 102, 104, 106, and 108; (b) a protein which has an amino acid sequence equivalent to any of the amino acid sequences of (a), except that one to several amino acid residues are deleted, substituted, or added, and which exhibits cytokine production regulatory activity; and (c) a protein which has an amino acid sequence having 90% or higher identity to any of the amino acid sequences of (a), and which exhibits cytokine production regulatory activity, as well as a gene useful for regulating cytokine production and use of the gene.

26 Claims, 7 Drawing Sheets

OTHER PUBLICATIONS

Richard Van Kranenburg, et al., "Functional Analysis of Glycosyltransferase Genes from *Lactococcus lactis* and Other Gram-Positive Cocci: Complementation, Expression, and Diversity", Journal of Bacteriology, vol. 181, No. 11, Jun. 1999, pp. 6347-6353.

Extended European Search Report issued Dec. 1, 2010, in Application No. / Patent No. 07827955.1-1212 / 2075332 PCT/JP2007001176.

Emi Yasuda, et al., "Suppressive Effect on Activation of Macrophages by *Lactobacillus casei* Strain Shirota Genes Determining the Synthesis of Cell Wall- Associated Polysaccharides", Applied and Environmental Microbiology, vol. 74, No. 15, XP-002607013, Aug. 2008, pp. 4746-4755 (with Author's Correction, XP-002610701, vol. 75, No. 4, Feb. 2009, p. 1221).

* cited by examiner

SEQUENCE LISTING

<160> NUMBER OF SEQ ID NOS: 108

<210> SEQ ID NO 1
<211> LENGTH: 930
<212> TYPE: DNA
<213> ORGANISM: Lactobacillus casei

<400> SEQUENCE: 1

```
atgaacgagc aaatcgacct tcacggctg tggaatgtgt ttaaacgcag ctttattgca      60
atggttatcc ttggcatttt atgtatggtt gcggcttatt ttggtgcgaa gacttttatt     120
gtaccaaaat acgaagctga cacttcgctg ttggtcaacc gcaagcagga taatgatcca    180
aatatgcagt tgaatgcaca acaagctgat gtgcagatca ttaatactta taaagatatt    240
attacgcgtc cggttgtatt acaggctgtt gctggtgatt tgacaagtcc gcggcgcgtg    300
ataaccaaga aagctgaaaa agcagtttat ggtacgcgat ataatgcgac gaccggcatt    360
cgtgaacggt atgttgtgga aaaagccaaa ccagctcagt acaaactaaa accagcaaaa    420
tattcaaact taacagcgga tgatctagcc aaaatggttt cggtatcaac ccaacaaaat    480
tctcaagtgt ttacggttag tgtcaaggat actgatccaa ttcgagcgcg tgatatagca    540
aatgaagttg ccaaggtatt taaacaaaaa attgcccaaa tcatgagtat ttccaacgtc    600
tctattgttt cggaggcttc ggctaaccta tcgccggttt caccgaagtt accattgatt    660
gcccttgtag ggttactttt aggcatactg gttgcattca tctggggatt aattcgagag    720
cttacagacc aaaccattaa agaccttgac tttattactg atgatttggg tttagtcaat    780
cttggcatcg taaattatgt taagcgcatg aaagacatgg accaagcgat tgcgaaggtt    840
aaatctgaaa atgaagagtc aaaagacgat gaatctttg aagaattcaa tatgcaggat    900
ttacctcagc gcagccgtcg ccggatttga                                      930
```

<210> SEQ ID NO 2
<211> LENGTH: 309
<212> TYPE: PRT
<213> ORGANISM: Lactobacillus casei -continued

<400> SEQUENCE: 2

| | | | | | | | | | | | | | | |
|---|---|---|---|---|---|---|---|---|---|---|---|---|---|---|
| Met | Asn | Glu | Gln | Ile | Asp | Leu | Ser | Arg | Leu | Trp | Asn | Val | Phe | Lys | Arg |
| 1 | | | | 5 | | | | | 10 | | | | | 15 | |
| Ser | Phe | Ile | Ala | Met | Val | Ile | Leu | Gly | Ile | Leu | Cys | Met | Val | Ala | Ala |
| | | | 20 | | | | | 25 | | | | | 30 | | |
| Tyr | Phe | Gly | Ala | Lys | Thr | Phe | Ile | Val | Pro | Lys | Tyr | Glu | Ala | Asp | Thr |
| | | | 35 | | | | | 40 | | | | | 45 | | |
| Ser | Leu | Leu | Val | Asn | Arg | Lys | Gln | Asp | Asn | Asp | Pro | Asn | Met | Gln | Leu |
| | 50 | | | | | 55 | | | | | 60 | | | | |
| Asn | Ala | Gln | Gln | Ala | Asp | Val | Gln | Ile | Ile | Asn | Thr | Tyr | Lys | Asp | Ile |
| 65 | | | | | 70 | | | | | 75 | | | | | 80 |
| Ile | Thr | Arg | Pro | Val | Val | Leu | Gln | Ala | Val | Ala | Gly | Asp | Leu | Thr | Ser |
| | | | | 85 | | | | | 90 | | | | | 95 | |
| Pro | Arg | Arg | Val | Ile | Thr | Lys | Lys | Ala | Glu | Lys | Ala | Val | Tyr | Gly | Thr |
| | | | 100 | | | | | 105 | | | | | 110 | | |
| Arg | Tyr | Asn | Ala | Thr | Thr | Gly | Ile | Arg | Glu | Arg | Tyr | Val | Val | Glu | Lys |
| | | | 115 | | | | | 120 | | | | | 125 | | |
| Ala | Lys | Pro | Ala | Gln | Tyr | Lys | Leu | Lys | Pro | Ala | Lys | Tyr | Ser | Asn | Leu |
| | 130 | | | | | 135 | | | | | 140 | | | | |
| Thr | Ala | Asp | Asp | Leu | Ala | Lys | Met | Val | Ser | Val | Ser | Thr | Gln | Gln | Asn |
| 145 | | | | | 150 | | | | | 155 | | | | | 160 |
| Ser | Gln | Val | Phe | Thr | Val | Ser | Val | Lys | Asp | Thr | Asp | Pro | Ile | Arg | Ala |
| | | | | 165 | | | | | 170 | | | | | 175 | |
| Arg | Asp | Ile | Ala | Asn | Glu | Val | Ala | Lys | Val | Phe | Lys | Gln | Lys | Ile | Ala |
| | | | 180 | | | | | 185 | | | | | 190 | | |
| Gln | Ile | Met | Ser | Ile | Ser | Asn | Val | Ser | Ile | Val | Ser | Glu | Ala | Ser | Ala |
| | | | 195 | | | | | 200 | | | | | 205 | | |
| Asn | Leu | Ser | Pro | Val | Ser | Pro | Lys | Leu | Pro | Leu | Ile | Ala | Leu | Val | Gly |
| | 210 | | | | | 215 | | | | | 220 | | | | |
| Leu | Leu | Leu | Gly | Ile | Leu | Val | Ala | Phe | Ile | Trp | Gly | Leu | Ile | Arg | Glu |
| 225 | | | | | 230 | | | | | 235 | | | | | 240 |
| Leu | Thr | Asp | Gln | Thr | Ile | Lys | Asp | Leu | Asp | Phe | Ile | Thr | Asp | Asp | Leu |
| | | | | 245 | | | | | 250 | | | | | 255 | |
| Gly | Leu | Val | Asn | Leu | Gly | Ile | Val | Asn | Tyr | Val | Lys | Arg | Met | Lys | Asp |
| | | | 260 | | | | | 265 | | | | | 270 | | |
| Met | Asp | Gln | Ala | Ile | Ala | Lys | Val | Lys | Ser | Glu | Asn | Glu | Glu | Ser | Lys |
| | | | 275 | | | | | 280 | | | | | 285 | | |
| Asp | Asp | Glu | Ser | Phe | Glu | Phe | Asn | Met | Gln | Asp | Leu | Pro | Gln | Arg |
| | 290 | | | | | 295 | | | | | 300 | | | | |
| Ser | Arg | Arg | Arg | Ile |
| 305 | | | | |

<210> SEQ ID NO 3
<211> LENGTH: 759
<212> TYPE: DNA
<213> ORGANISM: Lactobacillus casei

<400> SEQUENCE: 3

| | | | | | |
|---|---|---|---|---|---|
| atgagcttga | atgggatttt | taaaaaattc | acgcatcgtg | atgaagaaga | taatgaaaca | 60 |
| cagaaaaacg | gtgttatgtt | ggttactttt | gcagagccaa | acatgttgt | tgctgaacag | 120 |
| tttcgaacag | tgagaacgaa | tattgagttt | gctggggctg | cattagatcg | atgtgaagtc | 180 |
| gtaatgttca | cttcttcaag | catgtctgaa | gggaagtcaa | ctgtttcggc | aaacgttgct | 240 |
| gtaacttggg | ctcaagcggg | ggaaaaagtt | ttattgattg | atgcagattt | acgtagaccg | 300 |

-continued

```
acagttcatg ctacttttag aacgctcaac cttgaagggg ttacgactgt attaacgggg    360
aaaactaaac catcagatgt tgtagaaaaa acatttgtcg acaatctcga cattattaca    420
tccggcccag tgccaccaaa tccctcagaa cttttaaatt caaagcgtat ggcaaatttg    480
ttggaatggg gtcgagcaaa ttatgacatc attgttttag atgctccttc agttttggca    540
gtatcagatg tacaggtgtt agttccaaag actgacgggg ttgttgtcgt aacaaacatg    600
ggaaaaacct taaaggtga tttgaagaga actgttgagg tcttgaagct ggcaaaggca    660
aaaattcttg ggtctgtcga acgagtgcgc gctacgaagg gcgatcgcgg ttatggctat    720
ggttatggtt acgggtatca aagtaacgat gagcgttag                           759
```

<210> SEQ ID NO 4
<211> LENGTH: 252
<212> TYPE: PRT
<213> ORGANISM: Lactobacillus casei

<400> SEQUENCE: 4

```
Met Ser Leu Asn Gly Ile Phe Lys Lys Phe Thr His Arg Asp Glu Glu
1               5                  10                  15

Asp Asn Glu Thr Gln Lys Asn Gly Val Met Leu Val Thr Phe Ala Glu
            20                  25                  30

Pro Lys His Val Val Ala Glu Gln Phe Arg Thr Val Arg Thr Asn Ile
        35                  40                  45

Glu Phe Ala Gly Ala Ala Leu Asp Arg Cys Glu Val Val Met Phe Thr
    50                  55                  60

Ser Ser Ser Met Ser Glu Gly Lys Ser Thr Val Ser Ala Asn Val Ala
65                  70                  75                  80

Val Thr Trp Ala Gln Ala Gly Glu Lys Val Leu Leu Ile Asp Ala Asp
                85                  90                  95

Leu Arg Arg Pro Thr Val His Ala Thr Phe Arg Thr Leu Asn Leu Glu
            100                 105                 110

Gly Val Thr Thr Val Leu Thr Gly Lys Thr Lys Pro Ser Asp Val Val
        115                 120                 125

Glu Lys Thr Phe Val Asp Asn Leu Asp Ile Ile Thr Ser Gly Pro Val
    130                 135                 140

Pro Pro Asn Pro Ser Glu Leu Leu Asn Ser Lys Arg Met Ala Asn Leu
145                 150                 155                 160

Leu Glu Trp Gly Arg Ala Asn Tyr Asp Ile Ile Val Leu Asp Ala Pro
                165                 170                 175

Ser Val Leu Ala Val Ser Asp Val Gln Val Leu Val Pro Lys Thr Asp
            180                 185                 190

Gly Val Val Val Thr Asn Met Gly Lys Thr Leu Lys Gly Asp Leu
        195                 200                 205

Lys Arg Thr Val Glu Val Leu Lys Leu Ala Lys Ala Lys Ile Leu Gly
    210                 215                 220

Ser Val Glu Arg Val Arg Ala Thr Lys Gly Asp Arg Gly Tyr Gly Tyr
225                 230                 235                 240

Gly Tyr Gly Tyr Gly Tyr Gln Ser Asn Asp Glu Arg
                245                 250
```

<210> SEQ ID NO 5
<211> LENGTH: 1182
<212> TYPE: DNA
<213> ORGANISM: Lactobacillus casei -continued

```
<400> SEQUENCE: 5
gtgacagaga agcgtaaggt atttatcatt ggatcaaaag gtacaccagc aaaatatggt    60
ggctttgaga cgttcgtaga caatttagtt tctcgtcaga atagcagtca aattaaatac   120
tttattgcct gtcgaagaga cttatccgac aataaagcgg attttatga ctataaaaaa   180 gcaacttgtt ttaatgttga tgttcccaat ataggacctg ccaaagcaat tttgtatgat   240
cttcgtgctt tgtcttggac gttagactat attcagaaga ataacattag gggagcaatt   300
gtttatattc ttgcttgtcg ggttggtcct ttcttaaagc attatagtaa acggcttaaa   360
ctttacgaca cacaaatttt tgtgaatccg gatggtcacg aatggatgag gccaagtgg   420 ggatttttg ttaggaaata ctggaagtta tctgaacggt taatgattaa agatgcagat   480
ttgatcatct gtgatagtaa acacattgaa ctgtatattc gggaaaaata tcgcagttac   540
aaaccaaaga cgatatattc atcatatggc gccgatgttg ccacctcaca agacgtgaaa   600
gcacaagatc ttcaaaactg gtttaataaa aagcagatta gttcaggtca gtactatcta   660
gttgtgggta gatttgtacc agaaaataat taccaaacaa ttgttgctga atttgaaaaa   720
tccaaaacca aaaggattt ggtaatcata acaaatcccg ataataccaa gttcttgaaa   780
tcacttaaag accaaactgg ctttgaaaaa gataacagaa ttaaatttgt tggcactgtg   840
tatgacaagg acctttatc tgcaatcagg agaaatgcat ttggatacat ccatgggcat   900
gaagtgggcg gaactaatcc ctctttattg gaagctttgg gaaccacaaa tctaaacttg   960
ctgttcgatg ttgggttcaa caagaagtg gggcaggatg ctgctgttta ctggaataag  1020
caggctggca atttagccca tattattaat agagtggatc aaatgtcgga agaagaacgt  1080
caaacccttg gcaaaaaggc caagcagatc attgacaaaa acttctcctg ggataagata  1140
gtaagtcaaa atgaaagaca atttatcgat ggaaaaatat aa                     1182

<210> SEQ ID NO 6
<211> LENGTH: 393
<212> TYPE: PRT
<213> ORGANISM: Lactobacillus casei

<400> SEQUENCE: 6

Val Thr Glu Lys Arg Lys Val Phe Ile Ile Gly Ser Lys Gly Thr Pro
1               5                   10                  15

Ala Lys Tyr Gly Gly Phe Glu Thr Phe Val Asp Asn Leu Val Ser Arg
            20                  25                  30

Gln Asn Ser Ser Gln Ile Lys Tyr Phe Ile Ala Cys Arg Arg Asp Leu
        35                  40                  45

Ser Asp Asn Lys Ala Asp Leu Tyr Asp Tyr Lys Lys Ala Thr Cys Phe
    50                  55                  60

Asn Val Asp Val Pro Asn Ile Gly Pro Ala Lys Ala Ile Leu Tyr Asp
65                  70                  75                  80

Leu Arg Ala Leu Ser Trp Thr Leu Asp Tyr Ile Gln Lys Asn Asn Ile
                85                  90                  95

Arg Gly Ala Ile Val Tyr Ile Leu Ala Cys Arg Val Gly Pro Phe Leu
            100                 105                 110

Lys His Tyr Ser Lys Arg Leu Lys Leu Tyr Asp Thr Gln Ile Phe Val
        115                 120                 125

Asn Pro Asp Gly His Glu Trp Met Arg Ala Lys Trp Gly Phe Phe Val
    130                 135                 140

Arg Lys Tyr Trp Lys Leu Ser Glu Arg Leu Met Ile Lys Asp Ala Asp
145                 150                 155                 160
```

Leu Ile Ile Cys Asp Ser Lys His Ile Glu Leu Tyr Ile Arg Glu Lys
            165                 170                 175

Tyr Arg Ser Tyr Lys Pro Lys Thr Ile Tyr Ser Ser Tyr Gly Ala Asp
            180                 185                 190

Val Ala Thr Ser Gln Asp Val Lys Ala Gln Asp Leu Gln Asn Trp Phe
            195                 200                 205

Asn Lys Lys Gln Ile Ser Ser Gly Gln Tyr Tyr Leu Val Val Gly Arg
            210                 215                 220

Phe Val Pro Glu Asn Asn Tyr Gln Thr Ile Val Ala Glu Phe Glu Lys
225                 230                 235                 240

Ser Lys Thr Lys Lys Asp Leu Val Ile Ile Thr Asn Pro Asp Asn Thr
            245                 250                 255

Lys Phe Leu Lys Ser Leu Lys Asp Gln Thr Gly Phe Glu Lys Asp Asn
            260                 265                 270

Arg Ile Lys Phe Val Gly Thr Val Tyr Asp Lys Asp Leu Leu Ser Ala
            275                 280                 285

Ile Arg Arg Asn Ala Phe Gly Tyr Ile His Gly His Glu Val Gly Gly
            290                 295                 300

Thr Asn Pro Ser Leu Leu Glu Ala Leu Gly Thr Thr Asn Leu Asn Leu
305                 310                 315                 320

Leu Phe Asp Val Gly Phe Asn Lys Glu Val Gly Gln Asp Ala Ala Val
            325                 330                 335

Tyr Trp Asn Lys Gln Ala Gly Asn Leu Ala His Ile Ile Asn Arg Val
            340                 345                 350

Asp Gln Met Ser Glu Glu Glu Arg Gln Thr Leu Gly Lys Lys Ala Lys
            355                 360                 365

Gln Ile Ile Asp Lys Asn Phe Ser Trp Asp Lys Ile Val Ser Gln Asn
            370                 375                 380

Glu Arg Gln Phe Ile Asp Gly Lys Ile
385                 390

<210> SEQ ID NO 7
<211> LENGTH: 1158
<212> TYPE: DNA
<213> ORGANISM: Lactobacillus casei

<400> SEQUENCE: 7
atggaaaaat ataagattct ctttcttcat gcaggtgcag aattatatgg tgcagataag     60
attttattgg agatagtaga gaatatagac cgtaaaactt cgagccaat cgttattttg    120 ccggaagacg gtccattggt ttcaaagatg agagaagcag gggccgaagt tagcgtcttg    180
ccatatccga ttcttcggcg aaagtttttc aacatacgag gtatcggtaa ctacatcttt    240
agctatatta ggttctccag acgcttgaaa aaaattgtca ataaagagaa cattagactt    300
gttcacgtca atacgacagc cgttttagaa ggtgtttggc taaaactttt tacaaaggct    360
aaaattgttt ggcatgttca cgaaatcatc atgaagccca atttattta caaactgatt    420 tgttttctca tacagcactt ttctgatcag gcagttgctg tatcagatgc aacaaaacaa    480
agactcattg attccggaat cgttgataag atgaaagtaa ttaccattca taatggtata    540
agtaaagatt acccgcaaaa tgggccggat tatgtgcgaa atctttgag catctctcca    600 gatgcagttg tcattggaat ggttggaaga gtgaacgctt ggaagggcca aggggatttc    660
atagatgctg taggtcccat tttacaaaaa agtcaaaatg ttcatgctct cctcgtgggg    720
agtgcttatc agggagaaga agtttatgag cacaagctgt tcgacaaagt agcttctttg    780
gataccaagg aacgtataca cctctgtccc tttaccgaac agattgctga ttactattcg    840

```
gctttcaaca tttcgtact ccctagcatc cagcctgatc cttttccaac agttgtctta    900
gaggcaatgt caaattcgtt gcctgttgtc gcatatgatc acgggggagc tagtgagatg    960
attgtggaca tgagaccgg ttatctctgc actgctttgg acgtctctga attaagtcgg    1020
aaactagagt tactggttgg agatcgtgca cttcggataa aaatgggaca aaaagccaga    1080
gttcgacaag aagctgagtt cagtttagat caattcgtga acagaatgac aagggtatac    1140
ctcgacctga ttgaatga                                                  1158
```

<210> SEQ ID NO 8
<211> LENGTH: 385
<212> TYPE: PRT
<213> ORGANISM: Lactobacillus casei

<400> SEQUENCE: 8

```
Met Glu Lys Tyr Lys Ile Leu Phe Leu His Ala Gly Ala Glu Leu Tyr
1               5                   10                  15

Gly Ala Asp Lys Ile Leu Leu Glu Ile Val Glu Asn Ile Asp Arg Lys
            20                  25                  30

Thr Phe Glu Pro Ile Val Ile Leu Pro Glu Asp Gly Pro Leu Val Ser
        35                  40                  45

Lys Met Arg Glu Ala Gly Ala Glu Val Ser Val Leu Pro Tyr Pro Ile
    50                  55                  60

Leu Arg Arg Lys Phe Phe Asn Ile Arg Gly Ile Gly Asn Tyr Ile Phe
65                  70                  75                  80

Ser Tyr Ile Arg Phe Ser Arg Arg Leu Lys Lys Ile Val Asn Lys Glu
                85                  90                  95

Asn Ile Arg Leu Val His Val Asn Thr Thr Ala Val Leu Glu Gly Val
            100                 105                 110

Trp Leu Lys Leu Phe Thr Lys Ala Lys Ile Val Trp His Val His Glu
        115                 120                 125

Ile Ile Met Lys Pro Lys Phe Ile Tyr Lys Leu Ile Cys Phe Leu Ile
    130                 135                 140

Gln His Phe Ser Asp Gln Ala Val Ala Val Ser Asp Ala Thr Lys Gln
145                 150                 155                 160

Arg Leu Ile Asp Ser Gly Ile Val Asp Lys Met Lys Val Ile Thr Ile
                165                 170                 175

His Asn Gly Ile Ser Lys Asp Tyr Pro Gln Asn Gly Pro Asp Tyr Val
            180                 185                 190

Arg Lys Ser Leu Ser Ile Ser Pro Asp Ala Val Val Ile Gly Met Val
        195                 200                 205

Gly Arg Val Asn Ala Trp Lys Gly Gln Gly Asp Phe Ile Asp Ala Val
    210                 215                 220

Gly Pro Ile Leu Gln Lys Ser Gln Asn Val His Ala Leu Leu Val Gly
225                 230                 235                 240

Ser Ala Tyr Gln Gly Glu Glu Val Tyr Glu His Lys Leu Phe Asp Lys
                245                 250                 255

Val Ala Ser Leu Asp Thr Lys Glu Arg Ile His Leu Cys Pro Phe Thr
            260                 265                 270

Glu Gln Ile Ala Asp Tyr Tyr Ser Ala Phe Asn Ile Phe Val Leu Pro
        275                 280                 285

Ser Ile Gln Pro Asp Pro Phe Pro Thr Val Leu Glu Ala Met Ser
    290                 295                 300

Asn Ser Leu Pro Val Val Ala Tyr Asp His Gly Gly Ala Ser Glu Met
305                 310                 315                 320
```

-continued

Ile Val Asp Asn Glu Thr Gly Tyr Leu Cys Thr Ala Leu Asp Val Ser
                325                 330                 335

Glu Leu Ser Arg Lys Leu Glu Leu Leu Val Gly Asp Arg Ala Leu Arg
            340                 345                 350

Ile Lys Met Gly Gln Lys Ala Arg Val Arg Gln Glu Ala Glu Phe Ser
            355                 360                 365

Leu Asp Gln Phe Val Asn Arg Met Thr Arg Val Tyr Leu Asp Leu Ile
    370                 375                 380

Glu
385

<210> SEQ ID NO 9
<211> LENGTH: 975
<212> TYPE: DNA
<213> ORGANISM: Lactobacillus casei

<400> SEQUENCE: 9
gtgacagtga atcgaaaaac agacgtctct attattattc cgcccataa tgcagagcct      60 ttcattacaa agtgtctcca aagcatccaa cagcaaagtt ttcacaactt tgaagttcta    120
gttgtagaga atggttcaac ggatcatacc gtcgaaagtg ttttacctttt gtttcgaca    180 gacaaaagga tcagattatt gcaaaattca gatcttggag tcagtaacgc aagaaactta    240
gctttacaga aagctcaatc taaatttgtt acatttgttg atgctgatga ctacatatcg    300
aatactcaca ttcaggtttt gatggatagt gtaaaagata agaagacga catgggtgtt     360 actggatttt cttatgaaac cgaggacggg aaaattttaa agtaatttc cgttttaaat    420 tcaaagatga gtgcagaaga ggcaataaga gctacctatg accttactgg aattcaagga    480
attgtcagca acaagatctt taagaagtca ataatagatc gatacggtat acgatttgat    540
ccctccatct ctaaatatga agaccataag tttgttgtgg cgtatttagt ccattgtcaa    600
caggtttctt gtaagagtga cataacttac cattatatca acatccaga gagttctttg    660 ttcacggtaa agaccagttt gattcaagat ttagatgtct ttttgtcgat tcgaaaaatg    720
attgttaatc atggatttaa ggactttaaa aagtatgtaa atgatccgct acaaaacata    780
gttctaagtc attattggca tccagttgat tctcatgata aaccgaagc tgctaaaagg    840 atggttgata gaaagttttt ctcatacaat ctgctcaata tgtcaatcaa aaataaattg    900
aaatgctttt ttgcttttct ttctttaggt ccgtattgta ttaagcggaa atttcgcaat    960
aatgatgcat catga                                                     975

<210> SEQ ID NO 10
<211> LENGTH: 324
<212> TYPE: PRT
<213> ORGANISM: Lactobacillus casei

<400> SEQUENCE: 10

Met Thr Val Asn Arg Lys Thr Asp Val Ser Ile Ile Pro Ala His
  1               5                  10                  15

Asn Ala Glu Pro Phe Ile Thr Lys Cys Leu Gln Ser Ile Gln Gln Gln
                 20                  25                  30

Ser Phe His Asn Phe Glu Val Leu Val Val Glu Asn Gly Ser Thr Asp
             35                  40                  45

His Thr Val Glu Ser Val Leu Pro Phe Val Ser Thr Asp Lys Arg Ile
         50                  55                  60

Arg Leu Leu Gln Asn Ser Asp Leu Gly Val Ser Asn Ala Arg Asn Leu
 65                  70                  75                  80

```
Ala Leu Gln Lys Ala Gln Ser Lys Phe Val Thr Phe Val Asp Ala Asp
                85                  90                  95

Asp Tyr Ile Ser Asn Thr His Ile Gln Val Leu Met Asp Ser Val Lys
            100                 105                 110

Asp Lys Glu Asp Asp Met Gly Val Thr Gly Phe Ser Tyr Glu Thr Glu
        115                 120                 125

Asp Gly Lys Ile Leu Lys Val Ile Ser Val Leu Asn Ser Lys Met Ser
    130                 135                 140

Ala Glu Glu Ala Ile Arg Ala Thr Tyr Asp Leu Thr Gly Ile Gln Gly
145                 150                 155                 160

Ile Val Ser Asn Lys Ile Phe Lys Lys Ser Ile Asp Arg Tyr Gly
                165                 170                 175

Ile Arg Phe Asp Pro Ser Ile Ser Lys Tyr Glu Asp His Lys Phe Val
            180                 185                 190

Val Ala Tyr Leu Val His Cys Gln Gln Val Ser Cys Lys Ser Asp Ile
        195                 200                 205

Thr Tyr His Tyr Ile Lys His Pro Glu Ser Ser Leu Phe Thr Val Lys
    210                 215                 220

Thr Ser Leu Ile Gln Asp Leu Asp Val Phe Leu Ser Ile Arg Lys Met
225                 230                 235                 240

Ile Val Asn His Gly Phe Lys Asp Phe Lys Lys Tyr Val Asn Asp Pro
                245                 250                 255

Leu Gln Asn Ile Val Leu Ser His Tyr Trp His Pro Val Asp Ser His
            260                 265                 270

Asp Lys Thr Glu Ala Ala Lys Arg Met Val Asp Arg Lys Phe Phe Ser
        275                 280                 285

Tyr Asn Leu Leu Asn Met Ser Ile Lys Asn Lys Leu Lys Cys Phe Phe
    290                 295                 300

Ala Phe Leu Ser Leu Gly Pro Tyr Cys Ile Lys Arg Lys Phe Arg Asn
305                 310                 315                 320

Asn Asp Ala Ser

<210> SEQ ID NO 11
<211> LENGTH: 1260
<212> TYPE: DNA
<213> ORGANISM: Lactobacillus casei

<400> SEQUENCE: 11
gtgttatccg ttaaaatcaa ccttttcttt caaaaagctt tgtatcttat gcttctctta     60
cttcaagtga attttttaa cctatttggt agcccaaatt tttatcaaat gaactcagat    120
aattcgaaag tgcttgttct tttttggtt accatttcgg tttttatttg ggtccctatt    180
gcgataactg ccctttttaa agcaaaagag cggtcaaagc actcgtttaa ttggttgatc    240
attggttttt tgttttgttg ggttgctgtc ctctttggca gttcaagtgt gtatcaaatt    300
agcctaagaa aagcttttaa tttcagttac tactatccga ttgtggcata cttctttcca    360
tttgcctggc tcgttaaaag tgattttct tttgtactca agtcatttaa atttttgca    420 tattttgagc tcttgatttt actgatacaa gatctagttc ttagtttaag tggaaagctt    480
tttcttagtt ttgatccttt tggacaacaa atgtttatgg attctggacg aatcatggcg    540
gggaccgact ttcttttgtt ggcctgtttc attattgtt tagccagaaa acttaaacac    600
acgcttccgt catatctaga agttttgttt ttttagggt tagtctttca cttgctcttt    660
ttcacaaaga gtagaatgct cctcctactt gtgatagcta tttaagtgt agctattttc    720 tttaactcct ccaaaggctt cacaatacct gttcgtttga tcttctatat tttttgtttt    780
```

```
gttggtcttc tagcgttgat gaatgtattg atcgccaaga tgaattttt ctccggcgac      840 agagcggcca gtggacaagt tagacttcag gcgattgctt attatctaaa caatcttgga      900
attaataaat ggtttggttt tggatttacc ccatactctg atcaaattgg tggaggcggc      960
caaggcgtag atggcggcgt ttttacacc agtgatgttg gtatgatcgg cttcattgca     1020
atctttggag ctctcggagt gcttttgct attttattct tatcaagttt tgttcgattt     1080
ttacgcacct ttggtgactt ttctgctaaa ttgattgtaa ttgtatacat ttttggccag     1140
tggatttcac tctcatcgtt tgatatcagt agaatttga ttttccctat tgctctgggt     1200
tttctgatag gctttaagga atttctcaat tctagagaga acgtattaga tgatagttaa     1260
```

<210> SEQ ID NO 12
<211> LENGTH: 419
<212> TYPE: PRT
<213> ORGANISM: Lactobacillus casei

<400> SEQUENCE: 12

```
Met Leu Ser Val Lys Ile Asn Leu Phe Phe Gln Lys Ala Leu Tyr Leu
 1               5                  10                  15

Met Leu Leu Leu Leu Gln Val Asn Phe Phe Asn Leu Phe Gly Ser Pro
             20                  25                  30

Asn Phe Tyr Gln Met Asn Ser Asp Asn Ser Lys Val Leu Val Leu Phe
         35                  40                  45

Leu Val Thr Ile Ser Val Phe Ile Trp Val Pro Ile Ala Ile Thr Ala
     50                  55                  60

Leu Phe Lys Ala Lys Glu Arg Ser Lys His Ser Phe Asn Trp Leu Ile
 65                  70                  75                  80

Ile Gly Phe Leu Phe Cys Trp Val Ala Val Leu Phe Gly Ser Ser Ser
                 85                  90                  95

Val Tyr Gln Ile Ser Leu Arg Lys Ala Phe Asn Phe Ser Tyr Tyr Tyr
            100                 105                 110

Pro Ile Val Ala Tyr Phe Phe Pro Phe Ala Trp Leu Val Lys Ser Asp
        115                 120                 125

Phe Ser Phe Val Leu Lys Ser Phe Lys Phe Phe Ala Tyr Phe Glu Leu
    130                 135                 140

Leu Ile Leu Leu Ile Gln Asp Leu Val Leu Ser Leu Ser Gly Lys Leu
145                 150                 155                 160

Phe Leu Ser Phe Asp Pro Phe Gly Gln Gln Met Phe Met Asp Ser Gly
                165                 170                 175

Arg Ile Met Ala Gly Thr Asp Phe Leu Leu Ala Cys Phe Ile Ile
            180                 185                 190

Val Leu Ala Arg Lys Leu Lys His Thr Leu Pro Ser Tyr Leu Glu Val
        195                 200                 205

Leu Phe Phe Leu Gly Leu Val Phe His Leu Leu Phe Phe Thr Lys Ser
    210                 215                 220

Arg Met Leu Leu Leu Leu Val Ile Ala Ile Leu Ser Val Ala Ile Phe
225                 230                 235                 240

Phe Asn Ser Ser Lys Gly Phe Thr Ile Pro Val Arg Leu Ile Phe Tyr
                245                 250                 255

Ile Phe Cys Phe Val Gly Leu Leu Ala Leu Met Asn Val Leu Ile Ala
            260                 265                 270

Lys Met Asn Phe Phe Ser Gly Asp Arg Ala Ala Ser Gly Gln Val Arg
        275                 280                 285

Leu Gln Ala Ile Ala Tyr Tyr Leu Asn Asn Leu Gly Ile Asn Lys Trp
    290                 295                 300
```

```
Phe Gly Phe Gly Phe Thr Pro Tyr Ser Asp Gln Ile Gly Gly Gly
305                 310                 315                 320

Gln Gly Val Asp Gly Val Phe Tyr Thr Ser Asp Val Gly Met Ile
            325                 330                 335

Gly Phe Ile Ala Ile Phe Gly Ala Leu Gly Val Leu Phe Ala Ile Leu
        340                 345                 350

Phe Leu Ser Ser Phe Val Arg Phe Leu Arg Thr Phe Gly Asp Phe Ser
        355                 360                 365

Ala Lys Leu Ile Val Ile Val Tyr Ile Phe Gly Gln Trp Ile Ser Leu
    370                 375                 380

Ser Ser Phe Asp Ile Ser Arg Ile Leu Ile Phe Pro Ile Ala Leu Gly
385                 390                 395                 400

Phe Leu Ile Gly Phe Lys Glu Phe Leu Asn Ser Arg Glu Asn Val Leu
                405                 410                 415

Asp Asp Ser

<210> SEQ ID NO 13
<211> LENGTH: 666
<212> TYPE: DNA
<213> ORGANISM: Lactobacillus casei

<400> SEQUENCE: 13
atgccaacaa cttctgattc cctagcgatt cttgacaaaa ttcaaattta ttttcggct       60
ttgtttaaag tgattcgtgg ctttttattg tctgtgacaa cgcgccatgc aaagccacta      120
atattttgg gacgacacgt taaaatcatg aatcggcagt atttacacat agaagcaaaa       180
gtaaagtttg aggattattg tgagattcaa ggactatcaa caatggact ttattttgcg       240
aaagacgtca ctatcggccg gggggttcaa attagacctt ctagctatta cggcgtaggc      300
catattggct atggatttag tattggagag aatagttcag ttgggccagg tggattcatt      360
ggatgtgctg gtaaggttca aatcaataag aacgtaatga ttggcccaaa tgttacgatt      420
attgcagaaa atcatcattt tcacagtaca aataaatcaa taaagatca aggtgtttat       480
caaaaaggaa tagtaatcca tgatgatgtt tggattggag caaatgttac tattttagac      540
ggtgtaacaa tttgcagtgg agcagttatt ggtgctggtg caattattac aaaggatgtg      600
ccagctaata caattttggt tgataagtta aacccaattt tgagaagccg aattgcccac      660
agttag                                                                 666

<210> SEQ ID NO 14
<211> LENGTH: 221
<212> TYPE: PRT
<213> ORGANISM: Lactobacillus casei

<400> SEQUENCE: 14

Met Pro Thr Thr Ser Asp Ser Leu Ala Ile Leu Asp Lys Ile Gln Ile
1               5                   10                  15

Tyr Phe Ser Ala Leu Phe Lys Val Ile Arg Gly Phe Leu Leu Ser Val
            20                  25                  30

Thr Thr Arg His Ala Lys Pro Leu Ile Phe Leu Gly Arg His Val Lys
        35                  40                  45

Ile Met Asn Arg Gln Tyr Leu His Ile Glu Ala Lys Val Lys Phe Glu
    50                  55                  60

Asp Tyr Cys Glu Ile Gln Gly Leu Ser Thr Asn Gly Leu Tyr Phe Ala
65                  70                  75                  80

Lys Asp Val Thr Ile Gly Arg Gly Val Gln Ile Arg Pro Ser Ser Tyr
                85                  90                  95
```

```
Tyr Gly Val Gly His Ile Gly Tyr Gly Phe Ser Ile Gly Glu Asn Ser
            100                 105                 110

Ser Val Gly Pro Gly Phe Ile Gly Cys Ala Gly Lys Val Gln Ile
        115                 120                 125

Asn Lys Asn Val Met Ile Gly Pro Asn Val Thr Ile Ala Glu Asn
130                 135                 140

His His Phe His Ser Thr Asn Lys Ser Ile Lys Asp Gln Gly Val Tyr
145                 150                 155                 160

Gln Lys Gly Ile Val Ile His Asp Asp Val Trp Ile Gly Ala Asn Val
                165                 170                 175

Thr Ile Leu Asp Gly Val Thr Ile Cys Ser Gly Ala Val Ile Gly Ala
            180                 185                 190

Gly Ala Ile Ile Thr Lys Asp Val Pro Ala Asn Thr Ile Leu Val Asp
        195                 200                 205

Lys Leu Asn Pro Ile Leu Arg Ser Arg Ile Ala His Ser
210                 215                 220

<210> SEQ ID NO 15
<211> LENGTH: 717
<212> TYPE: DNA
<213> ORGANISM: Lactobacillus casei

<400> SEQUENCE: 15
ttggggatcg tttctgcccc attttggcaa tgtattggag gggtgaattt ggagacaaca      60
tctagtcgtg aacaagttaa tgccgagcag gttgacttg ggggttgac gccgagctac     120 atattctcga agcgttgctt tgattttttg gctagtctag ttgggctgat cttacttagt    180
ggtgtatttc tgatcattgg aatcttaatt aaagttgatg atccacatgg aaagatattc    240
tattcgcaga cccggcttgg taaaaatggc cgagagtttc agatgtggaa gtttcgatcg    300
atggtgagtg cgcctgacaa gatggttgat aagttgcttc gacgtaatga ggtccaaggt    360
gccatgttta agattaagaa tgatcctcgt attacacgtg ttggtcgtgt tcttcggaag    420
tatagtcttg acgagttacc tcagctttat aatgtcttgg tcggggatat gagtttggtt    480
gggcctcgac caccgctacc tagagaagtt gttaagtata ccgattacga tcttcagcga    540
cttgccgtta ttccgggctg tacaggtttg tggcaagtct cgggtcgaaa tgagcttggc    600
ttttctgaga tggttgcgtt ggacattcat tatatcaaca gtgcgtcttt ctttggagat    660
ctcaagattc ttatgaaaac ggtaatggtt gtgattcatc cgactggtgc ctattga      717

<210> SEQ ID NO 16
<211> LENGTH: 238
<212> TYPE: PRT
<213> ORGANISM: Lactobacillus casei

<400> SEQUENCE: 16

Met Gly Ile Val Ser Ala Pro Phe Trp Gln Cys Ile Gly Gly Val Asn
1               5                   10                  15

Leu Glu Thr Thr Ser Ser Arg Glu Gln Val Asn Ala Glu Gln Val Asp
            20                  25                  30

Leu Gly Gly Leu Thr Pro Ser Tyr Ile Phe Ser Lys Arg Cys Phe Asp
        35                  40                  45

Phe Leu Ala Ser Leu Val Gly Leu Ile Leu Ser Gly Val Phe Leu
50                  55                  60

Ile Ile Gly Ile Leu Ile Lys Val Asp Asp Pro His Gly Lys Ile Phe
65                  70                  75                  80
```

```
Tyr Ser Gln Thr Arg Leu Gly Lys Asn Gly Arg Glu Phe Gln Met Trp
                85                  90                  95
Lys Phe Arg Ser Met Val Ser Gly Ala Asp Lys Met Val Asp Lys Leu
            100                 105                 110
Leu Arg Arg Asn Glu Val Gln Gly Ala Met Phe Lys Ile Lys Asn Asp
        115                 120                 125
Pro Arg Ile Thr Arg Val Gly Arg Val Leu Arg Lys Tyr Ser Leu Asp
    130                 135                 140
Glu Leu Pro Gln Leu Tyr Asn Val Leu Val Gly Asp Met Ser Leu Val
145                 150                 155                 160
Gly Pro Arg Pro Leu Pro Arg Glu Val Val Lys Tyr Thr Asp Tyr
                165                 170                 175
Asp Leu Gln Arg Leu Ala Val Ile Pro Gly Cys Thr Gly Leu Trp Gln
            180                 185                 190
Val Ser Gly Arg Asn Glu Leu Gly Phe Ser Glu Met Val Ala Leu Asp
        195                 200                 205
Ile His Tyr Ile Asn Ser Ala Ser Phe Phe Gly Asp Leu Lys Ile Leu
    210                 215                 220
Met Lys Thr Val Met Val Val Ile His Pro Thr Gly Ala Tyr
225                 230                 235

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgggatccga gccaaaacat gttgttgct                                     29

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aactgcagtg ttacgacaac aaccccgt                                      28

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgggatccga cacttcgctg ttggtcaa                                      28

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 20
aactgcaggg tttggtctgt aagctctc                                    28

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aactgcaggc taaaattgtt tggcatgttc                                  30

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cgggatccca caatcatctc actagctcc                                   29

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgggatccgt ggcatacttc tttccattt                                   29

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aactgcagga gagctccaaa gattgcaa                                    28

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgggatccgt ggcatacttc tttccattt                                   29

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 26
aactgcagga gagctccaaa gattgcaa                                              28

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgggatccat catgaatcgg cagtattta                                             29

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aactgcagac cgtctaaaat agtaacattt                                            30

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgggatccgc cgagctacat attctcga                                              28

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aactgcagtc caacgcaacc atctcaga                                              28

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cgggatcctg ggctcagtgg ttgctt                                                26

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 32
aactgcaggg tttgaatggc catcatc                                           27

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atactgcaga ttggcatggg ttttc                                             25

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
taagaattca gcttcgtatt ttggtaca                                          28

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gaagaattca atatgcagga ttta                                              24

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atatctagat tcccccaacc atact                                             25

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cgggatccta gggggaatct atcgtgac                                          28

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 38
gcggtacctc caaaaccaaa aggatttgg                                        29

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcggtaccct gacctgaact aatctgct                                         28

<210> SEQ ID NO 40
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ttctgcagga gaatcttata tttttccatc g                                     31

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
acatctagac ttgttcacgt caatacga                                         28

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ctcatcgatt atgggcggga ataataat                                         28

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tagatcgata cggtatacga t                                                21

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 44
tatctgcagg ccaacaaaag aaagtcg                                            27

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
agactgcaga cgattatctg ttgtct                                             26

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
atagaattca cccctccaat acattg                                             26

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
taagaattct gagatggttg cgttgg                                             26

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
taatctagat aggctttatt cacatcg                                            27

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
taacccgggt ggacttgatt acacaagc                                           28

<210> SEQ ID NO 50
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 50
taactgcaga cactctttt acactgcg                                           28

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tcccccgggt tgggggaatc tatcg                                             25

<210> SEQ ID NO 52
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aaactgcagt tatattttcc atcgataaa                                         29

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gcggatccgc agttgggcca ctttc                                             25

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ttctgcagtt agatgggact gttcaggaa                                         29

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gcggatccga cgaggtgatt gtgg                                              24

<210> SEQ ID NO 56
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
```

-continued

```
<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gcggatccga acttgctgtc aataagc                                        27

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ttctgcagtt agattggcca agccattg                                       28

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gcggatccgc ggggtataca tttc                                           24

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ttctgcagtt ataagccttt tacccc                                         26

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccggtaccgt tagtactgtg gttaacgg                                       28

<210> SEQ ID NO 62
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
```

SEQ ID NO 56 sequence (continued from previous page):

ttctgcagtt agcggtaata catcaattt                                       29

```
<400> SEQUENCE: 62
gcgaattctt acttgatagc agccttatc                                       29

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ccggtaccgt actaggaccg acaggcg                                         27

<210> SEQ ID NO 64
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gcgaattctt aaccaatcaa aacttcaaca ac                                   32

<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cgctgcagtc gccaaatgaa tcattgg                                         27

<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gcggatcctt aatacccaa catagc                                           26

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cgggatccga tcggcgaatt gcggtt                                          26

<210> SEQ ID NO 68
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 68
aactgcagca cgacctgatg caccat                                              26

<210> SEQ ID NO 69
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cgggatccgg tcgcaagatt ggctttg                                             27

<210> SEQ ID NO 70
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aactgcagcc gcaatcgaga ctgcat                                              26

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cgggatcctg gctgctggtg gctttt                                              26

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
aactgcagcc ataacagcat ccctaga                                             27

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
aataagcttt tagcagcggg tgac                                                24

<210> SEQ ID NO 74
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 74
attgctagca tcaggagact cgagac                                              26

<210> SEQ ID NO 75
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cgggatccgc ggcttatatg cgagaaa                                             27

<210> SEQ ID NO 76
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
aactgcagta acacaaatag actcaggg                                            28

<210> SEQ ID NO 77
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ttactgcagc aaatcaaaca gttaca                                              26

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
taatctagac cattgacggc cagc                                                24

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cgcgaattcc tgattcaaac aactccatgg                                          30

<210> SEQ ID NO 80
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 80

```
cgggatcctt actgatcaaa gttgttaatg cc                              32
```

<210> SEQ ID NO 81
<211> LENGTH: 1452
<212> TYPE: DNA
<213> ORGANISM: Lactobacillus casei

<400> SEQUENCE: 81

```
ttgaaaatcg gcttgcgat tgataccatt gacgaagcta gtttgtcctt acatactatg     60
gaagcgaacg gagtcaagat gaaaaaaatg gaaatcagta agtttgaacg atactttctt   120
tatatactgt tctttgaatt gtttgctggg gtggtggtc gtctgcttgc agttgggcca   180
ctttcgattc ggcaaatttt atttgctgga ttgattatta tatttgctat cagatttgtg   240
gtgagtccag atactaggcg tgagatttgg caatacttcc gccaccccaa tacggctgtg   300
ttttggttat cgttgctgat gacagcatgg atattcgtat ctagtttcat gggattata   360
catgggcatg gagccggacc agttgcaact gatttcttcc gggtcattta tgtcatttta   420
attattccat ttatttatta tgttggagag catcgttttt cagttaatga tttagttcgg   480
tgcttatttg tcgccgccgg tgtcgtagca atactgacag ttttcattag tttgacgggc   540
aagtttattg atgacgcaac tttccacgac ttttatgaat ggattaatgg tctcatgcca   600
ggcgatcttt tcttcaggcc ttcacgaggg gtcttctaca agtcagattt ctggtcatg   660
tttactgtta ttatcggctt gattaaactt gctgagaaaa agatcagttt gggcgaaggt   720
attgtcctaa tattgggttc attatctatc attctatcgg agactcgtgg cctttatctg   780
ggaatttttgg tcgggatcgg cacctacatt gcagtgaaag tcgtcatcta tttctggggt   840
gatcgatatt ccttaaactt gaacagagca atgaatatac gacgagcgct tgttttattg   900
gttactgtag ctctatgcgg ctttttttac accaatgcaa cgattgcacg atttagtaag   960
ccttcacccct ctgatatcag acaggaggat cgcctgaaaa agcaagatcg aaatatttct  1020
ggcgacgaca tcagtctgag ctcacgattt gtcttattat cggatgcaat ggacattgtt  1080
aaaagcgaat ctgcagttgg agttgttgtg ggtaatggct atggaacaac aattggcaat  1140
accaagattg gtattgaaat gagctttgtg gacattcttg ttgaacaagg tgccatggga  1200
cttgttcttt ggctagcgtt tgcactttta ccccttact atttcttcag aagtttcctt  1260
ttgagcagac aactggctga tatttacatt ggcctattgg gtagttcgct atccatgatt  1320
ttggtgacga acattaaccc ctttcctgaac agtcccatcg gattaggctt cttgttgccg  1380
gtcattgtga ttgcgtacaa agcatttata agcgccagga cgaaaaacca acccgctatt  1440
aaaattagtt aa                                                       1452
```

<210> SEQ ID NO 82
<211> LENGTH: 483
<212> TYPE: PRT
<213> ORGANISM: Lactobacillus casei

<400> SEQUENCE: 82

```
Met Lys Ile Gly Leu Ala Ile Asp Thr Ile Asp Glu Ala Ser Leu Ser
1               5                   10                  15

Leu His Thr Met Glu Ala Asn Gly Val Lys Met Lys Lys Met Glu Ile
            20                  25                  30

Ser Lys Phe Glu Arg Tyr Phe Leu Tyr Ile Leu Phe Glu Leu Phe
        35                  40                  45
```

```
Ala Gly Gly Gly Gly Arg Leu Leu Ala Val Gly Pro Leu Ser Ile Arg
 50                  55                  60
Gln Ile Leu Phe Ala Gly Leu Ile Ile Ile Phe Ala Ile Arg Phe Val
 65                  70                  75                  80
Val Ser Pro Asp Thr Arg Arg Glu Ile Trp Gln Tyr Phe Arg His Pro
                 85                  90                  95
Asn Thr Ala Val Phe Trp Leu Ser Leu Leu Met Thr Ala Trp Ile Phe
            100                 105                 110
Val Ser Ser Phe Ile Gly Ile Ile His Gly His Gly Ala Gly Pro Val
        115                 120                 125
Ala Thr Asp Phe Phe Arg Val Ile Tyr Val Ile Leu Ile Ile Pro Phe
130                 135                 140
Ile Tyr Tyr Val Gly Glu His Arg Phe Ser Val Asn Asp Leu Val Arg
145                 150                 155                 160
Cys Leu Phe Val Ala Ala Gly Val Val Ala Ile Leu Thr Val Phe Ile
                165                 170                 175
Ser Leu Thr Gly Lys Phe Ile Asp Asp Ala Thr Phe His Asp Phe Tyr
            180                 185                 190
Glu Trp Ile Asn Gly Leu Met Pro Gly Asp Leu Phe Phe Arg Pro Ser
        195                 200                 205
Arg Gly Val Phe Tyr Lys Ser Asp Phe Leu Val Met Phe Thr Val Ile
210                 215                 220
Ile Gly Leu Ile Lys Leu Ala Glu Lys Lys Ile Ser Leu Gly Glu Gly
225                 230                 235                 240
Ile Val Leu Ile Leu Gly Ser Leu Ser Ile Ile Leu Ser Glu Thr Arg
                245                 250                 255
Gly Leu Tyr Leu Gly Ile Leu Val Gly Ile Gly Thr Tyr Ile Ala Val
            260                 265                 270
Lys Val Val Ile Tyr Phe Trp Gly Asp Arg Tyr Ser Leu Asn Leu Asn
        275                 280                 285
Arg Ala Met Asn Ile Arg Arg Ala Leu Val Leu Leu Val Thr Val Ala
290                 295                 300
Leu Cys Gly Phe Phe Tyr Thr Asn Ala Thr Ile Ala Arg Phe Ser Lys
305                 310                 315                 320
Pro Ser Pro Ser Asp Ile Arg Gln Glu Asp Arg Leu Lys Lys Gln Asp
                325                 330                 335
Arg Asn Ile Ser Gly Asp Asp Ile Ser Leu Ser Ser Arg Phe Val Leu
            340                 345                 350
Leu Ser Asp Ala Met Asp Ile Val Lys Ser Glu Ser Ala Val Gly Val
        355                 360                 365
Val Val Gly Asn Gly Tyr Gly Thr Thr Ile Gly Asn Thr Lys Ile Gly
370                 375                 380
Ile Glu Met Ser Phe Val Asp Ile Leu Val Glu Gln Gly Ala Met Gly
385                 390                 395                 400
Leu Val Leu Trp Leu Ala Phe Ala Leu Leu Pro Leu Tyr Tyr Phe Phe
                405                 410                 415
Arg Ser Phe Leu Leu Ser Arg Gln Leu Ala Asp Ile Tyr Ile Gly Leu
            420                 425                 430
Leu Gly Ser Ser Leu Ser Met Ile Leu Val Thr Asn Ile Asn Pro Phe
        435                 440                 445
Leu Asn Ser Pro Ile Gly Leu Gly Phe Leu Leu Pro Val Ile Val Ile
450                 455                 460
```

Ala Tyr Lys Ala Phe Ile Ser Ala Arg Thr Lys Asn Gln Pro Ala Ile
465                 470                 475                 480

Lys Ile Ser

<210> SEQ ID NO 83
<211> LENGTH: 747
<212> TYPE: DNA
<213> ORGANISM: Lactobacillus casei

<400> SEQUENCE: 83

```
atggcccaag ctgaaagtga tgcttcaagt agtcggagga aaaacatcat gatgatttca      60
gtttgcatgg caacatacaa tggagcccgg tttgttggtg cccagctcaa atcaatcctt     120
gatcagcttg ggtctaatga cgaggtgatt gtggttgatg atcactcgac tgatgagact     180
gtcgctgtca tcgatcaatt taaagattca cgcattaagt tgatcgaaaa cacgactaat     240
cacggcccaa tttatggctt tatgaccgcg ttgaattatg ctaaaggtga ttatcttttt     300
ttatctgacc aagatgatgt tggtgtccc aacaaggtta ctcgcgtcat gacagctttt     360
gagaaggaaa aggcagtcgt tgttgtccat gacggtatcg tcactgatca gtcgcttagt     420
cgggttgacg attcttggaa tcatttcagt catagagtac cgagtcagtc catgattaaa     480
acactaatca gaatggata caccggtgct atgatggcct tagtcgcga acttttgcca     540
ctcattcttc cttttcccaa gcaggtgcca atgcacgact ggtggattgc tttggtagcc     600
atgaaacacc acatgaagat tgtcgttttg ccagataaat tgatgtatta ccggcgtcat     660
gccggtaatg tgacgggtag ccatcgcaaa ctgcatgaaa tgatggcgtt tcgtttcaat     720
atgttacgac tttttattcg cgcttaa                                          747
```

<210> SEQ ID NO 84
<211> LENGTH: 248
<212> TYPE: PRT
<213> ORGANISM: Lactobacillus casei

<400> SEQUENCE: 84

Met Ala Gln Ala Glu Ser Asp Ala Ser Ser Arg Arg Lys Asn Ile
1               5                   10                  15

Met Met Ile Ser Val Cys Met Ala Thr Tyr Asn Gly Ala Arg Phe Val
                20                  25                  30

Gly Ala Gln Leu Lys Ser Ile Leu Asp Gln Leu Gly Ser Asn Asp Glu
            35                  40                  45

Val Ile Val Val Asp Asp His Ser Thr Asp Glu Thr Val Ala Val Ile
        50                  55                  60

Asp Gln Phe Lys Asp Ser Arg Ile Lys Leu Ile Glu Asn Thr Thr Asn
65                  70                  75                  80

His Gly Pro Ile Tyr Gly Phe Met Thr Ala Leu Asn Tyr Ala Lys Gly
                85                  90                  95

Asp Tyr Leu Phe Leu Ser Asp Gln Asp Asp Val Trp Cys Pro Asn Lys
            100                 105                 110

Val Thr Arg Val Met Thr Ala Phe Glu Lys Glu Lys Ala Val Val Val
        115                 120                 125

Val His Asp Gly Ile Val Thr Asp Gln Ser Leu Ser Arg Val Asp Asp
    130                 135                 140

Ser Trp Asn His Phe Ser His Arg Val Pro Ser Gln Ser Met Ile Lys
145                 150                 155                 160

Thr Leu Ile Lys Asn Gly Tyr Thr Gly Ala Met Met Ala Phe Ser Arg
                165                 170                 175

```
Glu Leu Leu Pro Leu Ile Leu Pro Phe Pro Lys Gln Val Pro Met His
                180                 185                 190

Asp Trp Trp Ile Ala Leu Val Ala Met Lys His Met Lys Ile Val
            195                 200                 205

Val Leu Pro Asp Lys Leu Met Tyr Tyr Arg Arg His Ala Gly Asn Val
        210                 215                 220

Thr Gly Ser His Arg Lys Leu His Glu Met Met Ala Phe Arg Phe Asn
225                 230                 235                 240

Met Leu Arg Leu Phe Ile Arg Ala
                245

<210> SEQ ID NO 85
<211> LENGTH: 885
<212> TYPE: DNA
<213> ORGANISM: Lactobacillus casei

<400> SEQUENCE: 85
atggtcaaag tttcaatcat tattcctgct tacaatgctg ctaccactct aaagcgcgct      60
gttcagtctg tccgtaaaca aaccttgaac gattttgaaa tattaatcgt caataatgga     120
tcgacggatc agacagcagc agttatgtca caccttgtcc aagctgaccc tcggatacac     180
attctgcaaa gtatgaaagg cgcagccgc gctcgtaatc aaggactgac aaaggctcaa     240
ggtactttta tccagtttct ggacgcggat gacgaacttg ctgtcaataa gctggaagtg     300
ggcagcagtt atttgacgaa tcatccaaac agtagcgcat acatcacggc ggctaaatat     360
caaaatgata gcgtggcga tgagagcatt cgccagattc cgctaacatc cgcagcacct      420
ttattaaagg caaattattt gccaatgagt gcaccgcttg tgaggaaaag tgcgctcata     480 aagccctta gagaagatct tgaatataat gaggactggt tattttgggc tgaaaacctg     540
tacaaaaaag atagctgt tagctcgaca gttggcacaa cgatccatat acgtctgct      600 aatactatga ctcagtttga tcgaatgcaa atgtacgagt gttatgtgcg gggaatttta     660
aaagaagaat tttcggcacg cggtcctcgc tactgggcgc gggatatgcg ctatgcactc     720
aattatctac ttagcgcgtc ggatgcaacg agcgaggacc tgaagctatc taagacaatg     780
gcttggccaa tccggtttag ccgtctatta ttagctgtgc accgttgcg agcggttatt      840 acaaaaaaac gtaatgccgt gaaagcgcgt agtcaatatg gataa                     885

<210> SEQ ID NO 86
<211> LENGTH: 294
<212> TYPE: PRT
<213> ORGANISM: Lactobacillus casei

<400> SEQUENCE: 86

Met Val Lys Val Ser Ile Ile Ile Pro Ala Tyr Asn Ala Ala Thr Thr
1               5                   10                  15

Leu Lys Arg Ala Val Gln Ser Val Arg Lys Gln Thr Leu Asn Asp Phe
                20                  25                  30

Glu Ile Leu Ile Val Asn Asn Gly Ser Thr Asp Gln Thr Ala Ala Val
            35                  40                  45

Met Ser His Leu Val Gln Ala Asp Pro Arg Ile His Ile Leu Gln Ser
        50                  55                  60

Met Lys Gly Arg Ser Arg Ala Arg Asn Gln Gly Leu Thr Lys Ala Gln
65                  70                  75                  80

Gly Thr Phe Ile Gln Phe Leu Asp Ala Asp Asp Glu Leu Ala Val Asn
                85                  90                  95
```

```
Lys Leu Glu Val Gly Ser Ser Tyr Leu Thr Asn His Pro Asn Ser Ser
                100                 105                 110

Ala Tyr Ile Thr Ala Ala Lys Tyr Gln Asn Asp Lys Arg Gly Asp Glu
            115                 120                 125

Ser Ile Arg Gln Ile Pro Leu Thr Ser Ala Ala Pro Leu Leu Lys Ala
    130                 135                 140

Asn Tyr Leu Pro Met Ser Ala Pro Leu Val Arg Lys Ser Ala Leu Ile
145                 150                 155                 160

Lys Pro Phe Arg Glu Asp Leu Glu Tyr Asn Glu Asp Trp Leu Phe Trp
                165                 170                 175

Ala Glu Asn Leu Tyr Lys Lys Glu Ile Ala Val Ser Ser Thr Val Gly
            180                 185                 190

Thr Thr Ile His Ile Thr Ser Ala Asn Thr Met Thr Gln Phe Asp Arg
        195                 200                 205

Met Gln Met Tyr Glu Cys Tyr Val Arg Gly Ile Leu Lys Glu Glu Phe
    210                 215                 220

Ser Ala Arg Gly Pro Arg Tyr Trp Ala Arg Asp Met Arg Tyr Ala Leu
225                 230                 235                 240

Asn Tyr Leu Leu Ser Ala Ser Asp Ala Thr Ser Glu Asp Leu Lys Leu
                245                 250                 255

Ser Lys Thr Met Ala Trp Pro Ile Arg Phe Ser Arg Leu Leu Leu Ala
            260                 265                 270

Val Pro Pro Leu Arg Ala Val Ile Thr Lys Lys Arg Asn Ala Val Lys
        275                 280                 285

Ala Arg Ser Gln Tyr Gly
    290

<210> SEQ ID NO 87
<211> LENGTH: 774
<212> TYPE: DNA
<213> ORGANISM: Lactobacillus casei

<400> SEQUENCE: 87
ttgataccaa aaattattca ttatgtttgg attggcggtg cgaagcccga ttcggtgcaa      60
aaaaacattg ataattggaa gaaagtatta gcggggtata catttcaaga gtggaacgaa     120
cataattggg atatctcgaa gaaccagttc gcgaagtatt tctacgataa aaagcaattt     180
gcattcgttg gagatgccat ccgagttgat gtgttaaacc gaattggtgg aatctattta     240
gatacagatg ttgaagttta taagcctttt aattctttgc taaggaaaca actagttttt     300
ggtcgaattt ataataatgc gataggaaca gctaccattt ggctgaaaa gaatactcgg      360 atgatgaacg atttgtcgaa tatgtataaa gcatttgatt tgacacaatt agaggataat     420
accatcgaca agttaataa tggcattttt acaagatacc ttcttgataa acacgtcggc      480
ttttcctttg caataccaa acaacgattg aaaaatggcg cgctcatctt acccaagcaa      540
tattttgaag tgccagcaat gtggtttgaa accggcacat tgccacgca tcacgtggcg     600 ggcagttggc aagataaaaa gcaggagagt aacaacgagt caaagggct taagtctggg      660 gtaaaaggct taattcgttc agcttttccg gctgctattg ctcgatacga gaatcttaag      720
ggcggccaaa gtaatagtat cgcaaaagaa tttggaccta aagcgcctca gtga            774

<210> SEQ ID NO 88
<211> LENGTH: 257
<212> TYPE: PRT
<213> ORGANISM: Lactobacillus casei
```

-continued

<400> SEQUENCE: 88

Met Ile Pro Lys Ile Ile His Tyr Val Trp Ile Gly Gly Ala Lys Pro
1               5                   10                  15

Asp Ser Val Gln Lys Asn Ile Asp Asn Trp Lys Lys Val Leu Ala Gly
            20                  25                  30

Tyr Thr Phe Gln Glu Trp Asn Glu His Asn Trp Asp Ile Ser Lys Asn
        35                  40                  45

Gln Phe Ala Lys Tyr Phe Tyr Asp Lys Lys Gln Phe Ala Phe Val Gly
    50                  55                  60

Asp Ala Ile Arg Val Asp Val Leu Asn Arg Ile Gly Gly Ile Tyr Leu
65                  70                  75                  80

Asp Thr Asp Val Glu Val Tyr Lys Pro Phe Asn Ser Leu Leu Lys Glu
                85                  90                  95

Gln Leu Val Phe Gly Arg Ile Tyr Asn Asn Ala Ile Gly Thr Ala Thr
            100                 105                 110

Ile Leu Ala Glu Lys Asn Thr Arg Met Met Asn Asp Leu Ser Asn Met
        115                 120                 125

Tyr Lys Ala Phe Asp Leu Thr Gln Leu Glu Asp Asn Thr Ile Asp Lys
    130                 135                 140

Val Asn Asn Gly Ile Phe Thr Arg Tyr Leu Leu Asp Lys His Val Gly
145                 150                 155                 160

Phe Ser Phe Gly Asn Thr Lys Gln Arg Leu Lys Asn Gly Ala Leu Ile
                165                 170                 175

Leu Pro Lys Gln Tyr Phe Glu Val Pro Ala Met Trp Phe Glu Thr Gly
            180                 185                 190

Thr Phe Ala Thr His His Val Ala Gly Ser Trp Gln Asp Lys Lys Gln
        195                 200                 205

Glu Ser Asn Asn Glu Ser Lys Gly Leu Lys Ser Gly Val Lys Gly Leu
    210                 215                 220

Ile Arg Ser Ala Phe Pro Ala Ala Ile Ala Arg Tyr Glu Asn Leu Lys
225                 230                 235                 240

Gly Gly Gln Ser Asn Ser Ile Ala Lys Glu Phe Gly Pro Lys Ala Pro
                245                 250                 255

Gln

<210> SEQ ID NO 89
<211> LENGTH: 2766
<212> TYPE: DNA
<213> ORGANISM: Lactobacillus casei

<400> SEQUENCE: 89
atgaaattga gtaaacattt caagttaatc atgacggggg cttttctctt ggcctcagtc      60
ggcttgtttg caccgattgt attggggcaa gggcaacgag tctatgcagg tacgtccagc     120
accgttagta ctgtggttaa cggttctgat gaacaagact tcatctcac aaatcagcat      180 tcgaatcttg ataccgataa tcacgttctg ggcggtggtc aggcggcacc tgctttgcgc     240
acaaagcgaa gtattatgag caatggttta caagcgaata gcattcaaac atattcacaa     300
actgttatga gtttcacaat tggagattca cgagtgccgc gagtcgatac cgtcgatgtg     360
gcctcttatc aaaatgggat gacccaagct aattacaatt ccctcagaac ctcgggagtt     420
aaagcggtta ttgtgaagtc ttctgaagga tcaacttacc ggaatccata tgcggcaaaa     480
caacttgctc aagcgaaggc tgctggactc aaaacggcag tatatcacta cgttcatttt     540
gcaaatcaat ctgatgccat tgctgaagct aattactttg cgaacacttt ggacagtctt     600

```
ggtttcagca aaaccagtgc agtggttgct gatattgagg atagtgatgt tggcggtgat    660
gtcgcagcca atgtcaacgc tttttggaac gtactgagta cccgtggtta tgttaatcat    720
attgtctata cagggcttta ttactcatat tccaaagcag caatttcaac agttggtaat    780
gagcgttcct gggtcgctca gtatccatat gttccaagtg cgaacaatct tctgaatacc    840
ggctatggtg catggcaatt ttcatctatg gcaggcatcc ccaactataa tggtcgcgtg    900
gatgtctcta ttgattatca aggcattttt acgagtgcat tttcttttga ccacgttatt    960
gatagtcact cacttagcgg tgtgaaacag attgatgaaa ccaatcgtgc agatggcatc   1020
tattccgcac catttaatac ggttgccgga gcgaccatcg aaaatcatga tggcgtcaac   1080
tacaacggcg acatggtgca gttgattcaa caagcaacga cgaaaagaag cacgtatgtt   1140
cgggtaaagg cgtcaaacgg aaagattttt tggattgatc aggctgccct taaagatccc   1200
aaaccggatc cgattttagc taaaaccgct gaaaattatt ttgcatccat taatcagaca   1260
aatcgcgcgg atggtattta ttctggtggg ccatacagaa caacgccttc agcatatgcg   1320
gctaactcaa atgccccaa attcaaaggc cagctggttc atgtgctggc cactgagaga   1380
accagatggt caactttcgc taaaattcaa ttcagtgacg gctcaatcta ctggatcgac   1440
acacaggcgt tgaagcgaag cggttttacg tctattattt cttcgcagac aaccagttat   1500
cagggcatta ttgatgaaac cggtcgaaaa gatggtgtgt atcgcgacgg cccttatcaa   1560
acaagtgcgg ccacattttt gatgaattat gatggtccta agtacagcaa ccgtcttgtg   1620
actgttttga agacttcaaa aacagcttgg tcaacttatg ccaatgtgaa acttaatgac   1680
ggcaccactt tctggattga cactgcagcc attaagaaag tagccctta cccaactctg   1740
tcgcaagaaa aagtcgatta taatgctgtg atcgatgaga caaatcgtaa agacggcgtc   1800
tacttaaccg gtccatatag aagtaatgtc agtgaataca gtgaaaatag taatggcccg   1860
aaatataacg gtaaggctgt tcacgtaacg gcgcaagcga cgaataagtg gtcaacttat   1920
gttcaggtta aacagctga cggtactcgt ttttggattg acaaggcggc aataaagccc   1980
attagtcttt atccgatcct ttcgtcttcc aaccagtcgt acactgcgac tattaatcag   2040
tcaactcggt ctgatggtat ctatgcaagt ggccccctatt cgacctcact agccacttat   2100
ggtattaatt acgatgccaa gaagtataac ggtcagacgg ttcaggttct caaagaagca   2160
cggacgagct ggtcaacata cgttcttgtc aaaacggcta gtggcgcaca gttttggatc   2220
gataagcttg gcattcagtc gtcatatttc ccaacgctgt ctcaaagcaa tgtcaattat   2280
gatgtcttaa ttgatgagaa tggtcgtgca gatggtattt actatgctgg accatataat   2340
tcaaatgcag caacatccgt tcaaaatagt attggtccga aatataatgg gcaggctgga   2400
catgcttctg ttgaagcaac caataagtgg tcaacttacg tgaaggtgac gctgacagat   2460
ggcacgagtt tctggattga taaggctgct atcaagtctc tgccaactga tccagtgctg   2520
agtagacgct cagtgcatta cactgctacg attaaccaaa acaatcgagc agatggcgtc   2580
tatacgacag gcccatatcg aacttcttat cagacatata cgattaatta cgatgccaaa   2640
aagtatgatg gcaacaagg aactgttatg caggaagtac cgacatcttg gtcaacttac   2700
gttcagatta agctgggttc tggcgcaacc atttggctgg acaaagccgg tgtccgtgca   2760
tcgtaa                                                              2766
```

<210> SEQ ID NO 90
<211> LENGTH: 921
<212> TYPE: PRT
<213> ORGANISM: Lactobacillus casei

<400> SEQUENCE: 90

```
Met Lys Leu Ser Lys His Phe Lys Leu Ile Met Thr Gly Ala Phe Ser
1               5                   10                  15

Leu Ala Ser Val Gly Leu Phe Ala Pro Ile Val Leu Gly Gln Gly Gln
            20                  25                  30

Arg Val Tyr Ala Gly Thr Ser Ser Thr Val Ser Thr Val Val Asn Gly
        35                  40                  45

Ser Asp Glu Gln Asp Phe His Leu Thr Asn Gln His Ser Asn Leu Asp
    50                  55                  60

Thr Asp Asn His Val Leu Gly Gly Gln Ala Ala Pro Ala Leu Arg
65                  70                  75                  80

Thr Lys Arg Ser Ile Met Ser Asn Gly Leu Gln Ala Asn Ser Ile Gln
                85                  90                  95

Thr Tyr Ser Gln Thr Val Met Ser Phe Thr Ile Gly Asp Ser Arg Val
            100                 105                 110

Pro Arg Val Asp Thr Val Asp Val Ala Ser Tyr Gln Asn Gly Met Thr
        115                 120                 125

Gln Ala Asn Tyr Asn Ser Leu Arg Thr Ser Gly Val Lys Ala Val Ile
130                 135                 140

Val Lys Ser Ser Glu Gly Ser Thr Tyr Arg Asn Pro Tyr Ala Ala Lys
145                 150                 155                 160

Gln Leu Ala Gln Ala Lys Ala Ala Gly Leu Lys Thr Ala Val Tyr His
                165                 170                 175

Tyr Val His Phe Ala Asn Gln Ser Asp Ala Ile Ala Glu Ala Asn Tyr
            180                 185                 190

Phe Ala Asn Thr Leu Asp Ser Leu Gly Phe Ser Lys Thr Ser Ala Val
        195                 200                 205

Val Ala Asp Ile Glu Asp Ser Asp Val Gly Gly Asp Val Ala Ala Asn
210                 215                 220

Val Asn Ala Phe Trp Asn Val Leu Ser Thr Arg Gly Tyr Val Asn His
225                 230                 235                 240

Ile Val Tyr Thr Gly Leu Tyr Tyr Ser Tyr Ser Lys Ala Ala Ile Ser
                245                 250                 255

Thr Val Gly Asn Glu Arg Ser Trp Val Ala Gln Tyr Pro Tyr Val Pro
            260                 265                 270

Ser Ala Asn Asn Leu Leu Asn Thr Gly Tyr Gly Ala Trp Gln Phe Ser
        275                 280                 285

Ser Met Ala Gly Ile Pro Asn Tyr Asn Gly Arg Val Asp Val Ser Ile
        290                 295                 300

Asp Tyr Gln Gly Ile Phe Thr Ser Ala Phe Ser Phe Asp His Val Ile
305                 310                 315                 320

Asp Ser His Ser Leu Ser Gly Val Lys Gln Ile Asp Glu Thr Asn Arg
                325                 330                 335

Ala Asp Gly Ile Tyr Ser Ala Pro Phe Asn Thr Val Ala Gly Ala Thr
            340                 345                 350

Ile Glu Asn His Asp Gly Val Asn Tyr Asn Gly Asp Met Val Gln Leu
        355                 360                 365

Ile Gln Gln Ala Thr Thr Lys Arg Ser Thr Tyr Val Arg Val Lys Ala
        370                 375                 380

Ser Asn Gly Lys Ile Phe Trp Ile Asp Gln Ala Ala Leu Lys Asp Pro
385                 390                 395                 400

Lys Pro Asp Pro Ile Leu Ala Lys Thr Ala Glu Asn Tyr Phe Ala Ser
                405                 410                 415
```

-continued

```
Ile Asn Gln Thr Asn Arg Ala Asp Gly Ile Tyr Ser Gly Gly Pro Tyr
            420                 425                 430

Arg Thr Thr Pro Ser Ala Tyr Ala Ala Asn Ser Asn Ala Pro Lys Phe
            435                 440                 445

Lys Gly Gln Leu Val His Val Leu Ala Thr Glu Arg Thr Arg Trp Ser
            450                 455                 460

Thr Phe Ala Lys Ile Gln Phe Ser Asp Gly Ser Ile Tyr Trp Ile Asp
465                 470                 475                 480

Thr Gln Ala Leu Lys Arg Ser Gly Phe Thr Ser Ile Ile Ser Ser Gln
                485                 490                 495

Thr Thr Ser Tyr Gln Gly Ile Ile Asp Glu Thr Gly Arg Lys Asp Gly
            500                 505                 510

Val Tyr Arg Asp Gly Pro Tyr Gln Thr Ser Ala Ala Thr Phe Leu Met
            515                 520                 525

Asn Tyr Asp Gly Pro Lys Tyr Ser Asn Arg Leu Val Thr Val Leu Lys
            530                 535                 540

Thr Ser Lys Thr Ala Trp Ser Thr Tyr Ala Asn Val Lys Leu Asn Asp
545                 550                 555                 560

Gly Thr Thr Phe Trp Ile Asp Thr Ala Ala Ile Lys Lys Val Ala Leu
                565                 570                 575

Tyr Pro Thr Leu Ser Gln Glu Lys Val Asp Tyr Asn Ala Val Ile Asp
            580                 585                 590

Glu Thr Asn Arg Lys Asp Gly Val Tyr Leu Thr Gly Pro Tyr Arg Ser
            595                 600                 605

Asn Val Ser Glu Tyr Ser Glu Asn Ser Asn Gly Pro Lys Tyr Asn Gly
            610                 615                 620

Lys Ala Val His Val Thr Ala Gln Ala Thr Asn Lys Trp Ser Thr Tyr
625                 630                 635                 640

Val Gln Val Thr Thr Ala Asp Gly Thr Arg Phe Trp Ile Asp Lys Ala
                645                 650                 655

Ala Ile Lys Pro Ile Ser Leu Tyr Pro Ile Leu Ser Ser Ser Asn Gln
            660                 665                 670

Ser Tyr Thr Ala Thr Ile Asn Gln Ser Thr Arg Ser Asp Gly Ile Tyr
            675                 680                 685

Ala Ser Gly Pro Tyr Ser Thr Ser Leu Ala Thr Tyr Gly Ile Asn Tyr
            690                 695                 700

Asp Ala Lys Lys Tyr Asn Gly Gln Thr Val Gln Val Leu Lys Glu Ala
705                 710                 715                 720

Arg Thr Ser Trp Ser Thr Tyr Val Leu Val Lys Thr Ala Ser Gly Ala
                725                 730                 735

Gln Phe Trp Ile Asp Lys Leu Gly Ile Gln Ser Ser Tyr Phe Pro Thr
            740                 745                 750

Leu Ser Gln Ser Asn Val Asn Tyr Asp Val Leu Ile Asp Glu Asn Gly
            755                 760                 765

Arg Ala Asp Gly Ile Tyr Tyr Ala Gly Pro Tyr Asn Ser Asn Ala Ala
            770                 775                 780

Thr Ser Val Gln Asn Ser Ile Gly Pro Lys Tyr Asn Gly Gln Ala Gly
785                 790                 795                 800

His Ala Ser Val Glu Ala Thr Asn Lys Trp Ser Thr Tyr Val Lys Val
                805                 810                 815

Thr Leu Thr Asp Gly Thr Ser Phe Trp Ile Asp Lys Ala Ala Ile Lys
            820                 825                 830

Ser Leu Pro Thr Asp Pro Val Leu Ser Arg Arg Ser Val His Tyr Thr
            835                 840                 845
```

```
Ala Thr Ile Asn Gln Asn Asn Arg Ala Asp Gly Val Tyr Thr Thr Gly
            850                 855                 860

Pro Tyr Arg Thr Ser Tyr Gln Thr Tyr Thr Ile Asn Tyr Asp Ala Lys
865                 870                 875                 880

Lys Tyr Asp Gly Gln Gln Gly Thr Val Met Gln Glu Val Pro Thr Ser
                885                 890                 895

Trp Ser Thr Tyr Val Gln Ile Lys Leu Gly Ser Gly Ala Thr Ile Trp
                900                 905                 910

Leu Asp Lys Ala Gly Val Arg Ala Ser
            915                 920

<210> SEQ ID NO 91
<211> LENGTH: 1461
<212> TYPE: DNA
<213> ORGANISM: Lactobacillus casei

<400> SEQUENCE: 91
atgcaagttt tggagatttt tatgaaagta atcaagaact ttttttggaa tgcgggttat      60
caggtcttcg tcctgattgt gccgctggta actgtacctt atattaatcg agtactagga    120
ccgacaggcg ttgggataaa tgcgttcact aactcaattg tccaatactt tattctcttt    180
ggtagtctgg gtattaacct ttatgggaat cggggcacag cttatcgaag agatgatcga    240
aaaagcgctg accacctattt tgggaagtc accatacttc gatttgtgac gattggtata    300
gctgtgcttg cgtatctcat gtttatattt gccgtcgatg agtatcgtgt tttttatctt    360
gctcaaggcg ttatgctttt gggaacagcg tttgatattt cgtggttttt ccaaggatta    420
gaaaactttc gggtaacggt ggttcgtaat gtgttggtgc ggatcgcttc cctcattctg    480
attttcctgt tagtgcataa agcagatgat actgctttgt atattctgat catgtctggc    540
tcacagatgt tggggaatct aacattctgg ccctcattac gcgcaaatct gacacatttt    600
ccgaaactgt caagcctgaa catctggcag catattaaac cggcgttcct tctattgatt    660
ccgcaactgg cgattcaaat ttatgttcaa ctgaataaaa cgatgcttgg aattttacag    720
ggtgttacgg catctggttt ttacgaaagt tcggacaaaa tcattaaaat gttattggct    780
cttgtgacag caaccggcac cgtcttattg ccgcatgtgg cccattattt tgcccaaggt    840
gatcacgatg ccgtcaaacg ctcattagaa acatcgatgc acgtgatttt ggttattgct    900
tttcctttag ccttttgggat tgcggcggtt ccacaacgt ttacttatta ttttttttagc    960 acaaagttta tgcccgtggc acccttgatg gcagctgaag cgattgtcgt cattccgatt   1020
tcgattgcga gtgccattgg tgtgcaatat ttgctgccaa ctaaccaagt taagtcatat   1080
actgtctcag ttattttggg atccatcgtt aatattgtag tgaatgtgcc tcttattctg   1140
tggttaggaa caatgggcgc tgtgattggc actatccttt ctgaatcagt cgtgacgatt   1200
tatcaggtct atgctattaa aaatcagctt gatctcagag cttgtttag tgaatcatgg   1260 aagtattgcc tcagcgcggt cgtgatgttt ggtgttgtaa aaggtcttga gattgcctgg   1320
tccaccagct tgatcggcct agttgttgaa gttttgattg gtatggtggt gtactttgtg   1380
gtgctgttgg ggttacgacc gcacattatc attgggtatg ttcgcccata tgtcgatcag   1440
atgcgtcggc gtcttcgtta a                                             1461

<210> SEQ ID NO 92
<211> LENGTH: 486
<212> TYPE: PRT
<213> ORGANISM: Lactobacillus casei
```

<400> SEQUENCE: 92

```
Met Gln Val Leu Glu Ile Phe Met Lys Val Ile Lys Asn Phe Phe Trp
1               5                   10                  15

Asn Ala Gly Tyr Gln Val Phe Val Leu Ile Val Pro Leu Val Thr Val
            20                  25                  30

Pro Tyr Ile Asn Arg Val Leu Gly Pro Thr Gly Val Gly Ile Asn Ala
        35                  40                  45

Phe Thr Asn Ser Ile Val Gln Tyr Phe Ile Leu Phe Gly Ser Leu Gly
    50                  55                  60

Ile Asn Leu Tyr Gly Asn Arg Gly Thr Ala Tyr Arg Arg Asp Asp Arg
65                  70                  75                  80

Lys Ala Leu Thr Thr Tyr Phe Trp Glu Val Thr Ile Leu Arg Phe Val
                85                  90                  95

Thr Ile Gly Ile Ala Val Leu Ala Tyr Leu Met Phe Ile Phe Ala Val
            100                 105                 110

Asp Glu Tyr Arg Val Phe Tyr Leu Ala Gln Gly Val Met Leu Leu Gly
        115                 120                 125

Thr Ala Phe Asp Ile Ser Trp Phe Phe Gln Gly Leu Glu Asn Phe Arg
    130                 135                 140

Val Thr Val Val Arg Asn Val Leu Val Arg Ile Ala Ser Leu Ile Leu
145                 150                 155                 160

Ile Phe Leu Leu Val His Lys Ala Asp Asp Thr Ala Leu Tyr Ile Leu
                165                 170                 175

Ile Met Ser Gly Ser Gln Met Leu Gly Asn Leu Thr Phe Trp Pro Ser
            180                 185                 190

Leu Arg Ala Asn Leu Thr His Phe Pro Lys Leu Ser Ser Leu Asn Ile
        195                 200                 205

Trp Gln His Ile Lys Pro Ala Phe Leu Leu Leu Ile Pro Gln Leu Ala
    210                 215                 220

Ile Gln Ile Tyr Val Gln Leu Asn Lys Thr Met Leu Gly Ile Leu Gln
225                 230                 235                 240

Gly Val Thr Ala Ser Gly Phe Tyr Glu Ser Ser Asp Lys Ile Ile Lys
                245                 250                 255

Met Leu Leu Ala Leu Val Thr Ala Thr Gly Thr Val Leu Leu Pro His
            260                 265                 270

Val Ala His Tyr Phe Ala Gln Gly Asp His Asp Ala Val Lys Arg Ser
        275                 280                 285

Leu Glu Thr Ser Met His Val Ile Leu Val Ile Ala Phe Pro Leu Ala
    290                 295                 300

Phe Gly Ile Ala Ala Val Ser Thr Thr Phe Thr Tyr Tyr Phe Phe Ser
305                 310                 315                 320

Thr Lys Phe Met Pro Val Ala Pro Leu Met Ala Ala Glu Ala Ile Val
                325                 330                 335

Val Ile Pro Ile Ser Ile Ala Ser Ala Ile Gly Val Gln Tyr Leu Leu
            340                 345                 350

Pro Thr Asn Gln Val Lys Ser Tyr Thr Val Ser Val Ile Leu Gly Ser
        355                 360                 365

Ile Val Asn Ile Val Val Asn Val Pro Leu Ile Leu Trp Leu Gly Thr
    370                 375                 380

Met Gly Ala Val Ile Gly Thr Ile Leu Ser Glu Ser Val Val Thr Ile
385                 390                 395                 400

Tyr Gln Val Tyr Ala Ile Lys Asn Gln Leu Asp Leu Arg Gly Leu Phe
                405                 410                 415
```

```
Ser Glu Ser Trp Lys Tyr Cys Leu Ser Ala Val Val Met Phe Gly Val
            420                 425                 430

Val Lys Gly Leu Glu Ile Ala Trp Ser Thr Ser Leu Ile Gly Leu Val
        435                 440                 445

Val Glu Val Leu Ile Gly Met Val Val Tyr Phe Val Val Leu Leu Gly
        450                 455                 460

Leu Arg Pro His Ile Ile Ile Gly Tyr Val Arg Pro Tyr Val Asp Gln
465                 470                 475                 480

Met Arg Arg Arg Leu Arg
                485

<210> SEQ ID NO 93
<211> LENGTH: 864
<212> TYPE: DNA
<213> ORGANISM: Lactobacillus casei

<400> SEQUENCE: 93
atgatgaaga ttgggttgat ccttaactat cgaaattatc gacagaccat cgcatgttgc    60
cgcaacttaa tcaaggctgg actggatcgc attgtcgtag ttgataatgg gtcgccaaat   120
gaatcattgg ctaagcttaa atcatcttta ggaaatgatg caaaagttag cattctaggt   180
accaaagcca acttggggta tgcgcgagga ataactttg acttcaagc aattgaaaaa     240 aagtttgggc tagcggacga tcacctcttg tatattgtta atccggatag tgtgcctgat   300
gcaactgtga ttaagcagat ttcggcgttt tgctggtctc atcccgatgc aggtaccatg   360
acggtgatcc aagagggtaa tcctaaaatg gcttggcata atctgaccaa acacgagca    420 atgcttata actcaagaat ctttctaag cttgcttatc gacttggcca tcatgaagaa     480
gttgtgcctt atcatgtcgc aggacaaagg acagcaagca ttaaagtcga tgtgaattct    540
ggggcattct ttgcaatacg tcaaacggtt atggcaaagg ttggttattt tgatactgcg    600 acctccttt attatgaaga gcaagcatta tccttcaaat tgcaagctca aggatttcag    660
aattacttat tgacaacatc aacttatcgc catgaagggc agggatctac ccacttagcc    720
acgcgtgcta tgttggggta ttatcaacaa agccgacgat atttactgaa acaatatttg    780
catgcaggcc cattagcgtt gagatttat gattggacga ttaggcttga agatatcttg     840
gctggcgaca gatcaaaaac gtaa                                           864

<210> SEQ ID NO 94
<211> LENGTH: 287
<212> TYPE: PRT
<213> ORGANISM: Lactobacillus casei

<400> SEQUENCE: 94

Met Met Lys Ile Gly Leu Ile Leu Asn Tyr Arg Asn Tyr Arg Gln Thr
1               5                   10                  15

Ile Ala Cys Cys Arg Asn Leu Ile Lys Ala Gly Leu Asp Arg Ile Val
            20                  25                  30

Val Val Asp Asn Gly Ser Pro Asn Glu Ser Leu Ala Lys Leu Lys Ser
        35                  40                  45

Ser Leu Gly Asn Asp Ala Lys Val Ser Ile Leu Gly Thr Lys Ala Asn
    50                  55                  60

Leu Gly Tyr Ala Arg Gly Asn Asn Phe Gly Leu Gln Ala Ile Glu Lys
65                  70                  75                  80

Lys Phe Gly Leu Ala Asp Asp His Leu Leu Tyr Ile Val Asn Pro Asp
                85                  90                  95
```

```
Ser Val Pro Asp Ala Thr Val Ile Lys Gln Ile Ser Ala Phe Cys Trp
            100                 105                 110

Ser His Pro Asp Ala Gly Thr Met Thr Val Ile Gln Glu Gly Asn Pro
            115                 120                 125

Lys Met Ala Trp His Asn Leu Thr Lys Thr Arg Ala Met Leu Tyr Asn
130                 135                 140

Ser Arg Ile Phe Ser Lys Leu Ala Tyr Arg Leu Gly His His Glu Glu
145                 150                 155                 160

Val Val Pro Tyr His Val Ala Gly Gln Arg Thr Ala Ser Ile Lys Val
                165                 170                 175

Asp Val Asn Ser Gly Ala Phe Phe Ala Ile Arg Gln Thr Val Met Ala
            180                 185                 190

Lys Val Gly Tyr Phe Asp Thr Ala Thr Phe Leu Tyr Tyr Glu Glu Gln
            195                 200                 205

Ala Leu Ser Phe Lys Leu Gln Ala Gln Gly Phe Gln Asn Tyr Leu Leu
            210                 215                 220

Thr Thr Ser Thr Tyr Arg His Glu Gly Gln Gly Ser Thr His Leu Ala
225                 230                 235                 240

Thr Arg Ala Met Leu Gly Tyr Tyr Gln Gln Ser Arg Arg Tyr Leu Leu
                245                 250                 255

Lys Gln Tyr Leu His Ala Gly Pro Leu Ala Leu Arg Phe Tyr Asp Trp
            260                 265                 270

Thr Ile Arg Leu Glu Asp Ile Leu Ala Gly Asp Arg Ser Lys Thr
            275                 280                 285

<210> SEQ ID NO 95
<211> LENGTH: 1209
<212> TYPE: DNA
<213> ORGANISM: Lactobacillus casei

<400> SEQUENCE: 95
gtgaatatcg ggatttttac agatagctac tttccacaag tcagtggcgt cgcgacgtcc      60
atcaagacct tgaaggacga tctggagcgt aagggccatc aggtttatat ttttacaacg     120
actgatccgc atgtgccaga cgacgccgtt gaacctaatt tattccgatt taccagtgta     180
ccgtttgtct cattcacgga tcggcgaatt gcggttcgtg ggcttttca tgcttacgca      240 gtggcgaagg aattgaactt ggacattgtt catacacaaa ctgaattttc gatgggggtat    300 atcggcaaat tgtcgccaa gcagttgaaa attccgacaa tccatactta tcacactatg     360
tatgaggatt atctgcatta tgtcctgaat ggtcatttgc tgaagcctta tcatgtgaag    420
cagtttacgc gggcgtttct ttatcatgtc agtggcgttg ttgcgccttc tgaacgcgtt    480
tatgatacgt gcggcgata tggcgtcaaa actgagatca aaatcattcc aactgggggtt    540 gatttgactc agttgtgccca gcaaaaagat ccgcatttac gtgacaagct cgggttggcg    600
catgtcccgg ttttggtctc actcagtcgg tcgcgtatg aaaagcgaat tgataaggtg    660
atcagtgcca tgcctaaaat tctggaacag gtgccccaag cggtgctttt aattgttggc    720
gatgggcctg cgcgtgaaga cttagaggcg caagttgctg agctgggtct caaggagcat    780
gtccgattca ccggtgaaat tgaccatgat gatgttggtg actattaccg ggttggcgat    840
gtgtttgtat cggcaagtga ctccgagtca caggggttaa cttatatcga agcgatggcg    900
gcggatcgga aagtggttgc cttgacaggg gattatacgg atcaacttt ggatgatccg    960 gcgttaggga caacattttc aactgagact gaaatggtgc atcaggtcgt gaattacttg   1020
aaacatccaa atgcttacga tgatgctaag ccgcgtcaag aaaagttagc ggcaatttct   1080
```

```
gcagatcgat tggcgatcg ggttttggat ttctatcaag acattttgtc acactattcg   1140
cctaatgagg ccgatgaagc tgcaccatgg accgatgaag attccagtaa acggaccatg   1200
aaaggttaa                                                           1209
```

<210> SEQ ID NO 96
<211> LENGTH: 402
<212> TYPE: PRT
<213> ORGANISM: Lactobacillus casei

<400> SEQUENCE: 96

```
Met Asn Ile Gly Ile Phe Thr Asp Ser Tyr Phe Pro Gln Val Ser Gly
1               5                   10                  15

Val Ala Thr Ser Ile Lys Thr Leu Lys Asp Asp Leu Glu Arg Lys Gly
            20                  25                  30

His Gln Val Tyr Ile Phe Thr Thr Asp Pro His Val Pro Asp Asp
        35                  40                  45

Ala Val Glu Pro Asn Leu Phe Arg Phe Thr Ser Val Pro Phe Val Ser
    50                  55                  60

Phe Thr Asp Arg Arg Ile Ala Val Arg Gly Leu Phe His Ala Tyr Ala
65                  70                  75                  80

Val Ala Lys Glu Leu Asn Leu Asp Ile Val His Thr Gln Thr Glu Phe
                85                  90                  95

Ser Met Gly Tyr Ile Gly Lys Phe Val Ala Lys Gln Leu Lys Ile Pro
            100                 105                 110

Thr Ile His Thr Tyr His Thr Met Tyr Glu Asp Tyr Leu His Tyr Val
        115                 120                 125

Leu Asn Gly His Leu Leu Lys Pro Tyr His Val Lys Gln Phe Thr Arg
130                 135                 140

Ala Phe Leu Tyr His Val Ser Gly Val Val Ala Pro Ser Glu Arg Val
145                 150                 155                 160

Tyr Asp Thr Leu Arg Arg Tyr Gly Val Lys Thr Glu Ile Lys Ile Ile
                165                 170                 175

Pro Thr Gly Val Asp Leu Thr Gln Phe Ala Gln Gln Lys Asp Pro His
            180                 185                 190

Leu Arg Asp Lys Leu Gly Leu Ala His Val Pro Val Leu Val Ser Leu
        195                 200                 205

Ser Arg Val Ala Tyr Glu Lys Arg Ile Asp Lys Val Ile Ser Ala Met
    210                 215                 220

Pro Lys Ile Leu Glu Gln Val Pro Gln Ala Val Leu Leu Ile Val Gly
225                 230                 235                 240

Asp Gly Pro Ala Arg Glu Asp Leu Glu Ala Gln Val Ala Glu Leu Gly
                245                 250                 255

Leu Lys Glu His Val Arg Phe Thr Gly Glu Ile Asp His Asp Asp Val
            260                 265                 270

Gly Asp Tyr Tyr Arg Val Gly Asp Val Phe Val Ser Ala Ser Asp Ser
        275                 280                 285

Glu Ser Gln Gly Leu Thr Tyr Ile Glu Ala Met Ala Ala Asp Arg Lys
    290                 295                 300

Val Val Ala Leu Thr Gly Asp Tyr Thr Asp Gln Leu Leu Asp Asp Pro
305                 310                 315                 320

Ala Leu Gly Thr Thr Phe Ser Thr Glu Thr Glu Met Val His Gln Val
                325                 330                 335

Val Asn Tyr Leu Lys His Pro Asn Ala Tyr Asp Asp Ala Lys Pro Arg
            340                 345                 350
```

-continued

```
Gln Glu Lys Leu Ala Ala Ile Ser Ala Asp Arg Phe Gly Asp Arg Val
        355                 360                 365

Leu Asp Phe Tyr Gln Asp Ile Leu Ser His Tyr Ser Pro Asn Glu Ala
    370                 375                 380

Asp Glu Ala Ala Pro Trp Thr Asp Glu Asp Ser Ser Lys Arg Thr Met
385                 390                 395                 400

Lys Gly

<210> SEQ ID NO 97
<211> LENGTH: 1029
<212> TYPE: DNA
<213> ORGANISM: Lactobacillus casei

<400> SEQUENCE: 97
atgattgtta ttaatatgtt ttcctctgcc aataaggttg caggacaagg agttggcgca      60
gtctacacag aactgatggg cttgctgaaa cacgattttt caaatgaatt tgaagttaac     120
gtcaatcgtt atacgcgtag tgacatcagc cattatcata cgattgatcc taaattttat     180
ttatctactt tctccaaaaa acggggtcgc aagattggct tgttcacttt tgtgccgagt     240
acactggatg cgagtctgaa gttgccgcga gtggcgcggt ggacgcttga taagtatacg     300
ttggcttttt ataagcgaat ggatcagtta gtggtggtga acccgaattt tattcctaag     360
ttagaagctt atgggatcag tcgcgacaaa gtgacttata ttcctaattt cgtatcgcaa     420
cgaacgtttc atccagtatc cactgaaaag cggcaggctt tgcgacatgc caatggcttt     480
aaacctgatg attttgtcat ttttggcgca ggtcaggtgc aggatcgtaa gggtgtcagc     540
gactttatca aattagcaaa acaaaatccg gaatttcgtt ttgtttgggc aggtgggttc     600
tcttttggcc gcattactga aggctacgac catttgaaga aggccgtagc agaagccccg     660
gcaaacttgg attttaccgg gattatgcca cgggagacaa tgattgacta ttacaatatg     720
gccgatgttt tcttattgcc ttcttatgaa gagctgttcc caatgtccgt ccttgaggct     780
tttgcaacgg gaacgccagt gatggtgcgg gatcttgagc tgtatcacca aatcatcaca     840
ccttatgcca tcacggctgt tgatgttgac gatatgcagt ctcgattgcg ggcacttgcg     900
gatgatcatg atcttttggc aacttatgca actaagagtc gacaagctgc tgaagtttac     960
gatgaaagcc gacttgaaaa agtctggcac gatttctatc ttcatcaagc tgcactgggg    1020
aagcactag                                                            1029

<210> SEQ ID NO 98
<211> LENGTH: 342
<212> TYPE: PRT
<213> ORGANISM: Lactobacillus casei

<400> SEQUENCE: 98

Met Ile Val Ile Asn Met Phe Ser Ser Ala Asn Lys Val Ala Gly Gln
1               5                   10                  15

Gly Val Gly Ala Val Tyr Thr Glu Leu Met Gly Leu Leu Lys His Asp
            20                  25                  30

Phe Ser Asn Glu Phe Glu Val Asn Val Asn Arg Tyr Thr Arg Ser Asp
        35                  40                  45

Ile Ser His Tyr His Thr Ile Asp Pro Lys Phe Tyr Leu Ser Thr Phe
    50                  55                  60

Ser Lys Lys Arg Gly Arg Lys Ile Gly Phe Val His Phe Val Pro Ser
65                  70                  75                  80

Thr Leu Asp Ala Ser Leu Lys Leu Pro Arg Val Ala Arg Trp Thr Leu
                85                  90                  95
```

```
Asp Lys Tyr Thr Leu Ala Phe Tyr Lys Arg Met Asp Gln Leu Val Val
            100                 105                 110

Val Asn Pro Asn Phe Ile Pro Lys Leu Glu Ala Tyr Gly Ile Ser Arg
            115                 120                 125

Asp Lys Val Thr Tyr Ile Pro Asn Phe Val Ser Gln Arg Thr Phe His
            130                 135                 140

Pro Val Ser Thr Glu Lys Arg Gln Ala Leu Arg His Ala Asn Gly Phe
145                 150                 155                 160

Lys Pro Asp Asp Phe Val Ile Phe Gly Ala Gly Gln Val Gln Asp Arg
                165                 170                 175

Lys Gly Val Ser Asp Phe Ile Lys Leu Ala Lys Gln Asn Pro Glu Phe
            180                 185                 190

Arg Phe Val Trp Ala Gly Gly Phe Ser Phe Gly Arg Ile Thr Glu Gly
            195                 200                 205

Tyr Asp His Leu Lys Lys Ala Val Ala Glu Ala Pro Ala Asn Leu Asp
            210                 215                 220

Phe Thr Gly Ile Met Pro Arg Glu Thr Met Ile Asp Tyr Tyr Asn Met
225                 230                 235                 240

Ala Asp Val Phe Leu Leu Pro Ser Tyr Glu Glu Leu Phe Pro Met Ser
                245                 250                 255

Val Leu Glu Ala Phe Ala Thr Gly Thr Pro Val Met Val Arg Asp Leu
            260                 265                 270

Glu Leu Tyr His Gln Ile Ile Thr Pro Tyr Ala Ile Thr Ala Val Asp
            275                 280                 285

Val Asp Asp Met Gln Ser Arg Leu Arg Ala Leu Ala Asp His Asp
            290                 295                 300

Leu Leu Ala Thr Tyr Ala Thr Lys Ser Arg Gln Ala Ala Glu Val Tyr
305                 310                 315                 320

Asp Glu Ser Arg Leu Glu Lys Val Trp His Asp Phe Tyr Leu His Gln
                325                 330                 335

Ala Ala Leu Gly Lys His
            340

<210> SEQ ID NO 99
<211> LENGTH: 1014
<212> TYPE: DNA
<213> ORGANISM: Lactobacillus casei

<400> SEQUENCE: 99
atgacacgga agaacaaact ggctgtctta atcatgattt tgattggcgc cggtattttt      60
atttatgaag ctcgtgatct gaacggcgca caattaatcc acgaactatt gacgcttgat     120
ctcaagtggc tgctggtggc ttttttgctc atgtttgggt cgtggatcat tgaaactttt     180
gtggttcaga tctttattcg aagtgaagct gatgatttag actttaaaac cgctttgcgt     240
gtgccgttgg ttgaacaatt gtttaatgca attcgccga tggcttctgg tggtcagcca     300
gcccaattat ttgctttgat gcaaagtggc gttgaagctg ccgggcaag ttccgtgttg     360 ttgatgaagt ttgtcgtgta tcaattcatg gtcctgatta actttgtcct gacactattc     420
atcgggtttg atcaggtgtc caaacatttt ggggcgcttg ctttgttcat cgttttttggt     480 tttgtgattc atgtggttgt catcgtaggc ttgctcatgg tgatgtatta ctataagttc     540 acaaaaaat tagtgaattt ggtgatgata ccgattggct ggtttgtcaa acctgagaaa     600
aaacttgcca tgcaaagtaa ccttgatcat aaaattgaca cttttacgc agagagtttg     660 cacttgaaac gcgaaaagaa gcgggtcatc aaggcttgct tgttgacact tgtgcaattg     720
```

```
ctgctttact atgcggtgcc gtactttgtg ctcctgtcgc ttggcgtaag tcatgttagt    780
atcgttgagg tcatcgtgtt gcacgtgatg attgtgatga ttgtcagcct gtttccgatt    840
ccaggcggtg ctggcgggc cgagtatagc tttaagacct tgtttgcgac ttatgttgcg    900
tcgccttcaa aattgattct agggatgctg ttatggcggt tcttgaccta ttacctgggg    960
atgatctgcg gcatcattgc catggcattc ccgccaaaaa gcaaacgtac gtga         1014
```

<210> SEQ ID NO 100
<211> LENGTH: 337
<212> TYPE: PRT
<213> ORGANISM: Lactobacillus casei

<400> SEQUENCE: 100

```
Met Thr Arg Lys Asn Lys Leu Ala Val Leu Ile Met Ile Leu Ile Gly
1               5                   10                  15

Ala Gly Ile Phe Ile Tyr Glu Ala Arg Asp Leu Asn Gly Ala Gln Leu
            20                  25                  30

Ile His Glu Leu Leu Thr Leu Asp Leu Lys Trp Leu Leu Val Ala Phe
        35                  40                  45

Leu Leu Met Phe Gly Ser Trp Ile Ile Glu Thr Phe Val Val Gln Ile
    50                  55                  60

Phe Ile Arg Ser Glu Ala Asp Asp Leu Asp Phe Lys Thr Ala Leu Arg
65                  70                  75                  80

Val Pro Leu Val Glu Gln Leu Phe Asn Ala Ile Thr Pro Met Ala Ser
                85                  90                  95

Gly Gly Gln Pro Ala Gln Leu Phe Ala Leu Met Gln Ser Gly Val Glu
            100                 105                 110

Ala Gly Arg Ala Ser Ser Val Leu Leu Met Lys Phe Val Tyr Gln
        115                 120                 125

Phe Met Val Leu Ile Asn Phe Val Leu Thr Leu Phe Ile Gly Phe Asp
130                 135                 140

Gln Val Ser Lys His Phe Gly Ala Leu Ala Leu Phe Ile Val Phe Gly
145                 150                 155                 160

Phe Val Ile His Val Val Val Ile Val Gly Leu Leu Met Val Met Tyr
                165                 170                 175

Tyr Tyr Lys Phe Thr Lys Lys Leu Val Asn Leu Val Met Ile Pro Ile
            180                 185                 190

Gly Trp Phe Val Lys Pro Glu Lys Lys Leu Ala Met Gln Ser Asn Leu
        195                 200                 205

Asp His Lys Ile Asp Thr Phe Tyr Ala Glu Ser Leu His Leu Lys Arg
    210                 215                 220

Glu Lys Lys Arg Val Ile Lys Ala Cys Leu Leu Thr Leu Val Gln Leu
225                 230                 235                 240

Leu Leu Tyr Tyr Ala Val Pro Tyr Phe Val Leu Leu Ser Leu Gly Val
                245                 250                 255

Ser His Val Ser Ile Val Glu Val Ile Val Leu His Val Met Ile Val
            260                 265                 270

Met Ile Val Ser Leu Phe Pro Ile Pro Gly Gly Ala Gly Gly Ala Glu
        275                 280                 285

Tyr Ser Phe Lys Thr Leu Phe Ala Thr Tyr Val Ala Ser Pro Ser Lys
    290                 295                 300

Leu Ile Leu Gly Met Leu Leu Trp Arg Phe Leu Thr Tyr Tyr Leu Gly
305                 310                 315                 320
```

Met Ile Cys Gly Ile Ile Ala Met Ala Phe Pro Pro Lys Ser Lys Arg
             325                 330                 335

Thr

<210> SEQ ID NO 101
<211> LENGTH: 1644
<212> TYPE: DNA
<213> ORGANISM: Lactobacillus casei

<400> SEQUENCE: 101

| | | | | | |
|---|---|---|---|---|---|
| atggagaatt | cgctgggcag | cggtaatcaa | ccgcaacgtt | cagataagga | aaaaatgatc | 60 |
| cgcggctcgg | cgtggatgac | tgccggcagt | gttttttcgc | ggattttagg | ggccatttat | 120 |
| gtcattccat | ggcgtatttg | gcttggagca | gcgtttctaa | ctgccaacgc | tttgtttaca | 180 |
| aaaggttatc | aaatttacag | tcttttttctg | attatttcga | ctgcgggtgt | tcctggtgct | 240 |
| gtttccaaac | aggttgcccg | gtacaatgct | atgggcgaat | ataaaaccgg | gatgcgtctt | 300 |
| ttttaccacg | gcacttttgc | catggtgctg | atggggattg | tctcgtgtgg | tgccatgtgg | 360 |
| ctgctctcgc | cgcttttagc | agcgggtgac | gcgcgcatga | taccggtttt | tcgttcactg | 420 |
| gcatggccgt | tgctgctaat | tccgtcgctt | agtttgattc | gcgggttttt | ccaaggttat | 480 |
| aacgagatgg | cgccgagtgc | catcagtcag | tttattgaac | aagtggcgcg | aattctttat | 540 |
| atgttagtga | tgacttacgc | gattatggtg | gcgggtaacc | acagctatct | gagtgcggtg | 600 |
| attcactcca | ccttcgccgc | gttcatcggg | gccgttttcg | gacttggact | gttagttgtt | 660 |
| tatttcctcc | ggcaaaaacc | acggttggat | gcgttggttg | cccaaagtgc | taattccctg | 720 |
| cagatcagtg | tcaatgagat | tcttctagat | gtggcacggc | aggcgattcc | atttatcatc | 780 |
| atggattcaa | cgattaatat | ttactacatc | gttgaccagt | acacatttaa | tccaatgatg | 840 |
| aaggctttt | atctcgttag | cgaagatcag | cttgaccgtt | tttatgcgct | gttttgccgga | 900 |
| aatgcgaata | aactgattat | gatcgttgtt | agtctggcag | ttgctatggc | cattactgta | 960 |
| gtaccattat | tggcaggtgc | gaaaacgcgc | ggtgatgttg | agggattggc | ccggcaaatc | 1020 |
| acgaatacac | tgcagttgtt | ttttatcgtc | atgataccct | tcggcgttggg | gatggtggca | 1080 |
| gtcgcgcgcc | cactgtatgt | tttgttctat | cgggatatgg | actggttggg | cattcgcttg | 1140 |
| ttgcagattt | catcactttt | agcgattatg | ctgggcttgt | tacggttttt | ggcagcaatt | 1200 |
| cttcagggat | tgttcaataa | ccgtcttgct | attcaagaga | tgttgattgg | cttggcagtt | 1260 |
| aaagtgattg | tacagtggcc | aatgattttc | ttcttcaatg | tttacggtcc | ggttttgtcc | 1320 |
| acaatgttag | gcatgacggt | ctcgagtctc | ctgatgctct | attcaacgaa | tcggatgtac | 1380 |
| aatattcatg | tacgccaaac | cattcgccgc | ggcgtcggta | ttctggcctt | tccttgatc | 1440 |
| atgtgcgccg | tttgttacct | gattgtgaat | gcatcaacct | tggtgatcaa | tccgcggagt | 1500 |
| cagttcgggg | cagcgttcgt | cttgctgatt | gcagttgggg | tgggcgtttt | gatttacgtt | 1560 |
| tatttgattt | tgaaaacgcg | tttggctgat | ttaatcattg | gtgagcgaat | tagtcgactt | 1620 |
| cgcgatattt | tacacattcg | gtga | | | | 1644 |

<210> SEQ ID NO 102
<211> LENGTH: 547
<212> TYPE: PRT
<213> ORGANISM: Lactobacillus casei

<400> SEQUENCE: 102

```
Met Glu Asn Ser Leu Gly Ser Gly Asn Gln Pro Gln Arg Ser Asp Lys
1               5                   10                  15

Glu Lys Met Ile Arg Gly Ser Ala Trp Met Thr Ala Gly Ser Val Phe
            20                  25                  30

Ser Arg Ile Leu Gly Ala Ile Tyr Val Ile Pro Trp Arg Ile Trp Leu
        35                  40                  45

Gly Ala Ala Phe Leu Thr Ala Asn Ala Leu Phe Thr Lys Gly Tyr Gln
    50                  55                  60

Ile Tyr Ser Leu Phe Leu Ile Ile Ser Thr Ala Gly Val Pro Gly Ala
65                  70                  75                  80

Val Ser Lys Gln Val Ala Arg Tyr Asn Ala Met Gly Glu Tyr Lys Thr
                85                  90                  95

Gly Met Arg Leu Phe Tyr His Gly Thr Phe Ala Met Val Leu Met Gly
            100                 105                 110

Ile Val Ser Cys Gly Ala Met Trp Leu Leu Ser Pro Leu Leu Ala Ala
            115                 120                 125

Gly Asp Ala Arg Met Ile Pro Val Phe Arg Ser Leu Ala Trp Pro Leu
    130                 135                 140

Leu Leu Ile Pro Ser Leu Ser Leu Ile Arg Gly Phe Phe Gln Gly Tyr
145                 150                 155                 160

Asn Glu Met Ala Pro Ser Ala Ile Ser Gln Phe Ile Glu Gln Val Ala
                165                 170                 175

Arg Ile Leu Tyr Met Leu Val Met Thr Tyr Ala Ile Met Val Ala Gly
            180                 185                 190

Asn His Ser Tyr Leu Ser Ala Val Ile His Ser Thr Phe Ala Ala Phe
        195                 200                 205

Ile Gly Ala Val Phe Gly Leu Gly Leu Leu Val Val Tyr Phe Leu Arg
210                 215                 220

Gln Lys Pro Arg Leu Asp Ala Leu Val Ala Gln Ser Ala Asn Ser Leu
225                 230                 235                 240

Gln Ile Ser Val Asn Glu Ile Leu Leu Asp Val Ala Arg Gln Ala Ile
                245                 250                 255

Pro Phe Ile Ile Met Asp Ser Thr Ile Asn Ile Tyr Tyr Ile Val Asp
            260                 265                 270

Gln Tyr Thr Phe Asn Pro Met Met Lys Ala Phe Tyr Leu Val Ser Glu
        275                 280                 285

Asp Gln Leu Asp Arg Phe Tyr Ala Leu Phe Ala Gly Asn Ala Asn Lys
    290                 295                 300

Leu Ile Met Ile Val Val Ser Leu Ala Val Ala Met Ala Ile Thr Val
305                 310                 315                 320

Val Pro Leu Leu Ala Gly Ala Lys Thr Arg Gly Asp Val Glu Gly Leu
                325                 330                 335

Ala Arg Gln Ile Thr Asn Thr Leu Gln Leu Phe Phe Ile Val Met Ile
            340                 345                 350

Pro Ser Ala Leu Gly Met Val Ala Val Ala Arg Pro Leu Tyr Val Leu
        355                 360                 365

Phe Tyr Arg Asp Met Asp Trp Leu Gly Ile Arg Leu Leu Gln Ile Ser
    370                 375                 380

Ser Leu Leu Ala Ile Met Leu Gly Leu Phe Thr Val Leu Ala Ala Ile
385                 390                 395                 400

Leu Gln Gly Leu Phe Asn Asn Arg Leu Ala Ile Gln Glu Met Leu Ile
                405                 410                 415
```

-continued

```
Gly Leu Ala Val Lys Val Ile Val Gln Trp Pro Met Ile Phe Phe Phe
            420                 425                 430

Asn Val Tyr Gly Pro Val Leu Ser Thr Met Leu Gly Met Thr Val Ser
        435                 440                 445

Ser Leu Leu Met Leu Tyr Ser Thr Asn Arg Met Tyr Asn Ile His Val
    450                 455                 460

Arg Gln Thr Ile Arg Arg Gly Val Gly Ile Leu Ala Phe Ser Leu Ile
465                 470                 475                 480

Met Cys Ala Val Cys Tyr Leu Ile Val Asn Ala Ser Thr Leu Val Ile
                485                 490                 495

Asn Pro Arg Ser Gln Phe Gly Ala Ala Phe Val Leu Leu Ile Ala Val
            500                 505                 510

Gly Val Gly Val Leu Ile Tyr Val Tyr Leu Ile Leu Lys Thr Arg Leu
        515                 520                 525

Ala Asp Leu Ile Ile Gly Glu Arg Ile Ser Arg Leu Arg Asp Ile Leu
    530                 535                 540

His Ile Arg
545
```

<210> SEQ ID NO 103
<211> LENGTH: 1062
<212> TYPE: DNA
<213> ORGANISM: Lactobacillus casei

<400> SEQUENCE: 103

```
atggcagatc ctgaagcgct gatctcggtt atcatgccag tctacaatgc agagaagtat      60
ctcgcagagg ccttggacag tttattggca caagattatc gaattatga gattatttgt     120
gtagacgatg gttccatgga taccagtaaa gttatcttgg cggcttatat gcgagaaaat     180
ccccgaattc acgttgtgcg ggttcaaaat ggcggtcaag cacgggctcg gcaaattggg     240
attgatcatg ccaacgggga cttgatcacg tttatggata gcgacgatct tgtgcatccg     300
cagtggctat ccaccatggc agacgggatg aaggcaccac gggtcgatat ggtggttgtc     360
aattattaca actacattgg cagtacgaag atgaaggcac gcgcgtttcg tgaatcgaca     420
tttaaaatcg aaggcgatga caagtatcgc tattggttag aggatcgtga tttgcgcggt     480
tatttgtgga ataaattatt ccgtgccgag ttattcgaac cgcctgtgcc tgtcgcgaat     540
ttcaatttgt tagaggatgc ttactttatc ggccatcttt tgccgcgaat tgatcaaatc     600
ggcttcattg acgaacctcg gtattattat cggttcaatg cgaccagcag tgtgcacgcc     660
aagtttcaaa agcgtgattt agaagcaatc catcaactcg cgccgtttt cctgaccctc     720
gcgcatgaca aaccggaatt gacctcgctg gcagtgcgcc gttatgcggc cctgagtcta     780
tttgtgttat caaaaatgtc accacgtcag cttgttaaaa attggggtta tgtccgtcag     840
cttgggatgg tactggggca atataccccg gagtttcaag atgtcatctc ggcaggcgat     900
gtcaacgatt tagcgacaga aaatccagac aagcccaata aaacgagcct gacaggcagg     960
ttgcgcgcat ggtcgcagtt gctgggcttg ccgaccttcg atgacttgaa taagcttgcc    1020
aaggcggatg atgatccaga agatgtgaaa agagaatctt ag                      1062
```

<210> SEQ ID NO 104
<211> LENGTH: 353
<212> TYPE: PRT
<213> ORGANISM: Lactobacillus casei

```
<400> SEQUENCE: 104

Met Ala Asp Pro Glu Ala Leu Ile Ser Val Ile Met Pro Val Tyr Asn
1               5                   10                  15

Ala Glu Lys Tyr Leu Ala Glu Ala Leu Asp Ser Leu Leu Ala Gln Asp
            20                  25                  30

Tyr Pro Asn Tyr Glu Ile Ile Cys Val Asp Asp Gly Ser Met Asp Thr
        35                  40                  45

Ser Lys Val Ile Leu Ala Ala Tyr Met Arg Glu Asn Pro Arg Ile His
    50                  55                  60

Val Val Arg Val Gln Asn Gly Gly Gln Ala Arg Ala Arg Gln Ile Gly
65                  70                  75                  80

Ile Asp His Ala Asn Gly Asp Leu Ile Thr Phe Met Asp Ser Asp Asp
                85                  90                  95

Leu Val His Pro Gln Trp Leu Ser Thr Met Ala Asp Gly Met Lys Ala
            100                 105                 110

Pro Arg Val Asp Met Val Val Val Asn Tyr Tyr Asn Tyr Ile Gly Ser
        115                 120                 125

Thr Lys Met Lys Ala Arg Ala Phe Arg Glu Ser Thr Phe Lys Ile Glu
    130                 135                 140

Gly Asp Asp Lys Tyr Arg Tyr Trp Leu Glu Asp Arg Asp Leu Arg Gly
145                 150                 155                 160

Tyr Leu Trp Asn Lys Leu Phe Arg Ala Glu Leu Phe Glu Pro Pro Val
                165                 170                 175

Pro Val Ala Asn Phe Asn Leu Leu Glu Asp Ala Tyr Phe Ile Gly His
            180                 185                 190

Leu Leu Pro Arg Ile Asp Gln Ile Gly Phe Ile Asp Glu Pro Arg Tyr
        195                 200                 205

Tyr Tyr Arg Phe Asn Ala Thr Ser Ser Val His Ala Lys Phe Gln Lys
    210                 215                 220

Arg Asp Leu Glu Ala Ile His Gln Leu Gly Ala Val Phe Leu Thr Leu
225                 230                 235                 240

Ala His Asp Lys Pro Glu Leu Thr Ser Leu Ala Val Arg Arg Tyr Ala
                245                 250                 255

Ala Leu Ser Leu Phe Val Leu Ser Lys Met Ser Pro Arg Gln Leu Val
            260                 265                 270

Lys Asn Trp Gly Tyr Val Arg Gln Leu Gly Met Val Leu Gly Gln Tyr
        275                 280                 285

Thr Arg Glu Phe Gln Asp Val Ile Ser Ala Gly Asp Val Asn Asp Leu
    290                 295                 300

Ala Thr Glu Asn Pro Asp Lys Pro Asn Lys Thr Ser Leu Thr Gly Arg
305                 310                 315                 320

Leu Arg Ala Trp Ser Gln Leu Leu Gly Leu Pro Thr Phe Asp Asp Leu
                325                 330                 335

Asn Lys Leu Ala Lys Ala Asp Asp Pro Glu Asp Val Lys Arg Glu
            340                 345                 350

Ser

<210> SEQ ID NO 105
<211> LENGTH: 930
<212> TYPE: DNA
<213> ORGANISM: Lactobacillus casei
```

-continued

<400> SEQUENCE: 105

```
atgccgcaaa gtgtggcaat tatcattcca tgtcataacg agtcagaaaa tgtcccgctg      60
atctatcaag aacttgttaa acattccgc gacaacttaa ccgcgttaca agcgcaaatt     120
tggtttgtca acgacggttc aagcgacgat acccttcagc aaatcaaaca gttacaagca     180
aaagacgatc aggttcactt cattgatctt tctcgctcgt ttggtaagga ggcggccatg     240
tatgctggtc tctccaccgc aaaagcagac tactacgccg ttatggatgc tgatctgcaa     300
gacccgccag cgatgcttcc tgatatgtat gccgccttgc aagacggcta tgatatggct     360
ggtgctcaac gcactgaccg ctcaggcgaa gctcggatgc gttcattttt ctcggattta     420
ttctataaat tcattaataa agtctcgcaa actcaaattg taccaggggc acgggatttc     480
cgcttgatga cgagacaggt tgtcgaagct gtcattcaaa tgaccgagcg caaccgcttc     540
tctaaagggc tattcagttg ggttgggttc aaaacaaagt atctgcctta cgcaacatc     600
gagcgtcaac atggggagac gagctggtcc ttcatgggc tcttgcgata cgcgcttgat     660
ggcatcatcg acttctctga agcaccgtta accttcgtgt ccattcttgg tatcgtgagt     720
ttcgttggct cgttttttgc tttaatcttc attgttttc gcgcagctat ttacggtgat     780
ccgaccgctg gctggccgtc aatggtctct atctttctga tgatcggcgg cctccagttg     840
ttcgccctcg cattcgttgg ccgctacatc ggccgcattt acttagaaac aaacgacgc     900
ccgattttta tcgcacgtga gatcaagtaa                                      930
```

<210> SEQ ID NO 106
<211> LENGTH: 309
<212> TYPE: PRT
<213> ORGANISM: Lactobacillus casei

<400> SEQUENCE: 106

```
Met Pro Gln Ser Val Ala Ile Ile Pro Cys His Asn Glu Ser Glu
1               5                   10                  15

Asn Val Pro Leu Ile Tyr Gln Glu Leu Val Lys Thr Phe Arg Asp Asn
                20                  25                  30

Leu Thr Ala Leu Gln Ala Gln Ile Trp Phe Val Asn Asp Gly Ser Ser
            35                  40                  45

Asp Asp Thr Leu Gln Gln Ile Lys Gln Leu Gln Ala Lys Asp Asp Gln
        50                  55                  60

Val His Phe Ile Asp Leu Ser Arg Ser Phe Gly Lys Glu Ala Ala Met
65                  70                  75                  80

Tyr Ala Gly Leu Ser Thr Ala Lys Ala Asp Tyr Ala Val Met Asp
                85                  90                  95

Ala Asp Leu Gln Asp Pro Pro Ala Met Leu Pro Asp Met Tyr Ala Ala
            100                 105                 110

Leu Gln Asp Gly Tyr Asp Met Ala Gly Ala Gln Arg Thr Asp Arg Ser
        115                 120                 125

Gly Glu Ala Arg Met Arg Ser Phe Phe Ser Asp Leu Phe Tyr Lys Phe
    130                 135                 140

Ile Asn Lys Val Ser Gln Thr Gln Ile Val Pro Gly Ala Arg Asp Phe
145                 150                 155                 160

Arg Leu Met Thr Arg Gln Val Val Glu Ala Val Ile Gln Met Thr Glu
                165                 170                 175

Arg Asn Arg Phe Ser Lys Gly Leu Phe Ser Trp Val Gly Phe Lys Thr
            180                 185                 190

Lys Tyr Leu Pro Tyr Arg Asn Ile Glu Arg Gln His Gly Glu Thr Ser
        195                 200                 205
```

```
Trp Ser Phe Met Gly Leu Leu Arg Tyr Ala Leu Asp Gly Ile Ile Asp
    210                 215                 220

Phe Ser Glu Ala Pro Leu Thr Phe Val Ser Ile Leu Gly Ile Val Ser
225                 230                 235                 240

Phe Val Gly Ser Phe Phe Ala Leu Ile Phe Ile Val Phe Arg Ala Ala
                245                 250                 255

Ile Tyr Gly Asp Pro Thr Ala Gly Trp Pro Ser Met Val Ser Ile Phe
                260                 265                 270

Leu Met Ile Gly Gly Leu Gln Leu Phe Ala Leu Gly Ile Val Gly Arg
        275                 280                 285

Tyr Ile Gly Arg Ile Tyr Leu Glu Thr Lys Arg Arg Pro Ile Phe Ile
    290                 295                 300

Ala Arg Glu Ile Lys
305

<210> SEQ ID NO 107
<211> LENGTH: 1545
<212> TYPE: DNA
<213> ORGANISM: Lactobacillus casei

<400> SEQUENCE: 107
```

| | | | | | |
|---|---|---|---|---|---|
| atgggggaaa | atatgataaa | cgagtcacaa | aagttcttaa | actttctcaa | aaaaaagcga | 60 |
| aaggctgtct | cattcttatt | tgcagttaca | ttattacttt | atctaccaat | gctcacaaac | 120 |
| ttcagctatt | cgattgattc | cgaggccgtt | gtcgacaatt | ctaaagactt | actattttca | 180 |
| tggctgacaa | ttgaccgctt | tggactggta | gcgctcaaaa | aattcttttt | gttcggcctt | 240 |
| gaccttaatc | catattttat | taatacgctg | acctacctct | taatggcatt | tagcgcagtc | 300 |
| attcttctat | acataatcga | tcaactgatt | caaacaactc | catggattcc | tttgctcgcg | 360 |
| gtcaccttat | acctcgtttc | gccaatccac | ttcgagcaaa | atagttttgt | gttacaaagt | 420 |
| gttgaagtta | tgattggttt | taacttgatg | tttgtcggaa | tgattgcgtt | aggtatgcca | 480 |
| ggaaataagg | tttcacccaa | gcgtctcatt | tttggtatgc | tattccttac | tgcaagcttt | 540 |
| tcaatatatc | cttctattgt | cattggcgca | tcaacattgg | ccatcattat | tcttcactta | 600 |
| cacgaactaa | acaaaccatt | tgcaaccttc | tccgtctatt | ttagacatct | tgttcggtac | 660 |
| attgcactaa | tcttaagcag | tttgctgacc | tatgtggcgc | tcgaccaaat | catcaaatat | 720 |
| tttgctcatg | caccaaagaa | tagctatatt | caaacagcat | ggggacatat | ggatacttct | 780 |
| cttctcatgc | aaatcgcatt | ggccaagttt | aaacagtttt | ttatttttcc | aaatcaacct | 840 |
| tttgaactct | cggttgtaac | atatttggca | gtagtaacat | tcgctcttgt | tttaataatg | 900 |
| ggattaatcc | gtaagcagat | tcgttggaca | attttattgg | acattatcgc | tgagtatatt | 960 |
| ttggttctca | gcttattgat | cctacttggc | aacatgattg | gacctattcg | ttcactgacc | 1020 |
| cctaccgtgc | cgttagtcat | gattgtttat | agcctgacag | tcatgaccat | gatgccaaac | 1080 |
| aaacgcctac | tcttggttgt | cggcatgagc | ttctcaattt | ttgcgcttat | gctgagcaag | 1140 |
| acaacttctg | atctagaaca | aagtttcatc | atcagttatg | aaaacgaagt | aaagttctca | 1200 |
| gacaaaattg | tcaccagcgt | tcaggaatta | ggcattaaca | actttgatca | gtatagatta | 1260 |
| gtcattgttg | gagaaaagag | attcaattct | cctttaactg | aaatgggaga | atgattggc | 1320 |
| aatactcatt | ataactggga | tcttgactcg | ccaacaggaa | gcaatcgccg | cgtgaccaat | 1380 |
| tttctttcat | cacaaggtta | caaatttgca | actgttagtc | ctaccgatta | tcgcaaagcg | 1440 |
| caaagaataa | gtttgaaaat | gaaacattc | cctgccaagg | tggtataaaa | gattttgggt | 1500 |
| aaaatgatcg | tcgtaaactt | aaagaatacg | gacatagtta | actga | | 1545 |

<210> SEQ ID NO 108
<211> LENGTH: 514
<212> TYPE: PRT
<213> ORGANISM: Lactobacillus casei

<400> SEQUENCE: 108

```
Met Gly Glu Asn Met Ile Asn Glu Ser Gln Lys Phe Leu Asn Phe Leu
1               5                   10                  15

Lys Lys Lys Arg Lys Ala Val Ser Phe Leu Phe Ala Val Thr Leu Leu
            20                  25                  30

Leu Tyr Leu Pro Met Leu Thr Asn Phe Ser Tyr Ser Ile Asp Ser Glu
        35                  40                  45

Ala Val Val Asp Asn Ser Lys Asp Leu Leu Phe Ser Trp Leu Thr Ile
    50                  55                  60

Asp Arg Phe Gly Leu Val Ala Leu Lys Lys Phe Phe Leu Phe Gly Leu
65                  70                  75                  80

Asp Leu Asn Pro Tyr Phe Ile Asn Thr Leu Thr Tyr Leu Leu Met Ala
                85                  90                  95

Phe Ser Ala Val Ile Leu Leu Tyr Ile Ile Asp Gln Leu Ile Gln Thr
            100                 105                 110

Thr Pro Trp Ile Pro Leu Leu Ala Val Thr Leu Tyr Leu Val Ser Pro
        115                 120                 125

Ile His Phe Glu Gln Asn Ser Phe Val Leu Gln Ser Val Glu Val Met
130                 135                 140

Ile Gly Phe Asn Leu Met Phe Val Gly Met Ile Ala Leu Gly Met Pro
145                 150                 155                 160

Gly Asn Lys Val Ser Pro Lys Arg Leu Ile Phe Gly Met Leu Phe Leu
                165                 170                 175

Thr Ala Ser Phe Ser Ile Tyr Pro Ser Ile Val Ile Gly Ala Ser Thr
            180                 185                 190

Leu Ala Ile Ile Ile Leu His Leu His Glu Leu Asn Lys Pro Phe Ala
        195                 200                 205

Thr Phe Ser Val Tyr Phe Arg His Leu Val Arg Tyr Ile Ala Leu Ile
    210                 215                 220

Leu Ser Ser Leu Leu Thr Tyr Val Ala Leu Asp Gln Ile Ile Lys Tyr
225                 230                 235                 240

Phe Ala His Ala Pro Lys Asn Ser Tyr Ile Gln Thr Ala Trp Gly His
                245                 250                 255

Met Asp Thr Ser Leu Leu Met Gln Ile Ala Leu Ala Lys Phe Lys Gln
            260                 265                 270

Phe Phe Ile Phe Pro Asn Gln Pro Phe Glu Leu Ser Val Val Thr Tyr
        275                 280                 285

Leu Ala Val Val Thr Phe Ala Leu Val Leu Ile Met Gly Leu Ile Arg
    290                 295                 300

Lys Gln Ile Arg Trp Thr Ile Leu Leu Asp Ile Ile Ala Glu Tyr Ile
305                 310                 315                 320

Leu Val Leu Ser Leu Leu Ile Leu Gly Asn Met Ile Gly Pro Ile
                325                 330                 335

Arg Ser Leu Thr Pro Thr Val Pro Leu Val Met Ile Val Tyr Ser Leu
            340                 345                 350

Thr Val Met Thr Met Met Pro Asn Lys Arg Leu Leu Leu Val Val Gly
        355                 360                 365

Met Ser Phe Ser Ile Phe Ala Leu Met Leu Ser Lys Thr Thr Ser Asp
    370                 375                 380
```

-continued

```
Leu Glu Gln Ser Phe Ile Ile Ser Tyr Glu Asn Glu Val Lys Phe Ser
385                 390                 395                 400

Asp Lys Ile Val Thr Ser Val Gln Glu Leu Gly Ile Asn Asn Phe Asp
                405                 410                 415

Gln Tyr Arg Leu Val Ile Val Gly Glu Lys Arg Phe Asn Ser Pro Leu
            420                 425                 430

Thr Glu Met Gly Glu Met Ile Gly Asn Thr His Tyr Asn Trp Asp Leu
        435                 440                 445

Asp Ser Pro Thr Gly Ser Asn Arg Arg Val Thr Asn Phe Leu Ser Ser
    450                 455                 460

Gln Gly Tyr Lys Phe Ala Thr Val Ser Pro Thr Asp Tyr Arg Lys Ala
465                 470                 475                 480

Gln Arg Ile Ser Leu Lys Met Lys Thr Phe Pro Ala Lys Gly Gly Ile
            485                 490                 495

Lys Ile Leu Gly Lys Met Ile Val Val Asn Leu Lys Asn Thr Asp Ile
            500                 505                 510

Val Asn
```

CYTOKINE PRODUCTION REGULATOR GENE AND USE THEREOF

CROSS-REFERENCE TO RELATED APPLICATIONS

The present application is a 35 U.S.C. §371 National Stage patent application of International patent application PCT/JP2007/001176, filed on Oct. 26, 2007, which claims priority to Japanese patent application JP 2006-292934, filed on Oct. 27, 2006.

TECHNICAL FIELD

The present invention relates to a gene involved in regulation of cytokine production from macrophages and/or immunocompetent cells, and to use of the gene.

BACKGROUND ART

Cytokines such as TNFs, interleukins, and interferons are intercellular signaling substances which play an important role in a biological defense system such as an immune system, a blood system, or an inflammatory response.

Immune response is triggered through recognition of a substance stimulating cytokine production by a pattern recognition receptor (PRR) (e.g., toll-like receptor (TLR)) whose expression is observed in host immunocytes, particularly in, for example, macrophages or dendritic cells. Immune response is regulated through direct or indirect interaction between immunocompetent cells (e.g., macrophages, dendritic cells, or lymphocytes).

Generally, living organisms cope with, for example, bacterial or viral infection, tumor, or cytotoxicity through activation of immune response. As has been shown, induction of excessive immune response may cause an allergic disease such as atopic dermatitis, bronchial asthma, allergic rhinitis, allergic conjunctivitis, or food allergy, or an autoimmune disease such as systemic lupus erythematosus (SLE) or chronic rheumatoid arthritis. Therefore, it is important that cytokine production in a living organism can be regulated so as to achieve a more desirable state.

In recent years, attempts have been made to use a microorganism or a microorganism-derived component as a cytokine-production-regulating substance; i.e., a biological response modifier (BRM). Hitherto, there have been reported, for example, the cytokine production promoting effect of a polysaccharide-glycan complex derived from a Gram-positive bacterium (Patent Document 1), the interleukin (IL)-6 production inhibitory effect of a polysaccharide fraction derived from a bacterium belonging to the genus *Lactobacillus* or cells thereof (Patent Document 2), the IL-15 production promoting effect of *lactobacillus* cells (Patent Document 3), the IL-12 production promoting effect of cells of *Lactobacillus casei*, etc. (Patent Document 4), the macrophage activation effect of a polysaccharide-peptidoglycan complex derived from a bacterium belonging to the genus *Lactobacillus* (Patent Document 5), and the tumor cytotoxic factor inducing effect of a polysaccharide-peptidoglycan complex derived from a bacterium belonging to the genus *Lactobacillus* (Patent Document 6).

As has been shown, in the cytokine production regulatory effect of *Lactobacillus casei* YIT 9018 (FERM BP-665) or *Lactobacillus casei* YIT 9029 (FERM BP-1366), a polysaccharide-peptidoglycan complex (PS-PG) (i.e., a cell wall component) serves as an active center (Patent Document 2). However, elucidation at the genetic level has not yet been accomplished.

As has been reported, attempts have been made to modify the cytokine production regulatory activity of a microorganism at the genetic level by introducing the listeriolysin O gene, which is a listerial hemolysin, into *Lactobacillus casei* ATCC 393 (Patent Document 7). However, this modification causes problems in terms of safety or effectiveness and thus has not yet been put into practice. There has also been reported a gene involved in biosynthesis of an exopolysaccharide which is extracellularly produced by lactic acid bacterium (Patent Document 8). However, this exopolysaccharide is provided for the purpose of thickening foods or making foods creamy, and the exopolysaccharide has a structure different from that of a polysaccharide contained in the aforementioned PS-PG.

Patent Document 1: JP-A-1996-92112
Patent Document 2: JP-A-2003-73286
Patent Document 3: JP-A-2002-241292
Patent Document 4: JP-A-1998-139674
Patent Document 5: JP-B-1994-99314
Patent Document 6: JP-A-1988-196521
Patent Document 7: JP-A-2003-63991
Patent Document 8: JP-A-1997-269

DISCLOSURE OF THE INVENTION

Problems to be Solved by the Invention

The present invention provides a gene involved in regulation of cytokine production from macrophages and/or immunocompetent cells and use of the gene.

Means for Solving the Problems

The present inventors have conducted studies on the genomic information of *Lactobacillus casei* YIT 9029, and as a result have found that a gene involved in regulation of production of various cytokines is present among genes involved in synthesis of a polysaccharide component of a polysaccharide-peptidoglycan complex (PS-PG), and that production of various cytokines can be regulated through use of the gene in a microorganism.

Accordingly, the present invention provides the following.
1) A gene encoding a protein selected from among the following proteins (a) to (c):
   (a) a protein having any of the amino acid sequences of SEQ ID NOs: 2, 4, 6, 8, 10, 12, 14, 16, 82, 84, 86, 88, 90, 92, 94, 96, 98, 100, 102, 104, 106, and 108;
   (b) a protein which has an amino acid sequence equivalent to any of the amino acid sequences of (a), except that one to several amino acid residues are deleted, substituted, or added, and which exhibits cytokine production regulatory activity; and
   (c) a protein which has an amino acid sequence having 90% or higher identity to any of the amino acid sequences of (a), and which exhibits cytokine production regulatory activity.
2) A gene having a polynucleotide selected from among the following polynucleotides (d) to (f):
   (d) a polynucleotide having any of the nucleotide sequences of SEQ ID NOs: 1, 3, 5, 7, 9, 11, 13, 15, 81, 83, 85, 87, 89, 91, 93, 95, 97, 99, 101, 103, 105, and 107;
   (e) a polynucleotide which hybridizes, under stringent conditions, with a polynucleotide having a nucleotide sequence complementary to any of the nucleotide sequences of (d), and which encodes a protein exhibiting cytokine production regulatory activity; and (f) a polynucleotide which has a nucleotide sequence having 90% or higher identity to any of the nucleotide sequences of (d), and which encodes a protein exhibiting cytokine production regulatory activity.

3) A method for regulating cytokine production in a microorganism, comprising introducing any of the aforementioned genes into the microorganism, or modifying the gene present in the microorganism.

4) A microorganism in which any of the aforementioned genes has been introduced or modified.

5) A food or beverage containing the aforementioned microorganism.

6) A drug containing the aforementioned microorganism.

7) A screening method for selecting a microorganism exhibiting cytokine production regulatory activity, comprising determining the presence or absence of any of the aforementioned genes, and/or determining the level of expression of the gene.

8) A recombinant vector containing any of the aforementioned polynucleotides or a portion thereof.

9) A host microorganism containing the aforementioned recombinant vector.

10) A nucleic acid fragment which specifically hybridizes with any of the aforementioned polynucleotides.

11) A DNA array or DNA chip containing any of the aforementioned polynucleotides or a portion thereof.

Effects of the Invention

Employment of the gene or polynucleotide of the present invention or a fragment thereof realizes regulation of cytokine production from macrophages and/or immunocompetent cells in a microorganism as desired, or selection, through screening, of a microorganism exhibiting cytokine production regulatory activity of interest.

Employment of a microorganism in which the gene of the present invention has been introduced or modified realizes production of a food, beverage, or drug exhibiting cytokine production regulatory activity of interest.

BEST MODES FOR CARRYING OUT THE INVENTION

Figure 1:
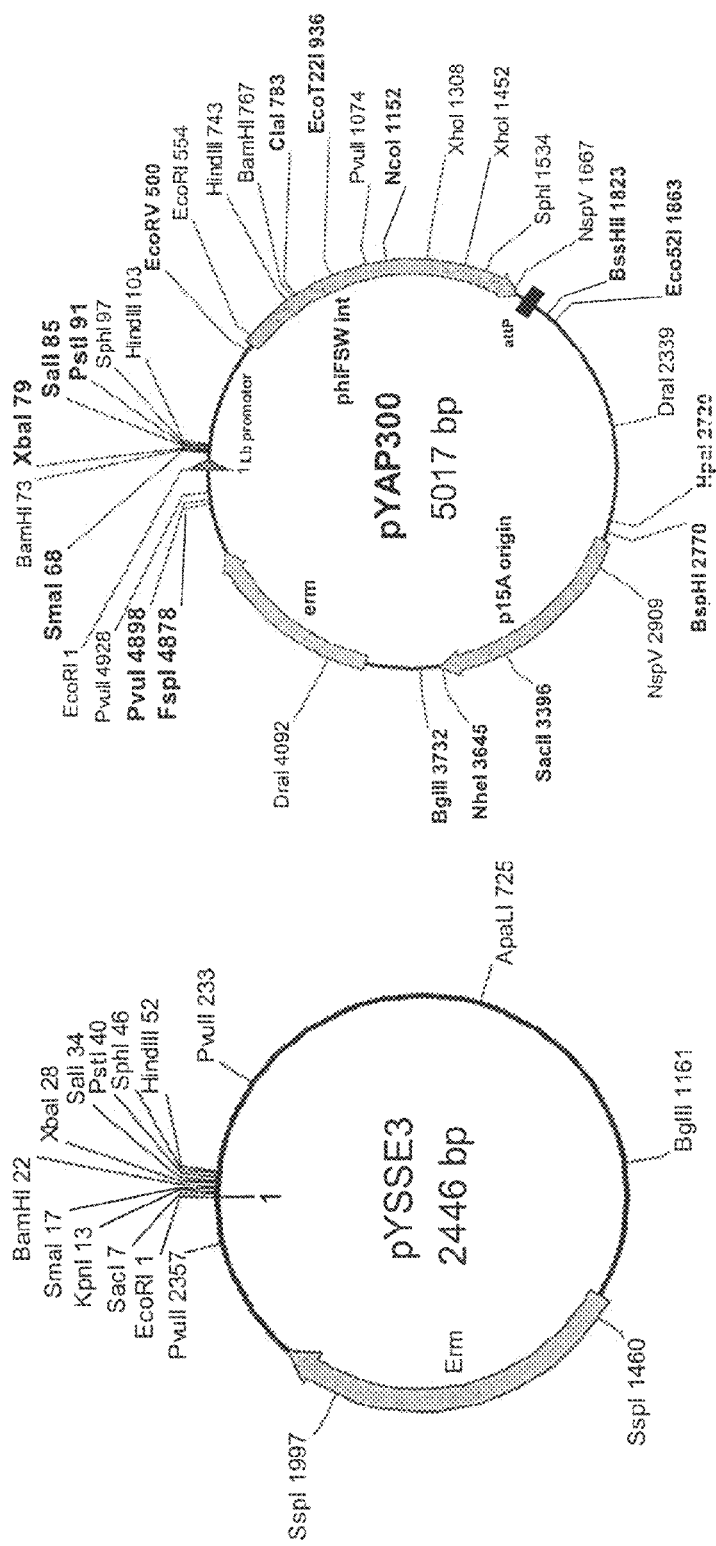
FIG. 1 shows pYSSE3 and pYAP300.
Figure 2:
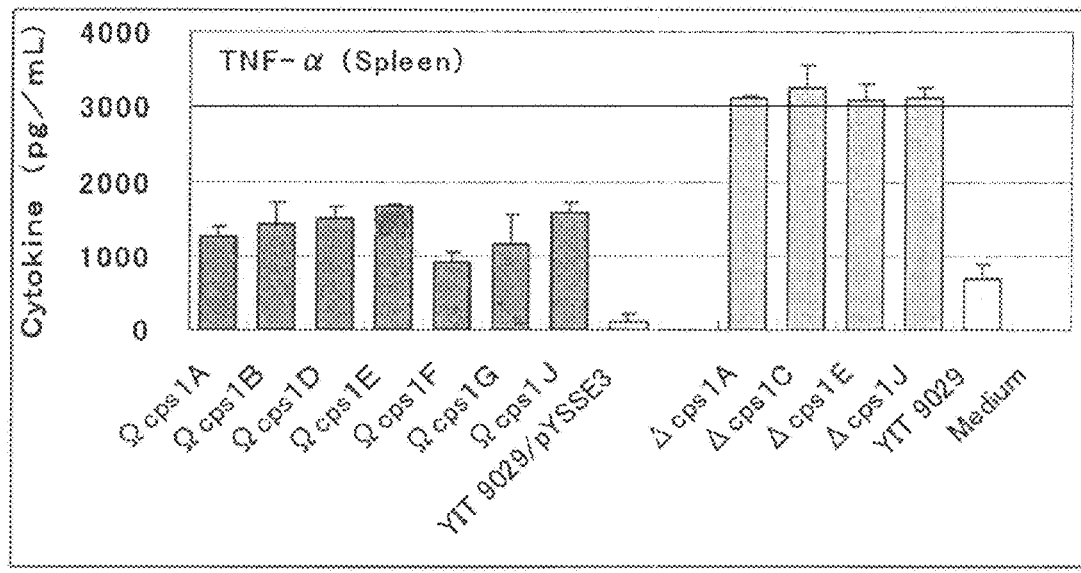
FIG. 2 shows the TNF-α inducibility of gene-disrupted strains of *Lactobacillus casei* YIT 9029 in BALB/c mouse spleen cells (amount of bacterial cells added: 3 μg/mL).
Figure 3:
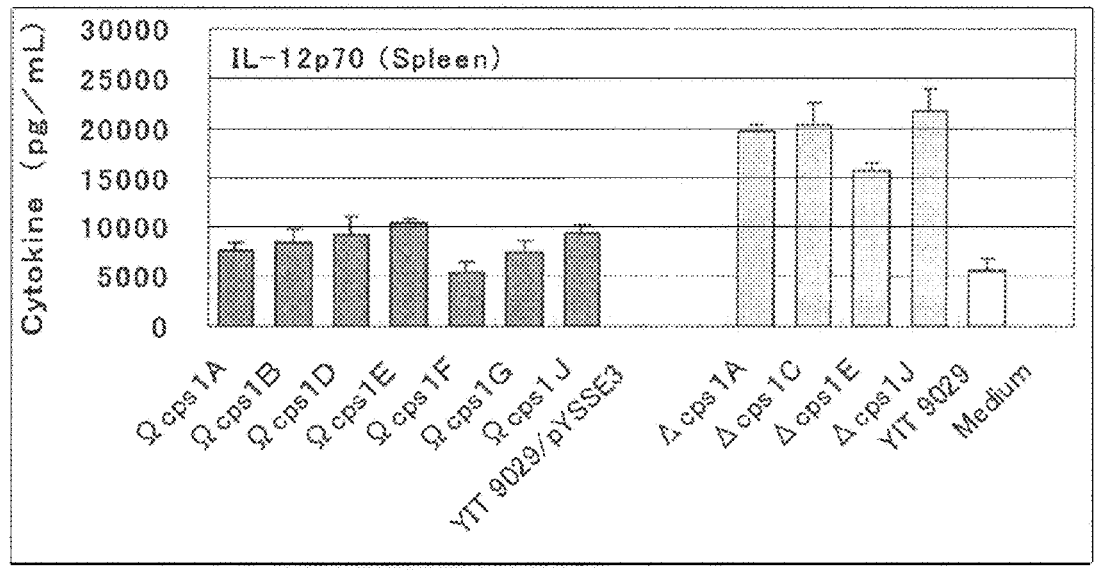
FIG. 3 shows the IL-12p70 inducibility of gene-disrupted strains of *Lactobacillus casei* YIT 9029 in BALB/c mouse spleen cells (amount of bacterial cells added: 3 μg/mL).
Figure 4:
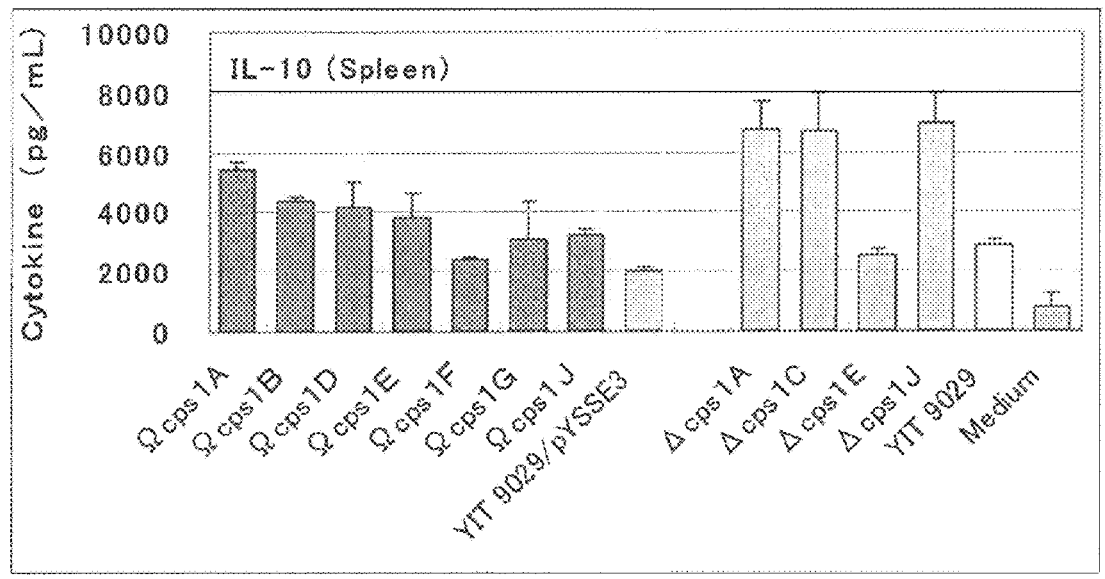
FIG. 4 shows the IL-10 inducibility of gene-disrupted strains of *Lactobacillus casei* YIT 9029 in BALB/c mouse spleen cells (amount of bacterial cells added: 30 μg/mL).
Figure 5:
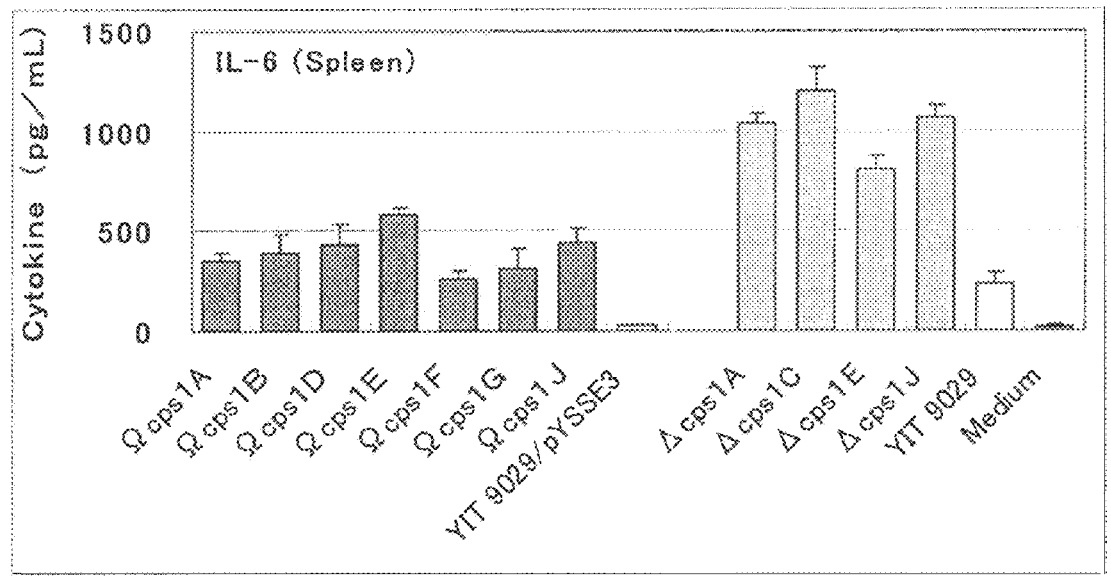
FIG. 5 shows the IL-6 inducibility of gene-disrupted strains of *Lactobacillus casei* YIT 9029 in BALB/c mouse spleen cells (amount of bacterial cells added: 3 μg/mL).

In the present invention, homology (identity) between amino acid sequences and that between nucleotide sequences may be determined through the Lipman-Pearson method (Lipman, D. J. and Pearson, W. R. 1985. Rapid and sensitive protein similarity searches. Science 227: 1435-1441) by use of genetic information processing software GENETYX (product of Genetyx Corporation) employing a homology analysis (search homology) program. Specifically, homology (%) is calculated through analysis of data on comparison between a gene involved in PS-PG synthesis by *Lactobacillus casei* YIT 9029 and a known gene for polysaccharide synthesis (parameters are as follows: unit size to compare=2, pick up location=5).

As used herein, the term "gene" refers to a double-stranded DNA fragment, as well as a single-stranded DNA fragment (e.g., a sense or antisense fragment) which forms such a double-stranded DNA fragment. No particular limitation is imposed on the length of such a DNA fragment. Examples of the polynucleotide include RNA and DNA fragments, and examples of DNA fragments include cDNA, genomic DNA, and synthetic DNA fragments.

The gene of the present invention is a gene found in *Lactobacillus casei* YIT 9029 and named cps1A, cps1B, cps1C, cps1D, cps1E, cps1F, cps1G, cps1J, cps2A, cps2C, cps2D, cps2E, cps2F, cps2G, cps2H, cps3A, cps3B, or cps3C, a gene represented by a gene number of LCS0838, LCS1111, LCS1128, or LCS1890, or a gene deduced from any of these genes. The gene of the present invention encodes a protein having a function of promoting or inhibiting cytokine production from macrophages and/or immunocompetent cells. All of the aforementioned genes are novel genes, since a polynucleotide having 90% or higher identity in sequence to any of the genes has not been found through homology search between these genes and genes registered in existing databases.

Specifically, the gene of the present invention is a gene encoding a protein selected from among the following proteins (a) to (c):

(a) a protein having any of the amino acid sequences of SEQ ID NOs: 2, 4, 6, 8, 10, 12, 14, 16, 82, 84, 86, 88, 90, 92, 94, 96, 98, 100, 102, 104, 106, and 108;

(b) a protein which has an amino acid sequence equivalent to any of the amino acid sequences of (a), except that one to several amino acid residues are deleted, substituted, or added, and which exhibits cytokine production regulatory activity; and (c) a protein which has an amino acid sequence having 90% or higher identity to any of the amino acid sequences of (a), and which exhibits cytokine production regulatory activity.

The amino acid sequence of any of SEQ ID NOs: 2, 4, 6, 8, 10, 12, 14, 16, 82, 84, 86, 88, 90, 92, 94, 96, 98, 100, 102, 104, 106, and 108 in which one or more amino acid residues are deleted, substituted, or added encompasses an amino acid sequence obtained through deletion, substitution, or addition of one to several amino acid residues (preferably 1 to 10 amino acid residues). As used herein, "addition" encompasses addition of one to several amino acid residues to both ends of an amino acid sequence.

As used herein, "deletion, substitution, or addition of an amino acid residue(s)" encompasses deletion, substitution, or addition of an amino acid residue(s) in a protein having an amino acid sequence of, for example, SEQ ID NO: 2, resulting from, for example, naturally occurring mutation (e.g., single nucleotide substitution) or artificial mutation (e.g., site-directed mutagenesis or mutagenic treatment). In the case of artificial deletion, substitution, or addition of an amino acid residue(s), for example, a polynucleotide having a nucleotide sequence encoding an amino acid sequence of, for example, SEQ ID NO: 2 is subjected to a conventional site-directed mutagenesis, followed by expression of the polynucleotide through a customary method.

Amino acid residue substitution may be, for example, substitution by an amino acid residue exhibiting properties (e.g., hydrophobicity, electric charge, pK, and conformational feature) similar to those of the original amino acid residue.

The expression "amino acid sequence having 90% or higher identity to any of the amino acid sequences of (a)" refers to an amino acid sequence which, upon appropriate alignment, exhibits 90% or higher identity (more preferably 95% or higher) to any of the amino acid sequences of SEQ ID NOs: 2, 4, 6, 8, 10, 12, 14, 16, 82, 84, 86, 88, 90, 92, 94, 96, 98, 100, 102, 104, 106, and 108.

As used herein, the expression "cytokine production regulatory activity" refers to promotion or inhibition of production of a cytokine(s) from macrophages and/or immunocompetent cells. This expression also encompasses the case where a single gene exhibits the effect of promoting or suppressing production of different cytokines.

No particular limitation is imposed on the cytokine. Examples of the cytokine include interferons such as IFN-α, IFN-β, and IFN-γ; interleukins such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, and IL-29; tumor necrosis factors such as TNF-α and TNF-β; chemokines such as CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CL1, CL2, $CX_3CL$, MCP, MIP, RANTES, and Eotaxin; colony-stimulating factors such as GM-CSF, G-CSF, and M-CSF; growth factors such as EGF, PDGF, FGF, NGF, VEGF, TGF, KGF, IGF, SCF, BDNF, CNTF, OSM, and IIGF; thrombopoietin (TPO); stem cell factor (SCF); leukemia inhibitory factor (LIF); prolactine hormone; BMP; activin; leptin; adiponectin; prostaglandins (PG); and nitrogen monoxide (NO).

As used herein, the term "immunocompetent cell" refers to a cell involved in immune response. No particular limitation is imposed on the immunocompetent cell, and examples of the immunocompetent cell include macrophages, dendritic cells, Langerhans cells, monocytes, T-cells, B-cells, natural killer cells, and natural killer T-cells.

Next will be described the homology (identity) between known proteins and a protein having any of the amino acid sequences of SEQ ID NOs: 2, 4, 6, 8, 10, 12, 14, 16, 82, 84, 86, 88, 90, 92, 94, 96, 98, 100, 102, 104, 106, and 108. For homology search, by use of genetic information processing software GENETYX, the amino acid sequence of a protein defined by any of the aforementioned nucleotide sequences was compared with the amino acid sequence of a protein defined generally by a disclosed nucleotide sequence of the genome or a DNA fragment of lactic acid bacteria, to thereby search for genes having homology. When the entire amino acid sequence or a portion thereof having a maximum possible length of a protein has 20% or higher identity to that of the corresponding protein, these proteins are regarded as having homology.

The protein having the amino acid sequence of SEQ ID NO: 2 (Cps1A) has 37.5% identity in amino acid sequence to a protein encoded by the epsB gene derived from *Lactobacillus delbrueckii* subsp. *bulgaricus* Lfi5 strain and involved in exopolysaccharide synthesis. The protein Cps1A has 30.9% identity in amino acid sequence to a protein encoded by the epsA gene derived from *Lactococcus lactis* subsp. *cremoris* HO2 strain and involved in exopolysaccharide synthesis. The protein Cps1A has 70.2% identity in amino acid sequence to a protein encoded by the wzd gene derived from *Lactobacillus rhamnosus* RW-9595M and involved in exopolysaccharide synthesis. The protein Cps1A has 40.6% identity in amino acid sequence to a protein predicted by the draft sequence of *Lactobacillus gasseri* ATCC 33323 (JGI).

The protein having the amino acid sequence of SEQ ID NO: 4 (Cps1B) has 46.4% identity in amino acid sequence to a protein encoded by the epsC gene derived from *Lactobacillus delbrueckii* subsp. *bulgaricus* Lfi5 strain and involved in exopolysaccharide synthesis. The protein Cps1B has 41.7% identity in amino acid sequence to a protein encoded by the epsB gene derived from *Lactococcus lactis* subsp. *cremoris* HO2 strain and involved in exopolysaccharide synthesis. The protein Cps1B has 85.8% identity in amino acid sequence to a protein encoded by the wze gene derived from *Lactobacillus rhamnosus* RW-9595M and involved in exopolysaccharide synthesis. The protein Cps1B has 40.6% identity in amino acid sequence to a protein encoded by the epsC gene derived from *Lactobacillus acidophilus* NCFM and involved in exopolysaccharide synthesis.

The protein having the amino acid sequence of SEQ ID NO: 6 (Cps1C) has 46.3% identity in amino acid sequence to a protein encoded by the rgpA gene derived from *Streptococcus thermophilus* CNRZ1066 and involved in polysaccharide synthesis. The protein Cps1C has 43.4% identity in amino acid sequence to a protein encoded by the rgpA gene derived from *Lactococcus lactis* subsp. *lactis* IL1403 and involved in polysaccharide synthesis.

The protein having the amino acid sequence of SEQ ID NO: 8 (Cps1D) has 43.5% identity in amino acid sequence to a protein encoded by the cpsG gene derived from *Streptococcus salivarius* NCFB2393 and involved in polysaccharide synthesis.

The protein having the amino acid sequence of SEQ ID NO: 10 (Cps1E) has 24.8% identity in amino acid sequence to a protein encoded by the epsN gene derived from *Lactococcus lactis* subsp. *cremoris* HO2 strain and involved in exopolysaccharide synthesis. The protein Cps1E has 22.0% identity in amino acid sequence to a protein encoded by the cps1 gene derived from *Streptococcus salivarius* NCFB2393 and involved in polysaccharide synthesis. The protein Cps1E has 23.0% identity in amino acid sequence to a protein encoded by the ycbH gene derived from *Lactococcus lactis* subsp. *lactis* IL1403 and involved in polysaccharide synthesis.

There was not found a protein having 20% or higher identity in amino acid sequence to the protein having the amino acid sequence of SEQ ID NO: 12 (Cps1F).

The protein having the amino acid sequence of SEQ ID NO: 14 (Cps1G) has 30.6% identity in amino acid sequence to a protein encoded by the thgA2 gene derived from *Lactobacillus plantarum* WCFS1. The protein Cps1G has 39.3% identity in amino acid sequence (in 84 amino acid residues) to a protein encoded by the epsH gene derived from *Streptococcus thermophilus* CNRZ1066 and involved in exopolysaccharide synthesis. The protein Cps1G has 34.5% identity in amino acid sequence (in 116 amino acid residues) to a protein encoded by the yncA gene derived from *Lactococcus lactis* subsp. *lactis* IL1403 and involved in transacetylation.

The protein having the amino acid sequence of SEQ ID NO: 16 (Cps1J) has 58.3% identity in amino acid sequence to a protein encoded by the epsE gene derived from *Lactobacillus delbrueckii* subsp. *bulgaricus* Lfi5 and involved in exopolysaccharide synthesis. The protein Cps1J has 44.1% identity in amino acid sequence to a protein encoded by the epsE gene derived from *Lactobacillus johnsonii* NCC533 and involved in exopolysaccharide synthesis. The protein Cps1J has 79.3% identity in amino acid sequence to a protein encoded by the welE gene derived from *Lactobacillus rhamnosus* RW-9595M and involved in exopolysaccharide synthesis. The protein Cps1J has 65.7% identity in amino acid sequence to a protein encoded by the epsE gene derived from *Lactobacillus acidophilus* NCFM and involved in exopolysaccharide synthesis. The protein Cps1J has 47.5% identity in amino acid sequence to a protein encoded by the epsE gene derived from *Streptococcus thermophilus* FI9186 and involved in exopolysaccharide synthesis. A portion (about 37%) of the amino acid sequence of SEQ ID NO: 16 has 96.7% identity—although the remaining portion has not been elucidated to have such a homology—to the amino acid sequence of a portion of the gene (gene number: 11596438) derived from *Lactobacillus paracasei* Type-V (only a partial sequence thereof has been known) and involved in polysaccharide synthesis.

The protein having the amino acid sequence of SEQ ID NO: 82 (Cps2A) was found to have no homology in amino acid sequence to any of proteins encoded by genes of, for example, other microorganisms.

The protein having the amino acid sequence of SEQ ID NO: 84 (Cps2C) has 38.3% identity in amino acid sequence to a protein (which is considered a glycosyltransferase) encoded by a gene (gene number: EF2195) derived from *Enterococcus faecalis* V583 strain. The protein Cps2C has 34.7% identity in amino acid sequence to a protein encoded by the rgpB gene derived from *Streptococcus mutans* UA159 strain and involved in exopolysaccharide synthesis.

The protein having the amino acid sequence of SEQ ID NO: 86 (Cps2D) has 42.4% identity in amino acid sequence to a protein (which is considered a glycosyltransferase) encoded by a gene (gene number: lp_1763) derived from *Lactobacillus plantarum* WCFS1 strain. The protein Cps2D has 38.3% identity in amino acid sequence to 100 amino acid residues on the amino-terminal side of a protein (which is considered a glycosyltransferase) encoded by a gene (gene number: EF2181) derived from *Enterococcus faecalis* V583 strain.

The protein having the amino acid sequence of SEQ ID NO: 88 (Cps2E) has 35.9% identity in amino acid sequence to a protein (which is considered a glycosyltransferase) encoded by a gene (gene number: LBA0526) derived from *Lactobacillus acidophilus* NCFM strain. The protein Cps2E has 35% identity in amino acid sequence to a protein (which is considered a glycosyltransferase) encoded by a gene (gene number: Ldb0454) derived from *Lactobacillus delbrueckii* subsp. *bulgaricus* ATCC11842 strain.

The protein having the amino acid sequence of SEQ ID NO: 90 (Cps2F) has 51.0% identity in amino acid sequence (in 208 amino acid residues) to a protein (which is considered a muramidase) encoded by a gene (gene number: lp_3093) derived from *Lactobacillus plantarum* WCFS1 strain. The protein Cps2F has 30.7% identity in amino acid sequence (in 326 amino acid residues) to a protein encoded by a gene (gene number: EF2174) derived from *Enterococcus faecalis* V583 strain.

The protein having the amino acid sequence of SEQ ID NO: 92 (Cps2G) has 45.9% identity in amino acid sequence to a protein (which is considered a repeat unit transporter) encoded by a gene (gene number: lp_1231) derived from *Lactobacillus plantarum* WCFS1 strain. The protein Cps2G has 42.6% identity in amino acid sequence to a protein (which is considered a repeat unit transporter) encoded by a gene (gene number: LBA1724) derived from *Lactobacillus acidophilus* NCFM strain.

The protein having the amino acid sequence of SEQ ID NO: 94 (Cps2H) was found to have no homology in amino acid sequence to any of proteins encoded by genes of, for example, other microorganisms.

The protein having the amino acid sequence of SEQ ID NO: 96 (Cps3A) has 66.4% identity in amino acid sequence to a protein (which is considered a glycosyltransferase) encoded by a gene (gene number: lp_1275) derived from *Lactobacillus plantarum* WCFS1 strain. The protein Cps3A has 55.7% identity in amino acid sequence to a protein (which is considered a glycosyltransferase) encoded by a gene (gene number: Ldb1838) derived from *Lactobacillus delbrueckii* subsp. *bulgaricus* ATCC11842 strain.

The protein having the amino acid sequence of SEQ ID NO: 98 (Cps3B) has 59.7% identity in amino acid sequence to a protein (which is considered a glycosyltransferase) encoded by a gene (gene number: lp_1276) derived from *Lactobacillus plantarum* WCFS1 strain. The protein Cps3B has 54.1% identity in amino acid sequence to a protein (which is considered a glycosyltransferase) encoded by a gene (gene number: Ldb1837) derived from *Lactobacillus delbrueckii* subsp. *bulgaricus* ATCC11842 strain.

The protein having the amino acid sequence of SEQ ID NO: 100 (Cps3C) has 49.7% identity in amino acid sequence to a protein (which is considered a glycosyltransferase) encoded by a gene (gene number: lp_1277) derived from *Lactobacillus plantarum* WCFS1 strain. The protein Cps3C has 39.5% identity in amino acid sequence to a protein (which is considered a glycosyltransferase) encoded by a gene (gene number: Ldb1836) derived from *Lactobacillus delbrueckii* subsp. *bulgaricus* ATCC11842 strain.

The protein having the amino acid sequence of SEQ ID NO: 102 (LCS0838P) has 49.9% identity in amino acid sequence to a protein (which is considered a polysaccharide transport protein) encoded by a gene (gene number: Ldb1569) derived from *Lactobacillus delbrueckii* subsp. *bulgaricus* ATCC11842 strain. The protein LCS0838P has 48.9% identity in amino acid sequence to a protein (which is considered a polysaccharide transport protein) encoded by a gene (gene number: LBA1616) derived from *Lactobacillus acidophilus* NCFM strain.

The protein having the amino acid sequence of SEQ ID NO: 104 (LCS1111P) has 30.4% identity in amino acid sequence (in 220 amino acid residues) to a protein (which is considered a glycosyltransferase) encoded by a gene (gene number: EF2176) derived from *Enterococcus faecalis* V583 strain. The protein LCS1111P has 29.9% identity in amino acid sequence (in 224 amino acid residues) to a protein (which is considered a glycosyltransferase) encoded by a gene (gene number: Ldb0178) derived from *Lactobacillus delbrueckii* subsp. *bulgaricus* ATCC11842 strain.

The protein having the amino acid sequence of SEQ ID NO: 106 (LCS1128P) has 53.2% identity in amino acid sequence to a protein (which is considered a glycosyltransferase) encoded by a gene (gene number: LBA1283) derived from *Lactobacillus acidophilus* NCFM. The protein LCS1128P has 53.1% identity in amino acid sequence to a protein (which is considered a glycosyltransferase) encoded by the ybaI gene derived from *Lactococcus lactis* IL1403 strain.

The protein having the amino acid sequence of SEQ ID NO: 108 (LCS1890P) has 18.3% identity in amino acid sequence (in 295 amino acid residues) to a protein encoded by the epsG gene derived from *Lactobacillus johnsonii* NCC533 strain and involved in exopolysaccharide synthesis. The protein LCS1890P has 18.3% identity in amino acid sequence (in 344 amino acid residues) to a protein encoded by the epsT gene derived from *Lactococcus lactis* subsp. *cremoris* HO2 strain and involved in exopolysaccharide synthesis.

The gene of the present invention is preferably a gene having a polynucleotide selected from among the following polynucleotides (d) to (f):

(d) a polynucleotide having any of the nucleotide sequences of SEQ ID NOs: 1, 3, 5, 7, 9, 11, 13, 15, 81, 83, 85, 87, 89, 91, 93, 95, 97, 99, 101, 103, 105, and 107;

(e) a polynucleotide which hybridizes, under stringent conditions, with a polynucleotide having a nucleotide sequence complementary to any of the nucleotide sequences of (d), and which encodes a protein exhibiting cytokine production regulatory activity; and (f) a polynucleotide which has a nucleotide sequence having 90% or higher identity to any of the nucleotide sequences of (d), and which encodes a protein exhibiting cytokine production regulatory activity.

When the DNA fragment having the nucleotide sequence of SEQ ID NO: 1 (the DNA fragment is named "cps1A gene") is present in *Lactobacillus casei* YIT 9029, the bacterium exhibits the effect of suppressing production of TNF-α, IL-6, IL-10, and IL-12 from macrophages and/or immunocompetent cells.

When the DNA fragment having the nucleotide sequence of SEQ ID NO: 3 (the DNA fragment is named "cps1B gene") is present in *Lactobacillus casei* YIT 9029, the bacterium exhibits the effect of suppressing production of TNF-α, IL-6, IL-10, and IL-12 from macrophages and/or immunocompetent cells.

When the DNA fragment having the nucleotide sequence of SEQ ID NO: 5 (the DNA fragment is named "cps1C gene") is present in *Lactobacillus casei* YIT 9029, the bacterium exhibits the effect of suppressing production of TNF-α, IL-6, IL-10, and IL-12 from macrophages and/or immunocompetent cells.

When the DNA fragment having the nucleotide sequence of SEQ ID NO: 7 (the DNA fragment is named "cps1D gene") is present in *Lactobacillus casei* YIT 9029, the bacterium exhibits the effect of suppressing production of TNF-α, IL-6, IL-10, and IL-12 from macrophages and/or immunocompetent cells.

When the DNA fragment having the nucleotide sequence of SEQ ID NO: 9 (the DNA fragment is named "cps1E gene") is present in *Lactobacillus casei* YIT 9029, the bacterium exhibits the effect of suppressing production of TNF-α, IL-6, and IL-12 from macrophages and/or immunocompetent cells.

When the DNA fragment having the nucleotide sequence of SEQ ID NO: 11 (the DNA fragment is named "cps1F gene") is present in *Lactobacillus casei* YIT 9029, the bacterium exhibits the effect of suppressing production of TNF-α, IL-6, and IL-12 from macrophages and/or immunocompetent cells.

When the DNA fragment having the nucleotide sequence of SEQ ID NO: 13 (the DNA fragment is named "cps1G gene") is present in *Lactobacillus casei* YIT 9029, the bacterium exhibits the effect of suppressing production of TNF-α, IL-6, and IL-12 from macrophages and/or immunocompetent cells.

When the DNA fragment having the nucleotide sequence of SEQ ID NO: 15 (the DNA fragment is named "cps1J gene") is present in *Lactobacillus casei* YIT 9029, the bacterium exhibits the effect of suppressing production of TNF-α, IL-6, IL-10, and IL-12 from macrophages and/or immunocompetent cells.

When the DNA fragment having the nucleotide sequence of SEQ ID NO: 81 (the DNA fragment is named "cps2A gene") is present in *Lactobacillus casei* YIT 9029, the bacterium does not affect production of TNF-α from macrophages and/or immunocompetent cells, but exhibits the effect of suppressing production of IL-10 therefrom.

When the DNA fragment having the nucleotide sequence of SEQ ID NO: 83 (the DNA fragment is named "cps2C gene") is present in *Lactobacillus casei* YIT 9029, the bacterium exhibits the effect of promoting production of TNF-α from macrophages and/or immunocompetent cells, and exhibits the effect of suppressing production of IL-10 therefrom.

When the DNA fragment having the nucleotide sequence of SEQ ID NO: 85 (the DNA fragment is named "cps2D gene") is present in *Lactobacillus casei* YIT 9029, the bacterium exhibits the effect of suppressing production of TNF-α and IL-10 from macrophages and/or immunocompetent cells.

When the DNA fragment having the nucleotide sequence of SEQ ID NO: 87 (the DNA fragment is named "cps2E gene") is present in *Lactobacillus casei* YIT 9029, the bacterium exhibits the effect of promoting production of TNF-α from macrophages and/or immunocompetent cells, and exhibits the effect of suppressing production of IL-10 therefrom.

When the DNA fragment having the nucleotide sequence of SEQ ID NO: 89 (the DNA fragment is named "cps2F gene") is present in *Lactobacillus casei* YIT 9029, the bacterium exhibits the effect of promoting production of TNF-α from macrophages and/or immunocompetent cells, and exhibits the effect of suppressing production of IL-10 therefrom.

When the DNA fragment having the nucleotide sequence of SEQ ID NO: 91 (the DNA fragment is named "cps2G gene") is present in *Lactobacillus casei* YIT 9029, the bacterium exhibits the effect of suppressing production of TNF-α and IL-10 from macrophages and/or immunocompetent cells.

When the DNA fragment having the nucleotide sequence of SEQ ID NO: 93 (the DNA fragment is named "cps2H gene") is present in *Lactobacillus casei* YIT 9029, the bacterium exhibits the effect of suppressing production of TNF-α and IL-10 from macrophages and/or immunocompetent cells.

When the DNA fragment having the nucleotide sequence of SEQ ID NO: 95 (the DNA fragment is named "cps3A gene") is present in *Lactobacillus casei* YIT 9029, the bacterium exhibits the effect of suppressing production of TNF-α and IL-10 from macrophages and/or immunocompetent cells.

When the DNA fragment having the nucleotide sequence of SEQ ID NO: 97 (the DNA fragment is named "cps3B gene") is present in *Lactobacillus casei* YIT 9029, the bacterium exhibits the effect of suppressing production of TNF-α and IL-10 from macrophages and/or immunocompetent cells.

When the DNA fragment having the nucleotide sequence of SEQ ID NO: 99 (the DNA fragment is named "cps3C gene") is present in *Lactobacillus casei* YIT 9029, the bacterium exhibits the effect of suppressing production of TNF-α and IL-10 from macrophages and/or immunocompetent cells.

When the DNA fragment having the nucleotide sequence of SEQ ID NO: 101 (i.e., the gene of gene number: LCS0838) is present in *Lactobacillus casei* YIT 9029, the bacterium exhibits the effect of suppressing production of TNF-α and IL-10 from macrophages and/or immunocompetent cells.

When the DNA fragment having the nucleotide sequence of SEQ ID NO: 103 (i.e., the gene of gene number: LCS1111) is present in *Lactobacillus casei* YIT 9029, the bacterium does not affect production of TNF-α from macrophages and/or immunocompetent cells, but exhibits the effect of suppressing production of IL-10 therefrom.

When the DNA fragment having the nucleotide sequence of SEQ ID NO: 105 (i.e., the gene of gene number: LCS1128) is present in *Lactobacillus casei* YIT 9029, the bacterium does not affect production of TNF-α from macrophages and/or immunocompetent cells, but exhibits the effect of suppressing production of IL-10 therefrom.

When the DNA fragment having the nucleotide sequence of SEQ ID NO: 107 (i.e., the gene of gene number: LCS1890) is present in *Lactobacillus casei* YIT 9029, the bacterium exhibits the effect of suppressing production of TNF-α and IL-10 from macrophages and/or immunocompetent cells.

As used herein, the expression "under stringent conditions" refers to, for example, the case where hybridization is carried out under conditions described in Molecular Cloning—a Laboratory manual 2nd edition (Sambrook, et al., 1989); specifically, the case where hybridization is carried out in a solution containing 6×SSC (composition of 1×SSC: 0.15 M sodium chloride, 0.015 M sodium citrate, pH 7.0), 0.5% SDS, 5×Denhardt's solution, and 100 mg/mL herring sperm DNA together with a polynucleotide having a nucleotide sequence complementary to any of the aforementioned nucleotide sequences at 65° C. for 8 to 16 hours.

The expression "nucleotide sequence having 90% or higher identity to any of the nucleotide sequences of (d)" refers to a nucleotide sequence which, upon appropriate alignment, exhibits 90% or higher identity (more preferably 95% or higher) to any of the nucleotide sequences of SEQ ID NOs: 1, 3, 5, 7, 9, 11, 13, 15, 81, 83, 85, 87, 89, 91, 93, 95, 97, 99, 101, 103, 105, and 107.

The gene of the present invention can be readily obtained through a customary PCR technique by use of a primer set prepared on the basis of any of the nucleotide sequences of SEQ ID NOs: 1, 3, 5, 7, 9, 11, 13, 15, 81, 83, 85, 87, 89, 91, 93, 95, 97, 99, 101, 103, 105, and 107, and using, as a template, DNA of *Lactobacillus casei* YIT 9029.

Specifically, the gene of the present invention can be obtained through, for example, PCR by use of a set of chemically synthesized oligonucleotides A and B (oligonucleotide A has a sequence including the N-terminal start codon of any of the aforementioned genes, and oligonucleotide B has a sequence complementary to a sequence including the stop codon of the gene), and by use, as a template, of DNA of *Lactobacillus casei* YIT 9029. For effective cloning of the thus-obtained gene fragment into, for example, a plasmid vector, a sequence for restriction enzyme cleavage may be added on the 5'-end of the oligonucleotide primer. The primer which may be employed in the present invention is generally, for example, a nucleotide chemically synthesized on the basis of information on the nucleotide sequence of the gene of the present invention, and may be the gene of the present invention which has already been obtained or a fragment thereof. Such a nucleotide has a partial nucleotide sequence corresponding to, for example, SEQ ID NO: 1, and includes, for example, 10 to 50 consecutive nucleotides (preferably 15 to 35 consecutive nucleotides).

When, for example, a DNA fragment having a length of 2,000 base pairs is prepared, PCR is carried out under the following conditions: 94° C. for 2 minutes, (95° C. for 10 seconds, 52° C. for 10 seconds, 72° C. for 2 minutes)×30 cycles, and 72° C. for 7 minutes.

The gene of the present invention may be artificially synthesized by means of a DNA synthesizer on the basis of the corresponding nucleotide sequence.

The gene of the present invention is a gene involved in regulation of production of various cytokines. Therefore, when the gene of the present invention is introduced into a microorganism, or when the gene present in the microorganism is modified, cytokine production can be regulated by the microorganism.

When the genes of the present invention are introduced into a microorganism which does not originally have the genes, the genes may be introduced singly or in combination. Introduction of the gene(s) may be carried out through, for example, the competence method using DNA uptake ability, the protoplast PEG method using a protoplast, or electroporation using high-voltage pulses. Particularly, electroporation is preferably employed. Incorporation of the gene(s) into the chromosome of a microorganism may be carried out through homologous recombination or site-specific incorporation.

Modification of the gene of the present invention may be inhibition, suppression, or promotion of expression of the gene.

For inhibition of expression of the gene of the present invention, the gene may be disrupted or deleted through the insertion-inactivation method in which a DNA fragment entirely different from a target gene is inserted into the gene, or the stepwise double crossover method in which the entirety or a portion of a target gene is deleted by stepwise homologous recombination. Particularly, the stepwise double crossover method is preferably employed.

Specifically, when the entirety or a portion of a target gene is deleted, two regions sandwiching the deletion region are obtained from chromosomal DNA or obtained through by PCR amplification, and the two DNA fragments are cloned into a plasmid vector (e.g., pYSSE3) which can replicate in *Escherichia coli* but cannot in a microorganism of interest, so that the fragments are aligned in the same direction as the original direction. Subsequently, the resultant recombinant plasmid DNA is introduced, through electroporation or a similar technique, into a microorganism in which deletion is caused to occur. Through PCR or a similar technique, there is selected, from the resultant antibiotic-resistant clones, a clone in which the plasmid has been inserted into the chromosome through recombination in a region homologous to the above-cloned region upstream or downstream of the target deletion region. The thus-obtained clone is repeatedly subcultured in a medium containing no antibiotic, to thereby select clones which have lost antibiotic resistance through removal of the plasmid from the chromosome by recombination between flanking homologous regions and through disappearance of the plasmid by bacterial growth. Through PCR or a similar technique, there can be separated, from the thus-obtained clones, a clone in which the target gene region has been deleted.

Suppression of expression of the gene of the present invention may be carried out through the so-called RNA interference method in which a short RNA fragment complementary to the 5'-end region of mRNA of the gene is synthesized, or a method in which the gene is modified by, for example, disrupting or deleting a regulatory gene or a region for controlling expression of the gene of the present invention. Particularly, modification of a region for controlling expression of the gene of the present invention is preferred. Specifically, the level of transcription of the gene of the present invention into mRNA can be increased or decreased by modifying the sequence of a promoter for controlling transcription of the gene.

Promotion of expression of the gene of the present invention may be carried out through, for example, a method in which a recombinant plasmid carrying the gene is introduced into a microorganism of interest; a method in which the gene is incorporated into another site of the chromosome through site-specific recombination, to thereby increase the number of copies of the gene in a microorganism; or a method in which the level of expression of the gene is increased by modifying a region for controlling expression of the gene or by modifying a regulatory gene. Particularly preferred is a method of increasing the number of copies of the gene. Specifically, the number of copies of the gene of interest may be increased in microbial cells through the following procedure: the gene (including the original promoter sequence and ribosome-binding site of the gene) is cloned into a plasmid having a plurality copies per microbial cell, or a recombinant plasmid is prepared by ligating only a polypeptide-encoding region of the gene to the downstream of a promoter and a ribosome-binding site which have been obtained from another gene or chemically synthesized, followed by cloning, and the plasmid is introduced into microbial cells through electroporation or a similar technique.

No particular limitation is imposed on the microorganism in which the gene of the present invention is introduced or modified, and the microorganism may be, for example, a Gram-positive bacterium, a Gram-negative bacterium, or yeast. The microorganism employed is preferably a Gram-positive bacterium, particularly preferably, for example, a bacterium belonging to the genus *Lactobacillus* which has been shown to be biologically safe. Among bacteria belonging to the genus *Lactobacillus*, bacteria of the *Lactobacillus casei* group, such as *Lactobacillus casei, Lactobacillus paracasei, Lactobacillus zeae*, and *Lactobacillus rhamnosus* are preferably employed, and *Lactobacillus casei* is particularly preferably employed. Examples of the microorganism originally having a cytokine production regulatory gene include *Lactobacillus casei* YIT 9018 and *Lactobacillus casei* YIT 9029.

In the case of, for example, *Lactobacillus casei* ATCC 334, when, preferably, a DNA fragment encoding cps1A, cps1B, cps1C, cps1D, cps1E, cps1F, cps1G, or cps1J gene is introduced to the downstream of a promoter in consideration of the operon structure of the gene or the position of the promoter, a modified microorganism in which production of TNF-α, IL-10, and IL-12 from macrophages is effectively suppressed can be obtained (Example 6). Deletion of, for example, cps1A gene in *Lactobacillus casei* YIT 9029 can yield a modified microorganism in which production of TNF-α, IL-12, IL-10, and IL-6 is promoted, and suppression activity of IL-6 production from lipopolysaccharide-stimulated macrophages is lost (Examples 4 and 5). Deletion of, for example, cps2A gene or cps2C gene in *Lactobacillus casei* YIT 9029 can yield a modified microorganism in which the level of production of TNF-α or IL-10 from macrophages is changed (Example 4).

The thus-obtained microorganism in which the gene of the present invention has been introduced or modified can be employed, in consideration of the cytokine production regulatory activity thereof, for producing a food, beverage, or drug exhibiting various pharmacological effects. For example, a food, beverage, or drug containing a microorganism which promotes production of a cytokine promoting Th1-type immune response (e.g., IL-2, IL-12, or IFN-γ) is envisaged to exhibit the effect of, for example, inhibiting type I allergy, atopic dermatitis, or pollinosis, or the effect of inhibiting, for example, bacterial infection, viral infection, or cancer cell growth. In contrast, a food, beverage, or drug containing a microorganism which promotes production of a cytokine promoting Th2-type immune response (e.g., IL-4, IL-5, or IL-10) is envisaged to inhibit, for example, inflammation which causes inflammatory bowel disease or atherosclerosis, or envisaged to be applied for, for example, inhibition of an autoimmune disease such as type I diabetes mellitus, chronic rheumatoid arthritis, systemic lupus erythematosus, polymyositis, Sjogren's syndrome, transplant rejection, connective tissue disease, multiple sclerosis, or autoimmune atrophic gastritis.

TNF-α, which is produced by macrophages (i.e., a type of antigen-presenting cells in the innate immune system), is a cytokine widely involved in biological defense mechanisms via inflammation. Since TNF-α receptors are ubiquitous, and TNF-α can activate a plurality of signaling pathways and can induce or inhibit expression of various genes, TNF-α is envisaged to exhibit a wide variety of physiological effects in, for example, biological defense, biological homeostasis, development, and differentiation.

IL-6, which is produced from macrophages, monocytes, vascular endothelial cells, fibroblasts, and keratinocytes, is envisaged to play an important role in host defense, acute-phase reaction, immunoreaction, and hematopoiesis, including proliferation of B-cells or plasma cells, the effect of promoting production of IgG, IgM, and IgA antibodies, differentiation or activation of T-cells, the effect of acting on hepatocytes to thereby induce an acute-phase protein (e.g., C-reactive protein (CRP) or haptoglobin), and considerable increase of IL-6 in synovial fluid of rheumatoid arthritis patients.

IL-12, which is produced by antigen-presenting cells (macrophages or dendritic cells) or B-cells, is a potent IFN-γ inducer and is not produced from T-cells. IL-12 exhibits a plurality of effects, including the effect of differentiating naive helper T-cells (Th0 cells) into Th1 cells, and the effect of activating NK cells or NKT cells. Therefore, IL-12 is envisaged to act as a physiological bridge between the innate immune system and the adaptive immune system.

When the microorganism of the present invention in which the gene of the present invention has been introduced or modified is incorporated into a food or beverage or in a drug, living cells, heated cells (dead cells), or lyophilized cells of the microorganism may be employed. Alternatively, a cultured product containing the microorganism may be employed. So long as the microorganism retains cytokine production regulatory activity of interest, processed cells of the microorganism may be employed.

When the microorganism of the present invention is employed in a drug, the microorganism may be mixed with a solid or liquid pharmaceutical nontoxic carrier, and the mixture may be administered in the form of a conventional drug product. Examples of such a drug product include solid products such as tablet, granules, powder, and capsule; liquid products such as solution, suspension, and emulsion; and lyophilized products. Such a drug product may be prepared through a customary technique for drug production. Examples of the aforementioned pharmaceutical nontoxic carrier include glucose, lactose, sucrose, starch, mannitol, dextrin, fatty acid glyceride, polyethylene glycol, hydroxyethyl starch, ethylene glycol, polyoxyethylene sorbitan fatty acid ester, amino acid, gelatin, albumin, water, and saline. If necessary, the drug product may appropriately contain a conventional additive such as a stabilizer, a humectant, an emulsifier, a binder, an isotonizing agent, or an excipient.

The microorganism of the present invention in which the gene of the present invention has been introduced or modified may also be incorporated into a food or beverage in addition to the aforementioned drug product. When the microorganism is incorporated into a food or beverage, the microorganism may be employed as is, or mixed with various nutritional ingredients. The resultant food or beverage can be employed, in consideration of the cytokine production regulatory activity of the microorganism, for producing a health food or food material exhibiting various pharmacological effects. Specifically, when the microorganism obtained through the method of the present invention is incorporated into a food or beverage, the microorganism may be appropriately mixed with an additive which can be used in a food or beverage, and the mixture may be prepared, through conventional means, into a form suitable for edible use; for example, granules, particles, tablet, capsule, or paste. The microorganism may be added to a variety of foods; for example, processed meat products (e.g., ham and sausage), processed fish products (e.g., kamaboko and chikuwa), bread, confectionary, butter, and powdered milk. Alternatively, the microorganism may be added to beverages such as water, fruit juice, milk, refreshing beverages, and tea beverages. As used herein, the term "food or beverage" encompasses animal feeds.

Examples of the food or beverage of the present invention include fermented foods and beverages produced by use of the microorganism of the present invention, such as fermented milk, lactic acid bacteria beverages, fermented soybean milk, fermented fruit juice, and fermented plant extract. Such a fermented food or beverage may be produced through a customary method. For example, a fermented milk product may be produced through the following procedure. Firstly, only the microorganism of the present invention is inoculated into a sterilized milk medium, or the microorganism and another microorganism are simultaneously inoculated into the medium, followed by culturing, and the cultured product is homogenized to thereby yield a fermented milk base. Subsequently, a separately prepared syrup is added to and mixed with the fermented milk base, and the mixture is homogenized by means of, for example, a homogenizer, followed by addition of a flavor to the resultant mixture, to thereby yield a final product. The thus-produced fermented milk product may be in any form, such as a plain-type product, a soft-type product, a fruit-flavor-type product, a solid product, or a liquid product.

The gene of the present invention can also be employed for screening a microorganism exhibiting cytokine production regulatory activity.

Specifically, a microorganism exhibiting cytokine production regulatory activity can be selected through screening by determining the presence or absence of the gene of the present invention, and/or determining the level of expression of the gene.

For determination of the presence or absence of the gene and/or the level of expression of the gene, the presence or absence of a target gene in a microorganism, the number of copies of the gene, or the level of expression thereof is determined through southern hybridization, DNA microarray, or RT-PCR by use of a probe or primer which can detect the gene of the present invention or mRNA derived therefrom. A microorganism of interest is selected on the basis of the presence or absence of the target gene or the level of expression of the gene.

Since the gene of the present invention has a function of PS-PG synthesis or glycosyltransferase, the gene can also be employed for the purpose of PS-PG synthesis or screening of microorganisms having PS-PG. Also, the gene of the present invention can be employed for the purpose of determining whether or not a bacterium has a carbohydrate structure required for expression of, for example, an immune function, or the purpose of improving the function of a bacterium through expression of a carbohydrate which is not intrinsic to the bacterium.

The recombinant vector of the present invention containing any of the polynucleotides shown in (d) to (f) or a portion (fragment) thereof can be obtained through a known technique (e.g., in vitro ligation) by use of any vector (e.g., pHY400, pSA3, or pYSSE3) having such a gene marker that can determine introduction of the vector into *Escherichia coli* and a microorganism of interest.

A host microorganism containing the aforementioned recombinant vector can be obtained through a known method. Specifically, when the recombinant vector is introduced into a host microorganism, electroporation or a similar technique may be employed. When the recombinant vector is incorporated into the chromosome of the microorganism, there may be employed a method in which a recombinant vector having a DNA region homologous to that of the microorganism is introduced through electroporation or a similar technique, and then the vector incorporated into the chromosome by homologous recombination is determined through, for example, PCR.

The DNA array or DNA chip of the present invention containing any of the polynucleotides shown in (d) to (f) or a portion (fragment) thereof can be prepared through a known technique such as photolithography. The DNA array or the DNA chip can be employed for screening a microorganism which expresses the gene of the present invention.

In order to effectively perform the aforementioned introduction of the gene of the present invention into a microorganism, modification of the gene, or screening of microorganisms, preferably, there is employed a recombinant vector containing the polynucleotide of the present invention or a portion thereof, a primer for PCR or RT-PCR containing a portion (fragment) of the polynucleotide of the present invention, a primer for PCR or RT-PCR which can amplify the polynucleotide or a portion thereof, or a nucleic acid fragment for hybridization containing the polynucleotide or a portion thereof.

The nucleic acid fragment (e.g., primer) which may be employed in the present invention is generally, for example, a nucleotide chemically synthesized on the basis of information on the nucleotide sequence of the gene of the present invention. Preferably, such a nucleotide has a partial nucleotide sequence corresponding to any of the nucleotide sequences of SEQ ID NOs: 1, 3, 5, 7, 9, 11, 13, 15, 81, 83, 85, 87, 89, 91, 93, 95, 97, 99, 101, 103, 105, and 107, and includes 10 to 50 consecutive nucleotides (preferably 15 to 35 consecutive nucleotides).

The present invention will next be described in more detail by way of examples.

EXAMPLES

Example 1

Gene analysis of *Lactobacillus casei* YIT 9029 (gene extraction)

The genes of *Lactobacillus casei* YIT 9029 involved in PS-PG synthesis and glycosyltransferase were retrieved from the relevant chromosomes based on the homology to known microorganism-derived polysaccharide synthesis genes. Specifically, through the Lipman-Pearson method (Lipman, D. J. and Pearson, W. R., 1985, "Rapid and sensitive protein similarity searches," Science 227: 1435-1441) by use of genetic information processing software (GENETYX, product of Genetyx Corporation), all the open reading frames (ORFS) possibly encoding proteins speculated from the genomic sequence of *Lactobacillus casei* YIT 9029 were subjected to a homology analysis with respect to the amino acid sequences of the proteins which the aforementioned respective genes encode. As a result, several tens of ORFs which were considered to define genes possibly relating to polysaccharide synthesis and glycosyltransfer were extracted. Among them, the genes represented by SEQ ID NOs: 1, 3, 5, 7, 9, 11, 13, 15, 81, 83, 85, 87, 89, 91, 93, 95, 97, 99, 101, 103, 105, and 107 were found to be novel genes through homology search with respect to known genes included in a database.

Example 2

Isolation of gene-disrupted strains of *Lactobacillus casei* YIT 9029 (1)

A mutant strain in which a gene represented by SEQ ID NO: 3 (cps1B) was deleted was produced through the following procedure.

As primers, there were employed an oligonucleotide 5'-cgggatccgagccaaaacatgttgttgct-3' (SEQ ID NO: 17), which had been designed by adding a sequence including a BamH I restriction site to the 5'-end of a sequence selected from the sequence of SEQ ID NO: 3, and an oligonucleotide 5'-aactgcagtgttacgacaacaaccccgt-3' (SEQ ID NO: 18), which had been designed by adding a sequence including a Pst I restriction site to the 5'-end of a sequence selected from the sequence complementary to the sequence of SEQ ID NO: 3. By use of KOD Plus DNA polymerase (product of TOYOBO, product code: KOD-201) and according to an instruction attached to the enzyme, PCR was performed with DNA of *Lactobacillus casei* YIT 9029 as a template. The thus-amplified DNA fragment is a partial sequence of the cps1B gene lacking the amino terminus and the carboxyl terminus. This product was mixed with an equiamount of Tris-EDTA (10 mM Tris(pH 8.0)-1 mM EDTA, hereinafter referred to as TE) saturated phenol-chloroform-isoamyl alcohol (25:24:1). After sufficient shaking, the mixture was centrifuged at 15,000×g for 5 minutes, to thereby separate it into two layers. The upper layer an aqueous layer was recovered, and 3 M sodium carbonate solution (pH 7) (1/10 amount to the aqueous layer) and 99.5% ethanol (thrice amount to the aqueous layer) were added thereto. The resultant mixture was allowed to stand at −20° C. for 30 minutes or longer and then centrifuged at 4° C. and 15,000×g for 15 minutes. The supernatant was removed, and 70% ethanol was added to the precipitate for washing. The obtained mixture was centrifuged at 15,000×g for 5 minutes. After centrifugation, ethanol was removed, and the precipitate was dried under reduced pressure.

The precipitate was digested with restriction enzymes BamH I and Pst I (products of Takara Bio Inc.) at 37° C. for 20 hours in H buffer (product of Takara Bio Inc.) reaction solution (100 µL). Subsequently, the aforementioned TE saturated phenol-chloroform-isoamyl alcohol treatment (mixing with solvent to recovery of aqueous layer) was repeated twice. An aqueous layer was recovered, and 3 M sodium carbonate solution (pH 7) (1/10 amount to the aqueous layer) and 99.5% ethanol (thrice amount to the aqueous layer) were added thereto. The resultant mixture was allowed to stand at −20° C. for 30 minutes or longer and then centrifuged at 4° C. and 15,000×g for 15 minutes. The supernatant was removed, and 70% ethanol was added to the precipitate for washing. The obtained mixture was centrifuged at 15,000×g for 5 minutes. After centrifugation, ethanol was removed, and the precipitate was dried under reduced pressure.

As a plasmid vector, there was employed pYSSE3 (FIG. 1), which has a replication region for *E. coli* originating from plasmid pUC19 and has an erythromycin-resistant gene originating from plasmid pAMβ1 which functions both in *E. coli* and *Lactobacillus*. The pYSSE3 DNA was digested with restriction enzymes BamH I and Pst I (products of Takara Bio Inc.) at 37° C. for 20 hours in H buffer (product of Takara Bio Inc.) reaction solution (100 µL). Subsequently, a 10-fold concentrated CIP buffer (product of TOYOBO) (20 µL) and water were added thereto so as to adjust the total volume to 200 µL, and calf intestine phosphatase (product of TOYOBO) (3 µL) was added thereto, followed by incubation at 37° C. for 2 hours. Thereafter, the aforementioned TE saturated phenol-chloroform-isoamyl alcohol treatment and precipitation with ethanol were performed, and the precipitate was dried under reduced pressure.

The aforementioned DNA fragment consisting of an internal sequence of the cps1B gene and the plasmid vector which had been digested with restriction enzymes were mixed each in an amount of about 0.01 to about 0.1 µg, and an equivolume of Solution I of DNA ligation kit Ver. 2.1 (product of Takara Bio Inc.) was added to the mixture, followed by incubation at 16° C. for 30 minutes. The product was placed on ice.

Next, the above reaction mixture (5 µL) was added to JM109 competent cells (product of TOYOBO) (100 µL), which had been placed on ice after dissolution, and the mixture was incubate for 30 minutes on ice after mild mixing. Thereafter, the reaction mixture was heated at 42° C. for 30 seconds, and returned to ice. To the cell liquid, an SOC medium (product of TOYOBO) (1 mL) was added, and culture was performed at 37° C. for one hour. The culture was spread onto an LB agar medium to which 500 µg/mL erythromycin (erythromycin injection, product of Dainabot) had been added (containing bacto-tryptone (10 g), bact-yeast extract (5 g), sodium chloride (5 g), and agar (15 g) in 1 L), followed by incubation at 37° C.

The formed erythromycin-resistant colonies were grown in an LB medium to which 500 µg/mL erythromycin had been added, and recombinant plasmid DNA was extracted by means of Wizard Plus SV Minipreps DNA Purification System (product of Promega).

DNA transfer to *Lactobacillus casei* YIT 9029 was performed through the following procedure. The relevant microorganism was grown in an MRS medium (product of Difco), and a culture liquid in a logarithmic growth phase was centrifuged at 5,000×g and 4° C. for 5 minutes, whereby the cells were collected. The cells were washed once with ice-cooled 20 mM HEPES (pH 7.0) and once with 10% glycerol, and the washed cells were suspended in 10% glycerol (initial Klett colorimeter value of culture liquid×2 μL). The cell suspension (50 μL) and the recombinant plasmid DNA solution (3 μL) were mixed together, and the mixture was placed in a 2 mm-width cuvette for electroporation. Electroporation was performed by means of Gene Pulser II (product of Bio-Rad Laboratories, Inc.) at 1.5 kV, 200Ω, and 25 μF. An MRS medium (1 mL) was added to the liquid after electroporation, and the mixture was cultured at 37° C. for 2 hours. Subsequently, the culture liquid was spread onto an MRS agar medium to which 20 μg/mL erythromycin had been added, followed by incubation at 37° C. for 2 or 3 days.

A part of the thus-grown erythromycin-resistant colonies was removed and suspended in TE (50 μL). The suspension was treated at 94° C. for 2.5 minutes. A portion of the suspension was employed as a template of PCR. PCR analysis employed the following two primers: a primer selected from sequences which are included in a cps1B gene present in a *Lactobacillus casei* YIT 9029 chromosome and which are not included in a sequence of the cps1B gene cloned to the plasmid; and a primer selected from sequences which are included in the plasmid vector and in the vicinity of a cloned cps1B gene internal fragment. The analysis revealed that the transferred plasmid was incorporated into a region homologous to a cps1B gene fragment included in the recombinant plasmid in the *Lactobacillus casei* YIT 9029 chromosomal cps1B gene, whereby the cps1B gene was cleaved (disrupted). The thus-obtained clone was employed as Ωcps1B.

Through a method similar to the above method employed for isolating the Ωcps1B, gene-disrupted strains for each of the genes cps1A, cps1D, cps1E, cps1F, cps1G, and cps1J were isolated and are represented by Ωcps1A, Ωcps1D, Ωcps1E, Ωcps1F, Ωcps1G, and Ωcps1J, respectively. Furthermore, in order to confirm the effect of the introduction of plasmid vector pYSSE3, another disrupted strain was isolated and is represented by YIT 9029/pYSSE3. In the disrupted strain, a part (abbreviated as #231) of a region in the genomic sequence of *Lactobacillus casei* YIT 9029, which region is considered to contain no effective gene, was similarly disrupted. Table 1 shows the PCR primer sequences for amplifying an internal sequence of each gene employed.

TABLE 1

| | Restriction site | Primer sequence | SEQ ID NO | Restriction site | Primer sequence | SEQ ID NO |
|---|---|---|---|---|---|---|
| cps1A | BamHI | 5'-cgggatccgacacttcgctgttggtcaa-3' | 19 | PstI | 5'-aactgcagggtttggtctgtaagctctc-3' | 20 |
| cps1B | BamHI | 5'-cgggatccgagccaaaacatgttgttgct-3' | 17 | PstI | 5'-aactgcagtgttacgacaacaaccccgt-3' | 18 |
| cps1D | PstI | 5'-aactgcaggctaaaattgtttggcatgttc-3' | 21 | BamHI | 5'-cgggatcccacaatcatctcactagctcc-3' | 22 |
| cps1E | BamHI | 5'-cgggatccgtggcatacttctttccattt-3' | 23 | PstI | 5'-aactgcaggagagctccaaagattgcaa-3' | 24 |
| cps1F | BamHI | 5'-cgggatccgtggcatacttctttccattt-3' | 25 | PstI | 5'-aactgcaggagagctccaaagattgcaa-3' | 26 |
| cps1G | BamHI | 5'-cgggatccatcatgaatcggcagtattta-3' | 27 | PstI | 5'-aactgcagaccgtctaaaatagtaacattt-3' | 28 |
| cps1J | BamHI | 5'-cgggatccgccgagctacatattctcga-3' | 29 | PstI | 5'-aactgcagtccaacgcaaccatctcaga-3' | 30 |
| #231 | BamHI | 5'-cgggatcctgggctcagtggttgctt-3' | 31 | PstI | 5'-aactgcagggtttgaatggccatcatc-3' | 32 |

Through a method similar to the method employed for isolating the Ωcps1B, gene-disrupted strains for each of the genes cps2A, cps2C, cps2D, cps2E, cps2F, cps2G, cps2H, cps3A, cps3B, cps3C, LCS0838, LCS1111, LCS1128, and LCS1890 had deletion were isolated and are represented by Ωcps2A, Ωcps2C, Ωcps2D, Ωcps2E, Ωcps2F, Ωcps2G, Ωcps2H, Ωcps3A, Ωcps3B, Ωcps3C, ΩLCS0838, ΩLCS1111, ΩLCS1128, and ΩLCS1890, respectively. Table 2 shows the PCR primer sequences for amplifying an internal sequence of each gene employed.

TABLE 2

| | Restriction site | Primer sequence | SEQ ID NO | Restriction site | Primer sequence | SEQ ID NO |
|---|---|---|---|---|---|---|
| cps2A | BamHI | 5'-gcggatccgcagttgggccactttc-3' | 53 | PstI | 5'-ttctgcagttagatgggactgttcaggaa-3' | 54 |
| cps2C | BamHI | 5'-gcggatccgacgaggtgattgtgg-3' | 55 | PstI | 5'-ttctgcagttagcggtaatacatcaattt-3' | 56 |

TABLE 2-continued

| | Restriction site | Primer sequence | SEQ ID NO | Restriction site | Primer sequence | SEQ ID NO |
|---|---|---|---|---|---|---|
| cps2D | BamHI | 5'-gcggatccgaacttgctgtcaataagc-3' | 57 | PstI | 5'-tctgcagttagattggccaagccattg-3' | 58 |
| cps2E | BamHI | 5'-gcggatccgcggggtatacatttc-3' | 59 | PstI | 5'-ttctgcagttataagccttttacccc-3' | 60 |
| cps2F | KpnI | 5'-ccggtaccgttagtactgtggttaacgg-3' | 61 | EcoRI | 5'-gcgaattcttacttgatagcagccttatc-3' | 62 |
| cps2G | KpnI | 5'-ccggtaccgtactaggaccgacaggcg-3' | 63 | EcoRI | 5'-gcgaattcttaaccaatcaaaacttcaacaac-3' | 64 |
| cps2H | PstI | 5'-cgctgcagtcgccaaatgaatcattgg-3' | 65 | BamHI | 5'-gcggatccttaataccccaacatagc-3' | 66 |
| cps3A | BamHI | 5'-cgggatccgatcggcgaattgcggtt-3' | 67 | PstI | 5'-aactgcagcacgacctgatgcaccat-3' | 68 |
| cps3B | BamHI | 5'-cgggatccggtcgcaagattggctttg-3' | 69 | PstI | 5'-aactgcagccgcaatcgagactgoat-3' | 70 |
| cps3C | BamHI | 5'-cgggatcctggctgctggtggctttt-3' | 71 | PstI | 5'-aactgcagocataacagcatccctaga-3' | 72 |
| LCS0838 | Hind III | 5'-aataagcttttagcagcgggtgac-3' | 73 | NheI | 5'-attgctagcatcaggagactcgagac-3' | 74 |
| LCS1111 | BamHI | 5'-cgggatccgcggcttatatgcgagaaa-3' | 75 | PstI | 5'-aactgcagtaacacaaatagactcaggg-3' | 76 |
| LCS1128 | PstI | 5'-ttactgcagcaaatcaaacagttaca-3' | 77 | XbaI | 5'-taatctagaccattgacggccagc-3' | 78 |
| LCS1890 | EcoRI | 5'-cgcgaattcctgattcaaacaactccatgg-3' | 79 | BamHI | 5'-cgggatccttactgatcaaagttgttaatgcc-3' | 80 |

Example 3

Isolation of Gene-Disrupted Strains of *Lactobacillus casei* YIT 9029 (2)

A mutant strain in which a gene represented by SEQ ID NO: 1 (cps1A) was deleted was produced through the following procedure. There was employed a set of an oligonucleotide 5'-atactgcagattggcatgggttttc-3' (SEQ ID NO: 33), which had been designed by adding a sequence including a Pst I restriction site to the 5'-end of a sequence selected from a region in the vicinity of about 1 kbp upstream of the cps1A gene, and an oligonucleotide 5'-taagaattcagcttcgtattttggtaca-3' (SEQ ID NO: 34), which had been designed by adding a sequence including an EcoR I restriction site to the 5'-end of a sequence complementary to a sequence selected from a region in the vicinity of the 5'-end of the cps1A gene. There was also employed another set of an oligonucleotide 5'-gaagaattcaatatgcaggattta-3' (SEQ ID NO: 35), which had been designed by adding an EcoR I restriction site to the 5'-end of a sequence selected from a region in the vicinity of the 3'-end of the cps1A gene, and an oligonucleotide 5'-atatctagattcccccaaccatact-3' (SEQ ID NO: 36), which had been designed by adding an Xba I site to the 5'-end of a sequence complementary to a sequence selected from a region in the vicinity of about 1 kbp downstream side of the cps1A gene. By use of KOD Plus DNA polymerase (product of TOYOBO, product code: KOD-201) and according to an instruction attached to the enzyme, PCR was performed using each set of primers with DNA of *Lactobacillus casei* YIT 9029 as a template. In a manner similar to that of Example 2, each PCR product was subjected to the TE saturated phenol-chloroform-isoamyl alcohol treatment and precipitation with ethanol, and the precipitate was dried under reduced pressure.

The precipitate of the former case was digested with restriction enzymes Pst I and EcoR I (products of Takara Bio Inc.) at 37° C. for 20 hours in H buffer (product of Takara Bio Inc.) reaction mixture (100 μL). The precipitate of the latter case was digested with restriction enzymes EcoR I and Xba I (products of Takara Bio Inc.) at 37° C. for 20 hours in M buffer (product of Takara Bio Inc.) reaction mixture (100 μL). In a manner similar to that of Example 2, the precipitate was dried under reduced pressure. In a manner similar to that of Example 2, a plasmid vector pYSSE3 digested with restriction enzymes Pst I and Xba I was prepared.

In ligation, the aforementioned two DNA fragments and the plasmid vector digested with restriction enzymes Pst I and Xba I were mixed each in an amount of 0.01 to 0.1 and an equivolume of Solution I of DNA ligation kit Ver. 2.1 (product of Takara Bio Inc.) was added to the mixture, followed by incubation at 16° C. for 30 minutes. The product was placed on ice.

In a manner similar to that of Example 2, recombinant plasmid DNA including a target fragment was isolated from erythromycin-resistant colonies.

In the thus-formed plasmid, the two DNA fragments were inserted and juxtaposed between the Pst I restriction site and the Xba I restriction site of the vector, and sandwiched the EcoR I restriction site.

DNA transfer to *Lactobacillus casei* YIT 9029 and isolation of a clone endowed with erythromycin resistance were performed in a manner similar to that of Example 2.

A part of the thus-grown erythromycin-resistant colonies was removed and suspended in TE (50 µL). The suspension was treated at 94° C. for 2.5 minutes. A portion of the suspension was employed as a template of PCR. PCR analysis employed the following two primers: a primer having a sequence selected from a region which is present just outside the two cloned nucleotide sequences and in a *Lactobacillus casei* YIT 9029 chromosome, and a primer having a sequence selected from the plasmid vector region. The analysis revealed that, through first-stage homologous recombination, the transferred plasmid was incorporated into a region homologous to the fragment of the recombinant plasmid and in the upstream or downstream region of the *Lactobacillus casei* YIT 9029 chromosomal cps1A gene.

The thus-obtained clone was inoculated in MRS medium containing no erythromycin and cultured overnight at 37° C. A portion (0.1%) of the proliferated cells was subcultured in a fresh MRS medium and cultured overnight at 37° C. The subculture and culture were repeatedly performed five times in total. The thus-obtained culture liquid was appropriately diluted and spread onto an MRS agar medium such that about 100 to about 300 colonies could grow, and cultured at 37° C. for two days. Through the replica method, the grown colonies were transferred to an MRS agar medium containing 20 µg/mL erythromycin and to a generally employed MRS agar medium, followed by culturing at 37° C. for one day. The colonies which were not grown in the erythromycin-containing agar medium and which were grown only in the general agar medium were selected.

A part of the thus-selected erythromycin-resistant colonies was removed and suspended in TE (50 µL). The suspension was treated at 94° C. for 2.5 minutes and PCR was performed with a portion of the suspension as a template. Then, a clone which showed the following results was selected: when the PCR was performed by use of a primer having sequences within the two regions which were cloned to the plasmid and a primer having a sequence selected from a region present between the two regions, no DNA fragment was amplified; and when the PCR was performed by use of two primers each having the sequences selected from the two regions, a DNA fragment shorter than the DNA fragment having a length estimated from the original sequence of *Lactobacillus casei* YIT 9029, in which the difference in length corresponded to the length of the deleted region, was amplified. In the selected clone, through the above PCR, it was confirmed that the plasmid inserted in the chromosome had been removed from the chromosome through second-stage homologous recombination between the homologous sequences which differ from those employed in insertion. In this clone, the sequence attributed to the plasmid was removed, and a center portion of the cps1A gene was deleted. The thus-obtained clone is represented by Δcps1A.

In a manner as employed above, gene-disrupted strains in which any one of the genes cps1C, cps1E, and cps1J had been deleted were isolated and are represented by Δcps1C, Δcps1E, and Δcps1J, respectively. Table 3 shows the primer sequences employed in PCR. Furthermore, when a similar procedure including amplifying the optimum regions on the upstream and downstream of each gene, cloning to the plasmid vector, transferring the recombinant plasmid to *Lactobacillus casei* YIT 9029, and deleting a part of the gene through stepwise double crossover is performed, mutant strains in which other gene (cps1B, cps1D, cps1F, or cps1G) had been deleted can be isolated. However, in order to cause deletion in the cps1C gene, a shuttle vector plasmid which can be replicated in *E. coli* or lactic acid bacteria, pH4611 (Mayumi Kiwaki et al., Bioscience Microflora Vol. 20(4), 121-129, 2002) was employed as a plasmid vector. Although pH4611 can be replicated in lactic acid bacteria, removal of plasmid occurs in most cases when culturing is performed in an erythromycin-free medium. After repeated subculture, erythromycin-resistant clones decrease considerably. Thus, an erythromycin-resistant clone can be found to be a clone in which the plasmid has been incorporated into a chromosome. Through further subculturing of the clone, the plasmid can be removed from a chromosome via homologous recombination, and a plasmid-removed clone can be readily selected. The essential operation for the selection is the same as in the case where a non-replicated vector such as pYSSE3 is employed.

TABLE 3

| | Restriction site | Primer sequence | SEQ ID NO | Restriction site | Primer sequence | SEQ ID NO |
|---|---|---|---|---|---|---|
| cps1A upstream | PstI | 5'-atactgcagattggcatgggtttc-3' | 33 | EcoRI | 5'-taagaattcagcttcgtattttggtaca-3' | 34 |
| cps1A downstream | EcoRI | 5'-gaagaattcaatatgcaggattta-3' | 35 | XbaI | 5'-atatctagattcccccaaccatact-3' | 36 |
| cps1C upstream | BamHI | 5'-cgggatcctagggggaatctatcgtgac-3' | 37 | KpnI | 5'-gcggtacctccaaaaccaaaaggatttgg-3' | 38 |
| cps1C downstream | KpnI | 5'-gcggtaccctgacctgaactaatctgct-3' | 39 | PstI | 5'-ttctgcaggagaatcttatattttccatcg-3' | 40 |
| cps1E upstream | XbaI | 5'-acatctagacttgttcacgtcaatacga-3' | 41 | ClaI | 5'-ctcatcgattatgggcgggaataataat-3' | 42 |
| cps1E downstream | ClaI | 5'-tagatcgatacggtatacgat-3' | 43 | PstI | 5'-tatctgcaggccaacaaaagaaagtcg-3' | 44 |
| cps1J upstream | PstI | 5'-agactgcagacgattatctgttgtt-3' | 45 | EcoRI | 5'-atagaattcacccctccaatacattg-3' | 46 |
| cps1J downstream | EcoRI | 5'-taagaattctgagatggttgcgttgg-3' | 47 | XbaI | 5'-taatctagataggctttattcacatcg-3' | 48 |

Example 4

Modification of Cytokine Production Regulatory Activity of a Microorganism by a Cytokine Production Regulating Gene YIT 9029/pYSSE3 was employed as a control strain with respect to 7 insertion inactivation mutant strains (Ωcps1A, Ωcps1B, Ωcps1D, Ωcps1E, Ωcps1F, Ωcps1G, and Ωcps1J in Example 2) of gene-disrupted mutant strains derived from *Lactobacillus casei* YIT 9029. YIT 9029 was employed as a control strain with respect to 4 complete deletion mutant strains (Example 3). These 13 strains were cultured overnight in an MRS medium (product of Difco) at 37° C. Cultured cells were collected through washing with distilled water and treated at 100° C. for 30 minutes, to thereby prepare heat-killed cells, followed by lyophilization. The lyophilized cells were suspended in PBS to a final concentration of 1 mg/mL, and the suspension was autoclaved at 121° C. for 20 minutes. Before use, the product was diluted with a 10% fetal bovine serum-added RPMI-1640 medium (product of SIGMA) (hereinafter referred to as culture liquid).

Macrophages and/or immunocompetent cells were obtained from the spleens removed from four 8- to 15-week-old female BALB/c mice (Japan SLC). Specifically, lipofiber and the like were removed from the spleens of BALB/c mice, and the spleens were broken by means of a piston of an injector in Hanks' buffer (HBSS) containing 10 mM HEPES. All cells were recovered in HBSS (30 mL). The cell suspension was filtered through a 70 μm filter and washed with centrifugation (1,500 rpm, 5 minutes, 4° C.). The supernatant was removed, and the cells were sufficiently dispersed by means of a vortex or the like. Erythrocyte hemolysate (8 mL, 2 mL/spleen) was added to the cells, and the mixture was allowed to react at room temperature for 5 minutes. Immediately after reaction, HBSS was added to the reaction mixture to adjust the total volume to 30 mL, and the resultant mixture was washed with centrifugation. In a similar manner, the supernatant was removed, and the cells were sufficiently dispersed by means of a vortex or the like. Another volume (30 mL) of HBSS was added to the cells, and the cells were washed with centrifugation. The supernatant was removed, and the pellets were dispersed in culture liquid (20 mL). After cell counting, the count of the BALB/c mouse spleen cells was adjusted to $5 \times 10^6$/mL by use of the culture liquid. The cell liquid was dispensed to a 96-well cell culture plate (100 μL/well, $5 \times 10^5$ cells/well/200 μL).

Subsequently, the aforementioned heat-killed lactic acid bacterium cells diluted with the culture liquid were dispensed to the plate (100 μL/well) such that the final concentration was adjusted to 3 or 30 μg/mL (n=3/group).

Immediately after addition of the cells, the plate was transferred to an incubator (37° C., 5% $CO_2$), where culturing was performed for 24 hours. After completion of culture, the supernatant was recovered, and the TNF-α, IL-12p70, IL-10, and IL-6 levels of the supernatant were determined through ELISA (average and standard deviation).

The results are as follows (FIGS. 2 to 5).

(1) As compared with *Lactobacillus casei* YIT 9029/pYSSE3, Ωcps1A promoted production of TNF-α, IL-12p70, IL-10, and IL-6 in BALB/c mouse spleen cells. Similarly, as compared with *Lactobacillus casei* YIT 9029, Δcps1A promoted production of TNF-α, IL-12p70, IL-10, and IL-6 in BALB/c mouse spleen cells. Therefore, the cps1A gene was found to suppress production of TNF-α, IL-12p70, IL-10, and IL-6.

(2) As compared with *Lactobacillus casei* YIT 9029/pYSSE3, Ωcps1B promoted production of TNF-α, IL-12p70, IL-10, and IL-6 in BALB/c mouse spleen cells. Therefore, the cps1B gene was found to suppress production of TNF-α, IL-12p70, IL-10, and IL-6.

(3) As compared with *Lactobacillus casei* YIT 9029, Δcps1C promoted production of TNF-α, IL-12p70, IL-10, and IL-6 in BALB/c mouse spleen cells. Therefore, the cps1C gene was found to suppress production of TNF-α, IL-12p70, IL-10, and IL-6.

(4) As compared with *Lactobacillus casei* YIT 9029/pYSSE3, Ωcps1D promoted production of TNF-α, IL-12p70, IL-10, and IL-6 in BALB/c mouse spleen cells. Therefore, the cps1D gene was found to suppress production of TNF-α, IL-12p70, IL-10, and IL-6.

(5) As compared with *Lactobacillus casei* YIT 9029/pYSSE3, Ωcps1E promoted production of TNF-α, IL-12p70, IL-10, and IL-6 in BALB/c mouse spleen cells. Similarly, as compared with *Lactobacillus casei* YIT 9029, ΔcpsE promoted production of TNF-α, IL-12p70, and IL-6 in BALB/c mouse spleen cells. Therefore, the cps1E gene was found to suppress production of TNF-α, IL-12p70, and IL-6.

(6) As compared with *Lactobacillus casei* YIT 9029/pYSSE3, Ωcps1F promoted production of TNF-α, IL-12p70, and IL-6 in BALB/c mouse spleen cells. Therefore, the cps1F gene was found to suppress production of TNF-α, IL-12p70, and IL-6.

(7) As compared with *Lactobacillus casei* YIT 9029/pYSSE3, Ωcps1G promoted production of TNF-α, IL-12p70, and IL-6 in BALB/c mouse spleen cells. Therefore, the cps1G gene was found to suppress production of TNF-α, IL-12p70, and IL-6.

(8) As compared with *Lactobacillus casei* YIT 9029/pYSSE3, Ωcps1J promoted production of TNF-α, IL-12p70, IL-10, and IL-6 in BALE/c mouse spleen cells. Similarly, as compared with *Lactobacillus casei* YIT 9029, Δcps1J promoted production of TNF-α, IL-12p70, IL-10, and IL-6 in BALB/c mouse spleen cells. Therefore, the cps1J gene was found to suppress production of TNF-α, IL-12p70, IL-10, and IL-6.

Modification of Cytokine Production Regulatory Activity of a Microorganism by a Cytokine Production Regulating Gene (2):

YIT 9029/pYSSE3 was employed as a control strain with respect to 14 insertion inactivation mutant strains (Ωcps2A, Ωcps2C, Ωcps2D, Ωcps2E, Ωcps2F, Ωcps2G, Ωcps2H, Ω3A, Ωcps3B, Ωcps3C, ΩLCS0838, ΩLCS1111, ΩLCS1128, and ΩLCS1890 in Example 2) of gene-disrupted mutant strains derived from *Lactobacillus casei* YIT 9029. These 14 strains were cultured overnight in an MRS medium (product of Difco) at 37° C. Cultured cells were collected through washing with distilled water and treated at 100° C. for 30 minutes, to thereby prepare heat-killed cells, followed by lyophilization. The lyophilized cells were suspended in PBS to a final concentration of 1 mg/mL, and the suspension was autoclaved at 121° C. for 20 minutes. Before use, the product was diluted with a 10% fetal bovine serum-added RPMI-1640 medium (product of SIGMA) (hereinafter referred to as culture liquid). Subsequently, the aforementioned heat-killed lactic acid bacterium cells diluted with the culture liquid were dispensed to the plate (100 μL/well) such that the final concentration was adjusted to 25 μg/mL (n=3/group).

Before use, mouse macrophage RAW264.7 cells (purchased from ATCC) were cultured through a routine method in an incubator (37° C., 5% $CO_2$). The cells were collected through centrifugation (1,500 rpm, 5 minutes, 4° C.) and suspended in the culture liquid ($10^6$/mL). The cell liquid was dispensed to a 96-well cell culture plate (100 µL/well).

Immediately after addition of the mouse macrophage RAW264.7 cells, the plate was transferred to an incubator (37° C., 5% $CO_2$), where culturing was performed for 24 hours. After completion of culture, the supernatant was recovered, and the TNF-α and IL-10 levels of the supernatant were determined through ELISA (average and standard deviation).

Figure 6:
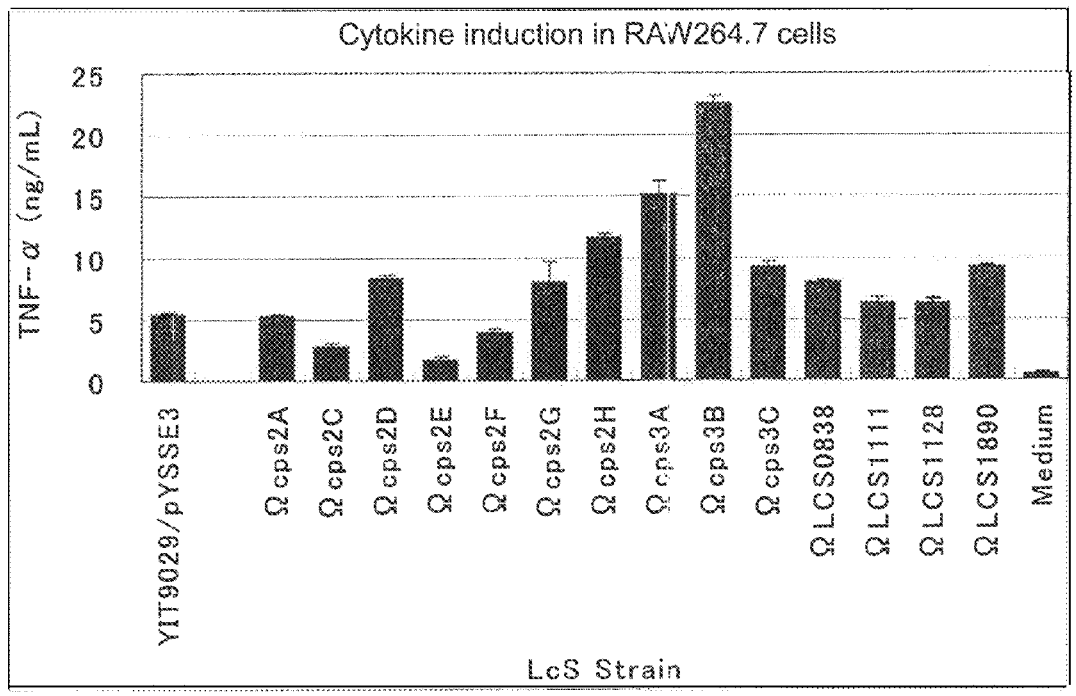
FIG. 6 shows TNF-α inducibility in murine macrophage RAW264.7 cells (amount of bacterial cells added: 25 μg/mL).
Figure 7:
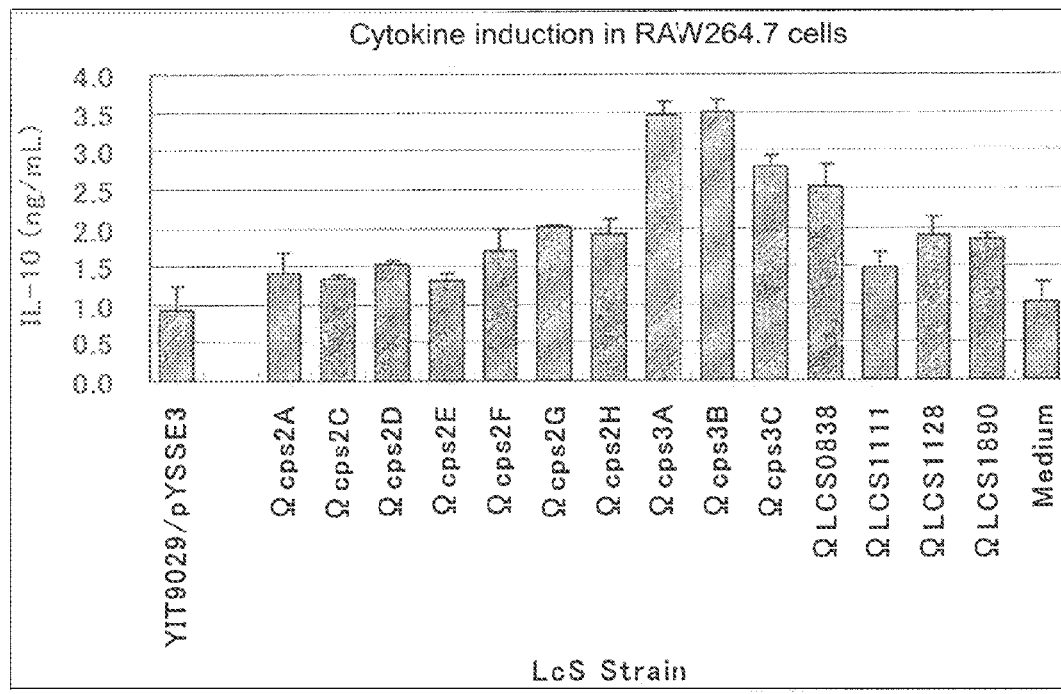
FIG. 7 shows IL-10 inducibility in murine macrophage RAW264.7 cells (amount of bacterial cells added: 25 μg/mL).

The results are as follows (FIGS. 6 and 7).

(1) As compared with *Lactobacillus casei* YIT 9029/ pYSSE3, Ωcps2A did not change the TNF-α level in mouse macrophage RAW264.7 cells, but promoted production of IL-10. Therefore, the cps2A gene was found not to change the TNF-α level and to suppress production of IL-10.

(2) As compared with *Lactobacillus casei* YIT 9029/ pYSSE3, Ωcps2C suppressed production of TNF-α and promoted production of IL-10 in mouse macrophage RAW264.7 cells. Therefore, the cps2C gene was found to promote production of TNF-α and to suppress production of IL-10.

(3) As compared with *Lactobacillus casei* YIT 9029/ pYSSE3, Ωcps2D promoted production of TNF-α and IL-10 in mouse macrophage RAW264.7 cells. Therefore, the cps2D gene was found to suppress production of TNF-α and IL-10.

(4) As compared with *Lactobacillus casei* YIT 9029/ pYSSE3, Ωcps2E suppressed production of TNF-α and promoted production of IL-10 in mouse macrophage RAW264.7 cells. Therefore, the cps2E gene was found to promote production of TNF-α and to suppress production of IL-10.

(5) As compared with *Lactobacillus casei* YIT 9029/ pYSSE3, Ωcps2F suppressed production of TNF-α and promoted production of IL-10 in mouse macrophage RAW264.7 cells. Therefore, the cps2F gene was found to promote production of TNF-α and to suppress production of IL-10.

(6) As compared with *Lactobacillus casei* YIT 9029/ pYSSE3, Ωcps2G promoted production of TNF-α and IL-10 in mouse macrophage RAW264.7 cells. Therefore, the cps2G gene was found to suppress production of TNF-α and IL-10.

(7) As compared with *Lactobacillus casei* YIT 9029/ pYSSE3, Ωcps2H promoted production of TNF-α and IL-10 in mouse macrophage RAW264.7 cells. Therefore, the cps2H gene was found to suppress production of TNF-α and IL-10.

(8) As compared with *Lactobacillus casei* YIT 9029/ pYSSE3, Ωcps3A promoted production of TNF-α and IL-10 in mouse macrophage RAW264.7 cells. Therefore, the cps3A gene was found to suppress production of TNF-α and IL-10.

(9) As compared with *Lactobacillus casei* YIT 9029/ pYSSE3, Ωcps3B promoted production of TNF-α and IL-10 in mouse macrophage RAW264.7 cells. Therefore, the cps3B gene was found to suppress production of TNF-α and IL-10.

(10) As compared with *Lactobacillus casei* YIT 9029/ pYSSE3, Ωcps3C promoted production of TNF-α and IL-10 in mouse macrophage RAW264.7 cells. Therefore, the cps3C gene was found to suppress production of TNF-α and IL-10.

(11) As compared with *Lactobacillus casei* YIT 9029/ pYSSE3, ΩLCS0838 promoted production of TNF-α and IL-10 in mouse macrophage RAW264.7 cells. Therefore, the LCS0838 gene was found to suppress production of TNF-α and IL-10.

(12) As compared with *Lactobacillus casei* YIT 9029/ pYSSE3, ΩLCS1111 did not change the TNF-α level in mouse macrophage RAW264.7 cells, but promoted production of IL-10. Therefore, the LCS1111 gene was found not to change the TNF-α level and to suppress production of IL-10.

(13) As compared with *Lactobacillus casei* YIT 9029/ pYSSE3, ΩLCS1128 did not change the TNF-α level in mouse macrophage RAW264.7 cells, but promoted production of IL-10. Therefore, the LCS1128 gene was found not to change the TNF-α level and to suppress production of IL-10.

(14) As compared with *Lactobacillus casei* YIT 9029/ pYSSE3, ΩLCS1890 promoted production of TNF-α and IL-10 in mouse macrophage RAW264.7 cells. Therefore, the LCS1890 gene was found to suppress production of TNF-α and IL-10.

Example 5

Figure 8:
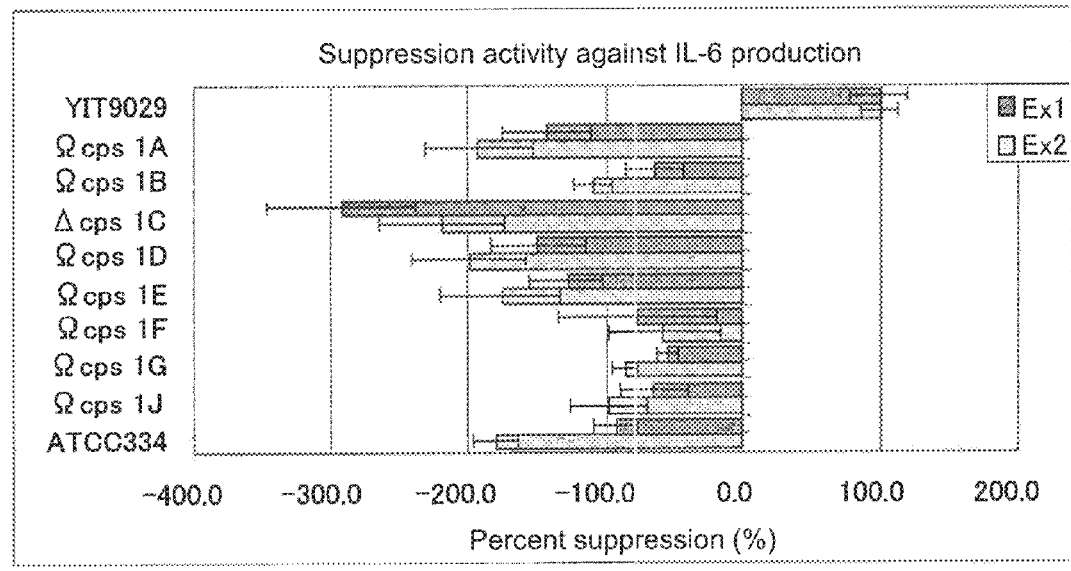
FIG. 8 shows suppression activity against IL-6 production induction in LPS-stimulated murine macrophage RAW264.7 cells (amount of bacterial cells added: 5 μg/mL).

Modification of IL-6 Production Activity of Cytokine Production Regulatory Gene-Disrupted Strains in RAW264.7 Cells Stimulated with LPS Before use, mouse macrophage RAW264.7 cells (purchased from ATCC) were cultured through a routine method in an incubator (37° C., 5% $CO_2$). The cells were collected through centrifugation (1,500 rpm, 5 minutes, 4° C.) and suspended in the culture liquid ($10^6$/mL) as described in Example 4. The cell liquid was dispensed to a 96-well cell culture plate (100 µL/well). Subsequently, *E. coli*-derived lipopolysaccharide (LPS; 10 µg/mL), or a combination of LPS and heat-killed *Lactobacillus casei* ATCC 334 (standard strain), *Lactobacillus casei* YIT 9029, or a heat-killed gene-disrupted strain derived from *Lactobacillus casei* YIT 9029 (Ωcps1A, Ωcps1B, Δcps1C, Ωcps1D, Ωcps1E, Ωcps1F, Ωcps1G, or Ωcps1J) (5 µg/mL) prepared through a method similar to that of Example 4 were added to the plate. The plate was subjected to culturing in an incubator (37° C., 5% $CO_2$) for 24 hours. After completion of culture, the supernatant was recovered, and the IL-6 level of the supernatant was determined through ELISA. The amount of IL-6 production when LPS was singly added was employed as a reference value, and the percent suppression of IL-6 production (%) after addition of each strain was calculated. With a percent suppression of IL-6 production (%) provided by *Lactobacillus casei* YIT 9029 being 100%, the IL-6 production suppression effects of other strains were evaluated as percentage values (%) (FIG. 8).

When heat-killed *Lactobacillus casei* YIT 9029 cells and LPS were added in combination, production of IL-6 was considerably suppressed, as compared with the case of stimulation singly by LPS. In contrast, when the aforementioned gene-disrupted strains or *Lactobacillus casei* ATCC 334 (not containing the gene of the present invention) and LPS were added, production of IL-6 was promoted. Therefore, the genes cps1A, cps1B, cps1C, cps1D, cps1E, cps1F, cps1G, and cps1J were found to suppress production of IL-6 in LPS-stimulated macrophages.

Example 6

Modification of Cytokine Regulatory Activity of a Mutant Strain of *Lactobacillus casei* ATCC 334 to Which the Gene of the Present Invention has been Transferred In order to obtain a region including eight genes: cps1A (SEQ ID NO: 1), cps1B (SEQ ID NO: 3), cps1C (SEQ ID NO: 5), cps1D (SEQ ID NO: 7), cps1E (SEQ ID NO: 9), cps1F (SEQ ID NO: 11), cps1G (SEQ ID NO: 13), and cps1J (SEQ ID NO: 15), PCR was performed with a primer set containing an oligonucleotide 5'-taacccgggtggacttgattacacaagc-3' (SEQ ID NO: 49), having a sequence of a region containing a ribosome-binding site sequence upstream of the cps1A gene and a sequence containing an SmaI restriction site on the 5'-end; and an oligonucleotide 5'-taactgcagacactctttttacact-gcg-3' (SEQ ID NO: 50), having a sequence complementary to a region downstream of the cps1J gene and a sequence containing a Pst I restriction site on the 5'-end. By use of KOD Plus DNA polymerase and according to an instruction attached to the enzyme, PCR was performed with DNA of *Lactobacillus casei* YIT 9029 as a template, whereby a DNA fragment including the genes cps1A, cps1B, cps1C, cps1D, cps1E, cps1F, cps1G, and cps1J was amplified. The thus-amplified DNA fragment was treated (including purification, concentration, digestion with restriction enzymes, etc.) in a manner similar to that of Example 2. Separately, a plasmid vector pYAP300 (i.e., a plasmid which can carry the attP site of phage FSW and an int gene and which can site-specifically insert them into the attB site of *Lactobacillus casei*, FIG. 1) was also subjected to digestion with restriction enzymes, calf intestine phosphatase treatment, purification, and concentration, in a manner similar to that of Example 2. The DNA fragment was ligated to the plasmid vector, so that the genes cps1A through cps1J were inserted to a region downstream of the transcription promoter of the vector, and the product was transferred to *E. coli* JM109 competent cells. The cells were spread onto an LB agar medium containing 500 µg/mL erythromycin, followed by culturing at 37° C. for 2 days. Plasmids were extracted from the obtained colonies, and a recombinant plasmid of interest was selected based on the lengths of the plasmid and restriction-enzyme-digested fragments.

Subsequently, *Lactobacillus casei* ATCC 334 was grown in an MRS medium, and a culture liquid in a logarithmic growth phase was centrifuged at 5,000×g and 4° C. for 5 minutes, whereby the cells were collected. The cells were subjected to electroporation in accordance with the method of Example 2. An MRS medium (1 mL) was added to the liquid after electroporation, and the mixture was cultured at 37° C. for 2 hours. Subsequently, the culture liquid was spread onto an MRS agar medium to which 20 µg/mL erythromycin had been added, followed by incubation at 37° C. for 2 or 3 days, whereby erythromycin-resistant colonies were obtained. A part of the colonies was removed, and insertion of a target plasmid into the target site was confirmed through PCR. PCR analysis employed a primer having a sequence selected from a region in the vicinity of the attB site of a *Lactobacillus casei* ATCC 334 chromosome, and a primer having a sequence selected from a region in the relatively vicinity of an end of the cloned region from cps1A to cps1J.

The thus-obtained *Lactobacillus casei* ATCC 334 having the genes cps1A, cps1B, cps1C, cps1D, cps1E, cps1F, cps1G, and cps1J which are derived from *Lactobacillus casei* YIT 9029 is represented by ATCC334 cps1A-J. Cells of the gene-transferred strain were prepared in a manner similar to that of Example 4.

Figure 9:
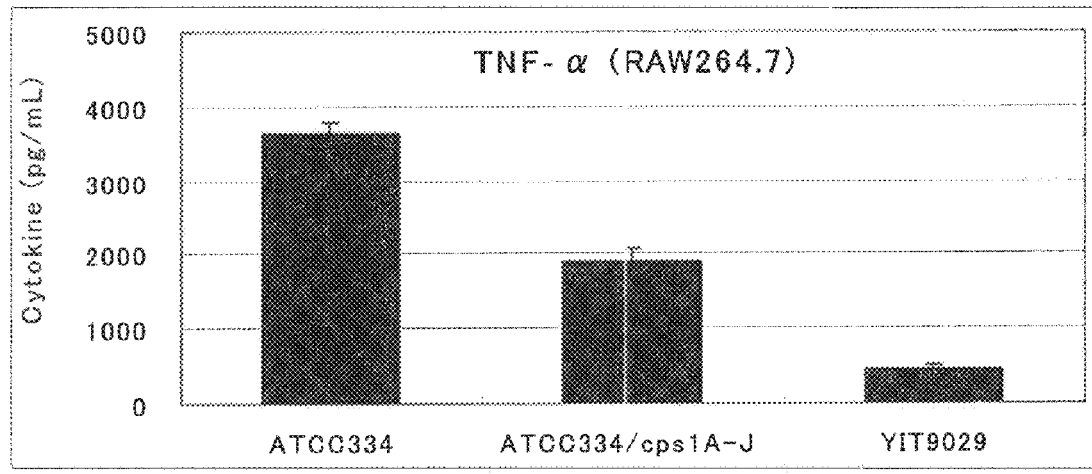
FIG. 9 shows TNF-α inducibility in murine macrophage RAW264.7 cells (amount of bacterial cells added: 1 μg/mL).
Figure 10:
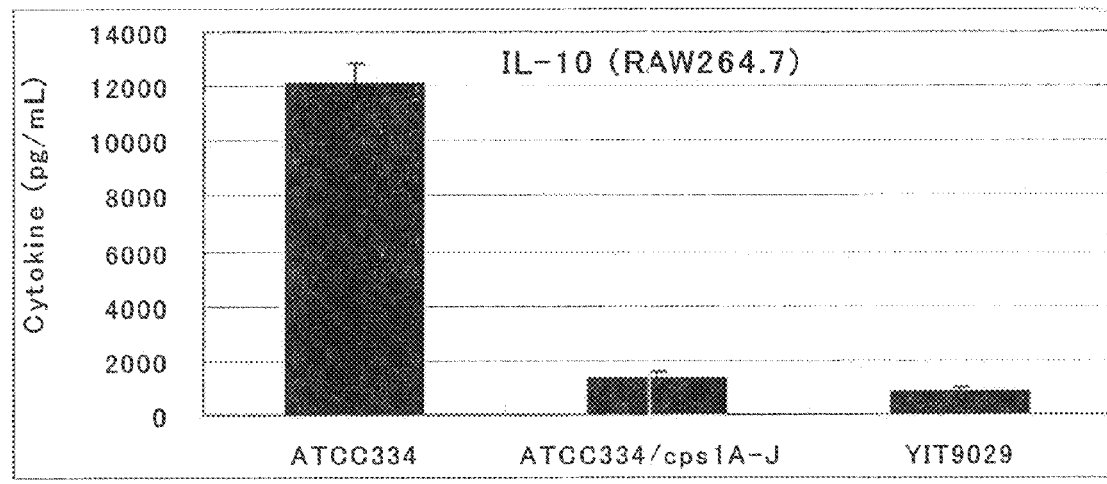
FIG. 10 shows IL-10 inducibility in murine macrophage RAW264.7 cells (amount of bacterial cells added: 1 μg/mL).
Figure 11:
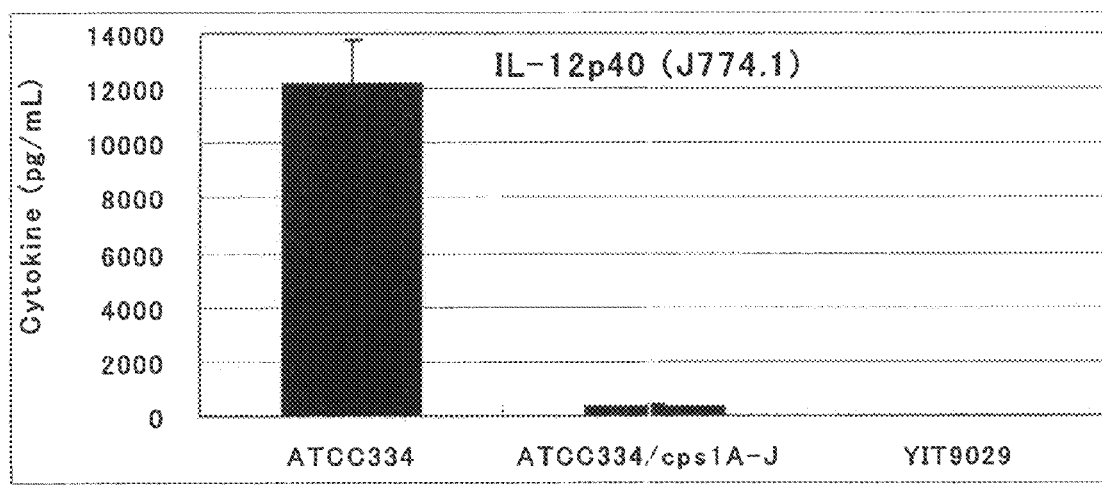
FIG. 11 shows IL-12p40 inducibility in murine macrophage J774.1 cells (amount of bacterial cells added: 1 μg/mL).

RAW264.7 cells (purchased from ATCC) and J774.1 cells (purchased from RIKEN Bio Resource Center (currently) (previously RIKEN Gene Bank)) were employed in a manner similar to that of Example 5. Subsequently, heat-killed lactic acid bacterium cells diluted with the culture liquid as described in Example 4, was added to the plate (100 µL/well) such that the final concentration was adjusted to 1 µg/mL, followed by culturing in an incubator (37° C., 5% $CO_2$) for 24 hours. Immediately after completion of culture, the supernatant was recovered, and the TNF-α, IL-10, and IL-12p40 levels of the supernatant were determined through ELISA (FIGS. 9 to 11).

When heat-killed cells of ATCC 334 cps1A-J, to which genes derived from a *Lactobacillus casei* YIT 9029 strain had been transferred, were added (1 µg/mL), the TNF-α production amount was smaller than that in the case of the parent strain ATCC 334. Therefore, the transferred genes were found to modify the immunoregulatory action of the parent ATCC 334 strain so as to suppress production of TNF-α. In addition, the ATCC 334 cps1A-J strain exhibited a considerably decreased activity on induction of IL-10 and IL-12p40 production, as compared with the production inducing activity of ATCC 334. Therefore, transfer of the genes cps1A through cps1J was found to suppress the IL-10 and IL-12p40 production inducing activity of the parent ATCC 334 strain in a macrophage strain.

Example 7

Modification of Cytokine Regulatory Activity of a Mutant Strain of *Lactobacillus casei* YIT 9029Δcps1C by Transfer of a Wild-Type cps1C Gene PCR was performed with two primers: an oligonucleotide 5'-tcccccgggttgggggaatctatcg-3' (SEQ ID NO: 51), having a sequence containing a ribosome-binding site sequence upstream of the cps1C gene and a sequence containing an Sma I restriction site on the 5'-end; and an oligonucleotide 5'-aaactgcagttatattttccatcgataaa-3' (SEQ ID NO: 52), having a sequence complementary to a region downstream of the cps1C gene and a sequence containing a Pst I restriction site on the 5'-end. By use of KOD Plus DNA polymerase, PCR was performed with DNA of *Lactobacillus casei* YIT 9029 as a template, whereby the cps1C gene was amplified. The thus-amplified DNA fragment was treated (including purification, concentration, digestion with restriction enzymes, etc.) in a manner similar to that of Example 2. Separately, a plasmid vector pYAP300 was also subjected to digestion with restriction enzymes, calf intestine phosphatase treatment, purification, and concentration, in a manner similar to that of Example 2. The DNA fragment was ligated to the plasmid vector, so that the gene cps1C was inserted to a region downstream of the transcription promoter of the vector, and the product was transferred to *E. coli* JM109 competent cells. The cells were spread onto an LB agar medium containing 500 µg/mL erythromycin, followed by culturing at 37° C. for 1 day. Plasmids were extracted from the obtained colonies, and a recombinant plasmid of interest was selected based on the lengths of the plasmid and restriction-enzyme-digested fragments.

Subsequently, cells of a *Lactobacillus casei* YIT 9029Δcps/C mutant strain were grown in an MRS medium, and a culture liquid in a logarithmic growth phase was centrifuged at 5,000×g and 4° C. for 5 minutes, whereby the cells were collected. The cells were subjected to electroporation in accordance with the method of Example 2. An MRS medium (1 mL) was added to the liquid after electroporation, and the mixture was cultured at 37° C. for 2 hours. Subsequently, the culture liquid was spread onto an MRS agar medium to which 20 μg/mL erythromycin had been added, followed by incubation at 37° C. for 2 or 3 days, whereby erythromycin-resistant colonies were obtained. A part of the colonies was removed, and insertion of a target plasmid into the attB site was confirmed through PCR. PCR analysis employed a primer having a sequence selected from a region in the vicinity of the attB site of a *Lactobacillus casei* YIT 9029 chromosome, and a primer having a sequence selected from the cloned cps1C region. The thus-obtained strain is represented by Δcps1C/cps1C strain. Cells of the gene-transferred strain were prepared in a manner similar to that of Example 4.

Figure 12:
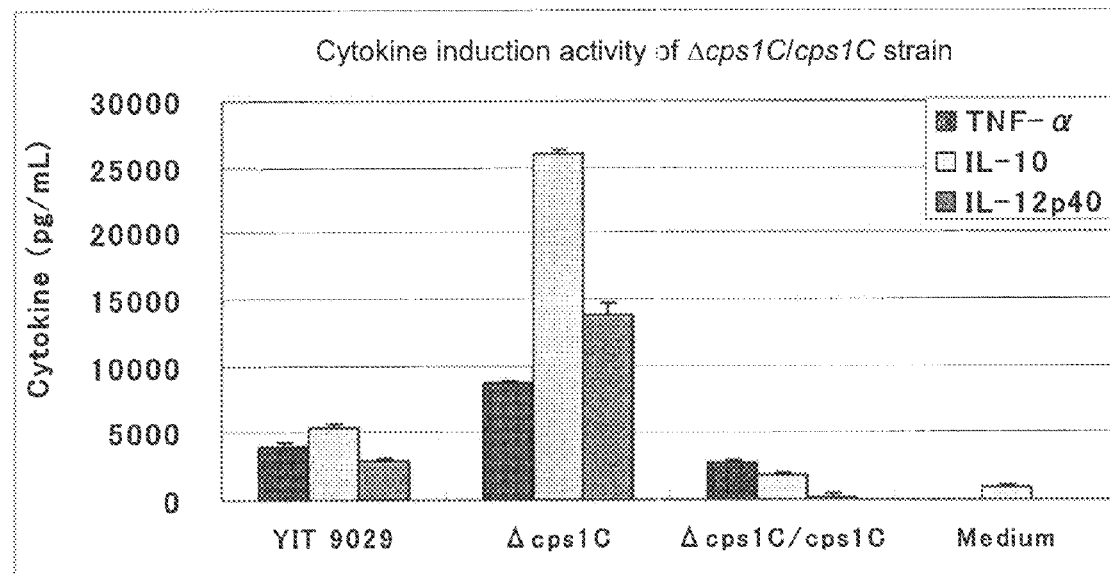
FIG. 12 shows TNF-α and IL-10 inducibility in murine macrophage RAW264.7 cells, and IL-12p40 inducibility in J774.1 cells (amount of bacterial cells added: 25 μg/mL).

Similar to Example 6, production of cytokine was investigated by use of RAW264.7 cells and J774.1 cells, to which cells of Δcps1C/cps1C strain were added. When cells of Δcps1C/cps1C strain were added, production of cytokines TNF-α, IL-12p40, and IL-10 was considerably suppressed, as compared with the case where cells of Δcps1C were added. The cytokine production inducing activity was equivalent to or lower than that of the parent *Lactobacillus casei* YIT 9029 (FIG. 12). This phenomenon was attributed to the following mechanism. Re-transfer of the cps1C gene to Δcps1C recovers the synthesis of cell wall polysaccharide. However, the expression amount of the cps1C gene is varied, since the transfer site is different. Therefore, cytokine production is further strongly suppressed.

Example 8

Figure 13:
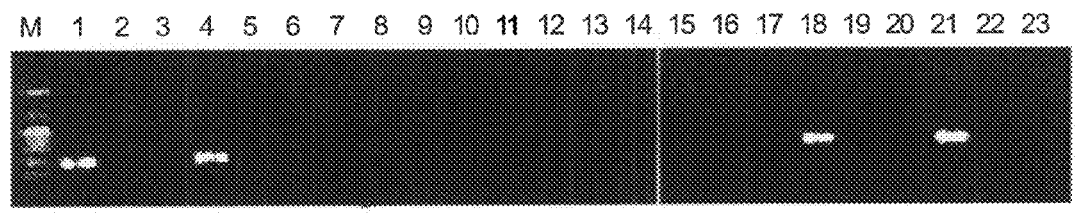
FIG. 13 shows detection of cps1D gene in strains of *Lactobacillus casei* (lane 1: YIT 9029, lane 2: YIT 0180, lane 3: YIT 0005, lane 4: YIT 0006, lane 5: YIT 0009, lane 6: YIT 0123, lane 7: YIT 0128, lane 8: YIT 0003, lane 9: YIT 0007, lane 10: YIT 0010, lane 11: YIT 0015, lane 12: YIT 0038, lane 13: YIT 0047, lane 14: YIT 0171, lane 15: YIT 0209, lane 16: YIT 0226, lane 17: YIT 0262, lane 18: YIT 0289, lane 19: YIT 0290, lane 20: YIT 0295, lane 21: YIT 0322, lane 22: YIT 0393, and lane 23: YIT 10029).

Strains of *Lactobacillus casei* shown in FIG. 13 were cultured in an MRS plate medium. The grown colonies were suspended in TE, and the suspension was heated at 94° C. for 3 minutes. The product was employed as a DNA extract. PCR was performed through employment of the DNA extract as a template and a primer set for amplifying the internal sequence of the cps1D gene (listed in Table 1). Specifically, PCR was performed by use of TaKaRa ExTaq (product of Takara Bio Inc.) under the conditions: 94° C.×2 minutes, (94° C.×10 seconds, 53° C.×10 seconds, 72° C.×1.5 minutes)×30, and 72° C.×5 minutes. The presence of amplified products was investigated through agarose gel electrophoresis. The results are shown in FIG. 13. As shown in FIG. 13, DNA fragments having the same size as that of a DNA fragment detected when YIT 9029 was employed were also found in the cases of the cells of a limited numbers of strains. Therefore, these cell strains were found to include at least a cps1D gene.

---

The invention claimed is:

1. An isolated gene encoding a protein selected from among the following proteins (a) to (c):
   (a) a protein having the amino acid sequence of SEQ ID NO: 6;
   (b) a protein which has an amino acid sequence equivalent to the amino acid sequence of (a), except that one to ten amino acid residues are deleted, substituted, or added, and which exhibits cytokine production regulatory activity; and
   (c) a protein which has an amino acid sequence having 90% or higher identity to the amino acid sequence of (a), and which exhibits cytokine production regulatory activity.

2. The isolated gene according to claim 1 encoding (a) a protein having the amino acid sequence of SEQ ID NO: 6.

3. The isolated gene according to claim 1 encoding (b) a protein which has an amino acid sequence equivalent to the amino acid sequence of (a), except that one to ten amino acid residues are deleted, substituted, or added, and which exhibits cytokine production regulatory activity.

4. The isolated gene according to claim 1 encoding (c) a protein which has an amino acid sequence having 90% or higher identity to the amino acid sequence of (a), and which exhibits cytokine production regulatory activity.

5. A microorganism in which a gene as recited in claim 1 has been introduced.

6. The microorganism as described in claim 5, which is a Gram-positive bacterium.

7. The microorganism as described in claim 6, wherein the Gram-positive bacterium is a bacterium belonging to the genus *Lactobacillus*.

8. The microorganism as described in claim 7, wherein the bacterium belonging to the genus *Lactobacillus* is *Lactobacillus casei*.

9. A food or beverage containing a microorganism as recited in claim 5.

10. A drug containing a microorganism as recited in claim 5.

11. A method for regulating cytokine production in a microorganism, comprising introducing a gene as recited in claim 1 into the microorganism.

12. An isolated gene having a polynucleotide selected from among the following polynucleotides (a) to (c):
   (a) a polynucleotide having the nucleotide sequence of SEQ ID NO: 5;
   (b) a polynucleotide which hybridizes, under stringent conditions, with a polynucleotide having a nucleotide sequence complementary to the nucleotide sequence of (a), and which encodes a protein exhibiting cytokine production regulatory activity, wherein said stringent conditions comprise 6×SSC, 0.5% SDS, 5×Denhardt's solution, and 100 mg/mL herring sperm DNA at 65° C. for 8 to 16 hours; and
   (c) a polynucleotide which has a nucleotide sequence having 90% or higher identity to the nucleotide sequence of (a), and which encodes a protein exhibiting cytokine production regulatory activity.

13. The isolated gene according to claim 12 having (a) a polynucleotide having the nucleotide sequence of SEQ ID NO: 5.

14. The isolated gene according to claim 12 having (b) a polynucleotide which hybridizes, under stringent conditions, with a polynucleotide having a nucleotide sequence complementary to the nucleotide sequence of (a), and which encodes a protein exhibiting cytokine production regulatory activity, wherein said stringent conditions comprise 6×SSC, 0.5% SDS, 5×Denhardt's solution, and 100 mg/mL herring sperm DNA at 65° C. for 8 to 16 hours.

15. The isolated gene according to claim 12 having (c) a polynucleotide which has a nucleotide sequence having 90% or higher identity to the nucleotide sequence of (a), and which encodes a protein exhibiting cytokine production regulatory activity.

16. A recombinant vector containing a gene as recited in claim 12.

17. A host microorganism containing a recombinant vector as recited in claim 16.

18. A nucleic acid fragment which specifically hybridizes with a gene as recited in claim 12 under stringent conditions comprising 6×SSC, 0.5% SDS, 5×Denhardt's solution, and 100 mg/mL herring sperm DNA at 65° C. for 8 to 16 hours.

19. A DNA array or DNA chip containing a gene as recited in claim 12.

20. A microorganism in which a gene as recited in claim 12 has been introduced.

21. The microorganism as described in claim 20, which is a Gram-positive bacterium.

22. The microorganism as described in claim 21, wherein the Gram-positive bacterium is a bacterium belonging to the genus *Lactobacillus*.

23. The microorganism as described in claim 22, wherein the bacterium belonging to the genus *Lactobacillus* is *Lactobacillus casei*.

24. A food or beverage containing a microorganism as recited in claim 20.

25. A drug containing a microorganism as recited in claim 20.

26. A method for regulating cytokine production in a microorganism, comprising introducing a gene as recited in claim 12 into the microorganism.

* * * * *